US009057049B2

(12) United States Patent
Vanavichit et al.

(10) Patent No.: US 9,057,049 B2
(45) Date of Patent: Jun. 16, 2015

(54) TRANSGENIC PLANTS WITH REDUCED EXPRESSION OF AMADH2 AND ELEVATED LEVELS OF 2-ACETYL-1-PYRROLINE

(75) Inventors: Apichart Vanavichit, Nakornpathom (TH); Somvong Tragoonrung, Pathumthani (TH); Theerayut Toojinda, Samutsakorn (TH); Samart Wanchana, Nakornpathom (TH); Wintai Kamolsukyunyong, Nakornpathom (TH); Siwaret Arikit, Nakornpathom (TH)

(73) Assignees: Kasetsart University, Bangkok (TH); National Science and Technology Development Agency, Pathumthani (TH)

( * ) Notice: Subject to any disclaimer, the term of this patent is extended or adjusted under 35 U.S.C. 154(b) by 320 days.

(21) Appl. No.: 12/961,398

(22) Filed: Dec. 6, 2010

(65) Prior Publication Data

US 2011/0179518 A1  Jul. 21, 2011

Related U.S. Application Data

(60) Continuation-in-part of application No. 12/013,404, filed on Jan. 11, 2008, now Pat. No. 7,847,083, which is a division of application No. 11/043,520, filed on Jan. 25, 2005, now Pat. No. 7,319,181.

(51) Int. Cl.
*C12N 9/02* (2006.01)
*C12N 15/82* (2006.01)
*C12N 15/113* (2010.01)
*C07K 14/415* (2006.01)

(52) U.S. Cl.
CPC .......... *C12N 9/0008* (2013.01); *C12N 15/8218* (2013.01); *C07K 14/415* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 5,702,933 A | 12/1997 | Klee et al. | |
| 7,319,181 B2* | 1/2008 | Vanavichit et al. | 800/285 |
| 7,847,083 B2 | 12/2010 | Vanavichit et al. | |
| 2003/0070192 A1 | 4/2003 | Keller et al. | |
| 2004/0216190 A1 | 10/2004 | Kovalic | |
| 2006/0123505 A1 | 6/2006 | Kikuchi et al. | |
| 2009/0176003 A1* | 7/2009 | Damude et al. | 426/611 |

FOREIGN PATENT DOCUMENTS

| | | |
|---|---|---|
| WO | 03/008540 A2 | 1/2003 |
| WO | 2006/032102 A1 | 3/2006 |

OTHER PUBLICATIONS

Niu et al. (2008) BMC Plant Biol. 8: 100.*
GenBank Accession No. AB333793.1 (2008).*
Wu et al. (2009) J. Food Sci. 74: S192-S197.*
GenBank Accession No. AK071221, 2003.*
Arai et al., "Proteomic Analysis of Highly Purified Peroxisomes from Etiolated Soybean Cotyledons", Plant Cell Physiol, vol. 49, No. 4, 2008, pp. 526-539.
Bradbury et al., "Inactivation of an Aminoaldehyde Dehydrogenase is Responsible for Fragrance in Rice", Plant Molecular Biology, vol. 68, 2008, pp. 439-449.
Miki et al., "Simple RNAi Vectors for Stable and Transient Suppression of Gene Function in Rice", Plant Cell Physiol, vol. 45, No. 4, 2004, pp. 490-495.
European Search Report received for EP Patent Application No. 06075179, mailed on Jun. 15, 2007, 12 pages.
Asayama, M., Oryza sativa (japonica cultivar-group) BADH2 mRNA for Betaine Aldehyde Dehydrogenase, Complete cds., GenBank Accession # AB096083, 2003, pp. 1-2.
"Betaine Aldehyde Dehydrogenase", UNIPROT Database Accession No. Q84LK3, 4 pages, Jun. 1, 2003.
Bradbury et al., "A Perfect Marker for Fragrance Genotyping in Rice", Molecular Breeding, vol. 16, No. 4, Nov. 2005, pp. 279-283.
Bradbury et al., "The Gene for Fragrance in Rice", Plant Biotechnology Journal, vol. 3, 2005, pp. 363-370.
Chen et al., "The fgr Gene Responsible for Rice Fragrance was Restricted within 69 kb", Plant Science, vol. 171, No. 4 Oct. 2006, pp. 505-514.
Christopher et al., "Marker Assisted Selection in Rice Improvement", Rural Industries Research and Development Corporation Aug. 2004, 15 pages.
"Classification and Nomenclature of Enzymes by the Reactions they Catalyse", Nomenclature Committee of the International Union of Biochemistry and Molecular Biology (NC-IUBMB), World Wide Web.chem.qmul.ac.uk/iubmb/enzymes/rules.html, pp. 1-15, 1992.
Colliver, S. P., "Differential Modification of Flavonoid and Isoflavonoid Biosynthesis with an Antisense Chalcone Synthase Construct in Transgenic Lotus Comiculatus", Plant Molecular Biology, vol. 35, 1997, pp. 509-522.
Cordeiro et al., "Identification of Microsatellite Markers for Fragrance in Rice by Analysis of the Rice Genome Sequence", Molecular Breeding, vol. 9, No. 4 2002, pp. 245-250.
Elomaa, P., "Transformation of Antisense Constructs of the Chalcone Synthase Gene Superfamily into *Gerbera* Hybrida: Differential Effect on the Expression of Family Members", Molecular Breeding, vol. 2 1996, pp. 41-50.
Elsley, Kevin, "Fragrant gene found", The Land, vol. 53, Nov. 18, 2004.

(Continued)

*Primary Examiner* — David T Fox
*Assistant Examiner* — Steven Bernacki
(74) *Attorney, Agent, or Firm* — Morrison & Foerster LLP

(57) ABSTRACT

The aromatic compound 2-acetyl-1-pyrroline-is the major potent flavor component of all aromatic rice and other plants. This present invention provides transgenic plants in which 2-acetyl-1-pyrroline is synthesized at a level greater than in naturally occurring non-aromatic varieties. The transgenic plants have reduced expression of the Os2AP gene and protein, resulting in an aromatic phenotype.

6 Claims, 27 Drawing Sheets

(56) References Cited

OTHER PUBLICATIONS

Garland et al., "Application of Molecular Markers to Rice Breeding in Australia", Rural Industries Research and Development Corporation, May 2001, 21 pages.
Garland et al., "PCR-Based Molecular Markers for the Fragrance Gene in Rice (*Oryza sativa*. L.)", Theoretical and Applied Genetics, vol. 101, No. 3, Aug. 2000, pp. 364-371.
Holmstrom et al., "Production of the *Escherichia coli* Betaine-Aldehyde Dehydrogenase, an Enzyme required for the Synthesis of the Osmoprotectant Glycine Betaine in Transgenic Plants", Plant Journal, vol. 6, No. 5, Nov. 1994, pp. 749-758.
Horiguchi, G., "RNA Silencing in Plants: a Shortcut to Functional Analysis", Differentiation, vol. 72 2004, pp. 65-73.
Jain et al., "SSR Analysis of Chromosome 8 Regions Associated with Aroma and Cooked Kernel Elongation in Basmati rice", Euphytica, vol. 152, No. 2, Nov. 2006, pp. 259-273.
Jia et al., "Transformation of Tomato with the BADH Gene from Atriplex Improves Salt Tolerance", Plant Cell Reports, vol. 21, No. 2, 2002.
Jin et al., "A Single Nucleotide Polymorphism (SNP) Marker Linked to Fragrance in Rice (*Oryza sativa* L.)", Plant Science, vol. 165, No. 2, Aug. 2003, pp. 359-364.
Jin et al., "Identification and Potential use of RAPS Marker for Aroma in Rice", Journal of Genetics and Breeding, vol. 50, No. 4 Dec. 1996, pp. 367-370.
Kamolsukyunyong et al., "Aroma Gene of Thai Horn Mali Rice", Lab Today, vol. 9, 2003, pp. 66-69.
Kamolsukyunyong et al., "Isogenic Lines Carrying the 26.7-kb Genomic Region on Chromosome 8 of KDML105 are Charactarized as Aromatic Rice", Proceeding of the Conference on Rice Biotechnology, Peach, Pattaya, Thailand Jul. 18, 2003, pp. 151-155.
Lorieux et al., "Aroma in Rice: Genetic Analysis of a Quantitative Trait", Theor Appl Genet., vol. 93, 1996, pp. 1145-1151.
Nagsuk et al., "Identification of 2-Acetyl-1-Pyrroline, the Principal Aromatic Rice Flavor Compound, in Fungus Cultures", Proceedings of the 2nd International Conference on Medicinal Mushrooms & International Conference on Biodiversity and Bioactive Compounds, 2003, pp. 395-400.
Sasaki et al., "*Oryza sativa* nipponbare (GA3) genomic DNA", Chromosome 8, PAC clone:p456B03, EMBL database Accession No. AP004463, Dec. 13, 2001, 37 pages.
Vanavichit, A., "Discovering Genes for Rice Grain Aroma", Proceedings of the 1st International Conference on Rice for the Future, Bangkok, Thailand, Aug. 31-Sep. 3, 2004, pp. 71-80.
Wanchana et al., "A Rapid Construction of a Physical Contig across a 4.6 GM Region for Rice Grain Aroma Facilitates Marker Enrichment for Positional Cloning", Science Asia, vol. 31, 2005, pp. 299-306.
Wanchana et al., Enhancing 2-Acetyl-1-Pyrroline Synthesis in Rice Leaves by RNAi-Mediated Suppression of Os2AP Converts Non-aromatic to Aromatic Rice (*Oryza sativa* L. ), Proceedings of the 1st International Conference on Rice for the Future, Bangkok, Thailand Aug. 31-Sep. 3, 2004, p. 105.
Wanchana et al., "Physical Mapping of the Region Proximal to Genes Controlling Aroma in Rice", RGJ-Ph.D. Congress II, Chonburi, Thailand, 2001, p. 153.
Wanchana et al., "RNAi-Mediated Suppression of Os2AP Converts Non-aromatic to Aromatic Rice", RGJ-Ph.D. Congress VI, Chonburi, Thailand, 2005, p. 160.
Wanchana et al., "Sequence Variation in BADH is Associated with the Synthesis of 2AP, a Potent Aroma Determination in Rice", RGJ-Ph.D. Congress IV, Chonburi, Thailand, 2003, p. 162.
Wanchana et al., "Sequence Variation of BADH is Associated with the Synthesis of 2AP, a Potent Aroma Determination in rice", Proceedings of the Conference on Rice Biotechnology 2003, Peach, Pattaya, Thailand, 2003, pp. 157-160.
Wanchana et al., "Sequence Variation on BADH Associated with 2-Acetyl-1-Pyrroline, the Potent Aroma Compound in Rice", The 4th National Symposium on Graduate Research, Lotus Hotel Pang Suan Kaew, Chiang Mai, Thailand Aug. 10-11, 2004, p. 105.

\* cited by examiner

Figure 5A

```
NIPPONBARE  ATGGCCACGGCGATCCCGCAGCGGCAGCTCTTCGTCGCCGGCGAGTGGCGCCCCCGCG  60
            ||||||||||||||||||||||||||||||||||||||||||||||||||||||||||||
THM         ATGGCCACGGCGATCCCGCAGCGGCAGCTCTTCGTCGCCGGCGAGTGGCGCCCCCGCG  60

NIPPONBARE  CTCGGCCGCCGCTCCCCGTCGTCAACCCCGCCACCGAGTCCCCATCGGCGAGATCCCG  120
            ||||||||||||||||||||||||||||||||||||||||||||||||||||||||||||
THM         CTCGGCCGCCGCTCCCCGTCGTCAACCCCGCCACCGAGTCCCCATCGGCGAGATCCCG  120

NIPPONBARE  GCGGGCACGGCGGAGGACGTGGACGCGCGGTGGCGCGGCGGGAGGCGCTGAAGAGG  180
            |||||||||||||||||||||||||||||||||||||||||||||||||| | |
THM         GCGGGCACGGCGGAGGACGTGGACGCGCGGTGGCGCGGCGGGAGGCGCTTAAAAAG  180

NIPPONBARE  AACCGGGGCCCGGACTGGGCGCGCGGCGCCGTCCGGGCCCAAGTACCTCCGCGCA  240
            |||||||||||||||||||||||||||||||||| |
THM         AACCCGGGCCCGGACTGGGCGCGCGGCGCCGTCCGGGCCCAAGTACATTCGCGCA  240

NIPPONBARE  ATCGCGGCCAAGATAATCGAGAGGAAATCTGAGCTGGCTAGACTGGACACGCTTGATTGT  300
            ||||  ||||||| |||||||||||||||||||||||||||||||||||||||||||||
THM         ATCGCTGACAAAATAATCGAGAGGAAATCTGAGCTGGCTAGACTGGACACGCTTGATTGT  300

NIPPONBARE  GGGAAGCCTCTTGATGAAGCAGCATGGGACATGGACGATGTTGCTGATGCTTTGAGTAC  360
            |||||||||||||||||||||||||||||||||||||||||||||||||||||||||
THM         GGGAAGCCTCTTGATGAAGCAGCATGGGACATGGACGATGTTGCTGATGCTTTGAGTAC  360

NIPPONBARE  TTTGCAGATCTTGCAGAATCCTTGGACAAAAGGCAAAATGCACCTGTCTCTCTTCCAATG  420
            ||||||||||||||||||||||||||||||||||||||||||||||||||||||||||||
THM         TTTGCAGATCTTGCAGAATCCTTGGACAAAAGGCAAAATGCACCTGTCTCTCTTCCAATG  420

NIPPONBARE  GAAAACTTTAAATGCTATCTTCGGAAAGAGCCTATCGGTGTAGTTGGGTTGATCACACCT  480
            ||||||||||||||||||||||||||||||||||||||||||||||||||||||||||||
THM         GAAAACTTTAAATGCTATCTTCGGAAAGAGCCTATCGGTGTAGTTGGGTTGATCACACCT  480

NIPPONBARE  TGGAACTATATCCTCTCCTGATGGCAACATGGAAGGTAGCTCCTGCCCTGCTGCTGGCTGT  540
            ||||||||||||||||||||||||||||||||||||||||||||||||||||||||||||
THM         TGGAACTATATCCTCTCCTGATGGCAACATGGAAGGTAGCTCCTGCCCTGCTGCTGGCTGT  540
```

Figure 5B

| | | |
|---|---|---|
| NIPPONBARE | ACAGCTGTACTAAAAACCATCTGAATTGGCTTCCGTGACTTGTTTGGAGCTTGCTGATGTG | 600 |
| THM | ACAGCTGTACTAAAAACCATCTGAATTGGCTTCCGTGACTTGTTTGGAGCTTGCTGATGTG | 600 |
| NIPPONBARE | TGTAAAGAGGTTGGTCTTCCTTCAGGTGTCTAAACATAGTGACTGGATTAGGTTCTGAA | 660 |
| THM | TGTAAAGAGGTTGGTCTTCCTTCAGGTGTCTAAACATAGTGACTGGATTAGGTTCTGAA | 660 |
| NIPPONBARE | GCCGGTGCTCCTTTGTCATCACACCCTGGTGTAGACAAGGTTGCATTTACTGGGAGTTAT | 720 |
| THM | GCCGGTGCTCCTTTGTCATCACACCCTGGTGTAGACAAGGTTGCATTTACTGGGAGTTAT | 720 |
| NIPPONBARE | GAAACTGGTAAAAAGATTATGCTTCAGCTGCTCCTATGGTTAAGCCTGTTTCACTGGAA | 780 |
| THM | GAAACTGGTATATA------TTTCAGCTGCTCCTATGGTTAAGCCTGTTTCACTGGAA | 772 |
| NIPPONBARE | CTTGGTGGAAAAAGTCCTATAGTGGTGTTTGATGATGTTGATGTTGAAAAAGCTGTTGAG | 840 |
| THM | CTTGGTGGAAAAAGTCCTATAGTGGTGTTTGATGATGTTGATGTTGAAAAAGCTGTTGAG | 832 |
| NIPPONBARE | TGGACTCTCTTTGGTTGCTTTTGGACCAATGGCCAGATTTGCAGTGCAACATCGCGTCTT | 900 |
| THM | TGGACTCTCTTTGGTTGCTTTTGGACCAATGGCCAGATTTGCAGTGCAACATCGCGTCTT | 892 |
| NIPPONBARE | ATTCTTCATAAAAAAATCGCTAAAGAATTTCAAGAAAGGATGGTTGCATGGGCCAAAAAT | 960 |
| THM | ATTCTTCATAAAAAAATCGCTAAAGAATTTCAAGAAAGGATGGTTGCATGGGCCAAAAAT | 952 |
| NIPPONBARE | ATTAAGGTGTCAGATCCACTTGAAGAGGGTTGCAGGCTTGGGCCCGTTGTTAGTGAAGGA | 1020 |
| THM | ATTAAGGTGTCAGATCCACTTGAAGAGGGTTGCAGGCTTGGGCCCGTTGTTAGTGAAGGA | 1012 |
| NIPPONBARE | CAGTATGAGAAGATTAAGCAATTTGTATCTACCGCCAAAAGCCAAGGTGCTACCATTCTG | 1080 |
| THM | CAGTATGAGAAGATTAAGCAATTTGTATCTACCGCCAAAAGCCAAGGTGCTACCATTCTG | 1072 |

Figure 5C

```
NIPPONBARE  ACTGGTGGGGTTAGACCCAAGCATCTGGAGAAAGTTTCTATATTGAACCCACAATCATT  1140
            ||||||||||||||||||||||||||||||||||||||||||||||||||||||||||||
THM         ACTGGTGGGGTTAGACCCAAGCATCTGGAGAAAGTTTCTATATTGAACCCACAATCATT  1132

NIPPONBARE  ACTGATGTCGATACATCAATGCAAATTTGGAGGGAAGAAGTTTTTGGTCCAGTGCTCTGT  1200
            ||||||||||||||||||||||||||||||||||||||||||||||||||||||||||||
THM         ACTGATGTCGATACATCAATGCAAATTTGGAGGGAAGAAGTTTTTGGTCCAGTGCTCTGT  1192

NIPPONBARE  GTGAAAGAATTTAGCACTGAAGAAGAAGCCATTGAATTGGCCAACGATACTCATTATGGT  1260
            ||||||||||||||||||||||||||||||||||||||||||||||||||||||||||||
THM         GTGAAAGAATTTAGCACTGAAGAAGAAGCCATTGAATTGGCCAACGATACTCATTATGGT  1252

NIPPONBARE  CTGGCTGGTGCTGTGCTTTCCGGTGACCGCGAGCGATGCCAAGCCCTGCTTCTGCCAAGC  1320
            ||||||||||||||||||||||||||||||||||||||||||||||||||||||||||||
THM         CTGGCTGGTGCTGTGCTTTCCGGTGACCGCGAGCGATGCCAAGCCCTGCTTCTGCCAAGC  1312

NIPPONBARE  GATGCCGGAATTATCTGGGTGAACTGCTGCTCGGCAACCCTGCTTCTGCCAAGCTCCATGGGGC  1380
            ||||||||||||||||||||||||||||||||||||||||||||||||||||||||||||
THM         GATGCCGGAATTATCTGGGTGAACTGCTGCTCGGCAACCCTGCTTCTGCCAAGCTCCATGGGGC  1372

NIPPONBARE  GGGAACAAGCGCAGCGGCTTTGGACGCGAGCTCGGAGAAGGGGCATTGACAACTACCTA  1440
            ||||||||||||||||||||||||||||||||||||||||||||||||||||||||||||
THM         GGGAACAAGCGCAGCGGCTTTGGACGCGAGCTCGGAGAAGGGGCATTGACAACTACCTA  1432

NIPPONBARE  AGCGTCAAGCAAGTGACGGAGTACGCCTCCGATGAGCCGTGGGGATGTACAAATCCCT  1500
            ||||||||||||||||||||||||||||||||||||||||||||||||||||||||||||
THM         AGCGTCAAGCAAGTGACGGAGTACGCCTCCGATGAGCCGTGGGGATGTACAAATCCCT  1492

NIPPONBARE  TCCAAGCTGTAA  1512  (SEQ ID NO: 5)
            ||||||||||||
THM         TCCAAGCTGTAA  1504  (SEQ ID NO: 2)
```

Figure 5D

```
                    8 bp deletion
                     in exon 7
Nipponbare  TGCATTTACTGGAGTTATGAAACTGGTAAAAGATTATGGCTTCAGCTGCTCCTATGGTTAAG              (SEQ ID NO: 5)
THM         TGCATTTACTGGAGTTATGAAACTGGTATATA--------TTTCAGCTGCTCCTATGGTTAAG              (SEQ ID NO: 2)
            *******************************         ***********************

Nipponbare  MATAIPQRQLFVAGEWRAPALGRRLPVVNPATESPIGEIPAGTAEDVDAAVAAAREALKR
THM         MATAIPQRQLFVAGEWRAPALGRRLPVVNPATESPIGEIPAGTAEDVDAAVAAAREALKK Nipponbare  N RGRDWA RAPGAVRAKY LRATA AKI IERKSELARLETLDCGKPLDEAAWDMDDVAGCFEY
THM         N PGRDWA PAPGAVRAKY IRATA DKI IERKSELARLETLDCGKPLDEAAWDMDDVAGCFEY Nipponbare  FADLAESLDKRQNAPVSLPMENFKCYLRKEPIGVVGLITPWNYPLLMATWKVAPALAAGC
THM         FADLAESLDKRQNAPVSLPMENFKCYLRKEPIGVVGLITPWNYPLLMATWKVAPALAAGC Nipponbare  TAVLKPSELASVTCLELADVCKEVGLPSGVLNIVTGLGSEAGAPLSSHPGVDKVAFTGSY
THM         TAVLKPSELASVTCLELADVCKEVGLPSGVLNIVTGLGSEAGAPLSSHPGVDKVAFTGSY Nipponbare  ETG KKIMA SAAPMVKPVSLELGGKSPIVVFDDVDVEKAVEMTLFGCFWTNGQICSATSRL
THM         ETG IYFSC SYG Nipponbare  ILHKKIAKEFQERMVAWAKNIKVSDPLEEGCRLGPVVSEGQYEKIKQFVSTAKSQGATIL
THM Nipponbare  TGGVRPKHLEKGFYIEPTIITDVDTSMQIWREEVFGPVLCVKEFSTEEEAIELANDTHYG
THM Nipponbare  LAGAVLSGDRERCQRLTEEIDAGIIWNCSQPCFCQAPWGGNKRSGFGRELGEGGIDNYL
THM Nipponbare  SVKQVTEYASDEPWGMYKSPSKL        (SEQ ID NO: 6)
THM                                        (SEQ ID NO: 3)
```

Graphical genotypes of eight F11 plants from the single F6 plant and the analysis of 2-acetyl-1-pyrroline levels from the rice grains.

FIGURE 9A

| | | |
|---|---|---|
| Thai Hom Mali | TGCATTTACTGGGAGTTATGAAACTGGTATATA------T---TTCAGCTGCTCCTATGGTTAAG (SEQ ID NO: 2) | aroma (A) |
| O. Rufipogon 06092 | TGCATTTACTGGGAGTTATGAAACTGGTATATA------T---TTCAGCTGCTCCTATGGTTAAG (SEQ ID NO: 89) | aroma (A) |
| O. Rufipogon 09351 | TGCATTTACTGGGAGTTATGAAACTGGTATATA------T---TTCAGCTGCTCCTATGGTTAAG (SEQ ID NO: 90) | aroma (A) |
| O. Rufipogon 10563 | TGCATTTACTGGGAGTTATGAAACTGGTATATA------T---TTCAGCTGCTCCTATGGTTAAG (SEQ ID NO: 91) | aroma (A) |
| O. rufipogon 07919 | TGCATTTACTGGGAGTTATGAAACTGGTAAAAGATTATGGCTTCAGCTGCTCCTATGGTTAAG (SEQ ID NO: 92) | Non aroma (NA) |
| O. nivara 18341 | TGCATTTACTGGGAGTTATGAAACTGGTATATA------T---TTCAGCTGCTCCTATGGTTAAG (SEQ ID NO: 93) | aroma (A) |
| O. nivara 18261 | TGCATTTACTGGGAGTTATGAAACTGGTAAAAGATTATGGCTTCAGCTGCTCCTATGGTTAAG (SEQ ID NO: 94) | Non aroma (NA) |
| Nipponbare | TGCATTTACTGGGAGTTATGAAACTGGTAAAAGATTATGGCTTCAGCTGCTCAGCTGCTCCTATGGTTAAG (SEQ ID NO: 5) | Non aroma (NA) |
| JHN | TGCATTTACTGGGAGTTATGAAACTGGTAAAAGATTATGGCTTCAGCTGCTCAGCTGCTCCTATGGTTAAG (SEQ ID NO: 95) | Non aroma (NA) |

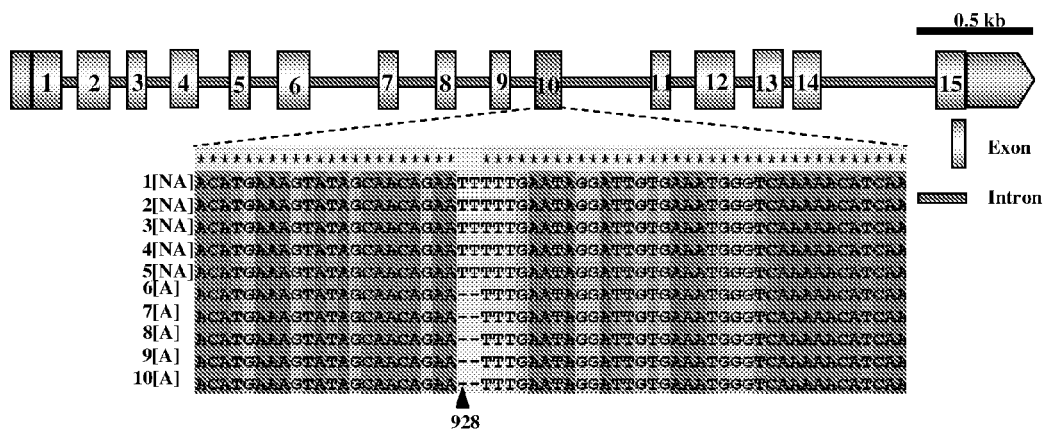

B.
```
atgagcatcccaattccccatcggcagttattcatagacggagactggaaagtcccgtc
 M  S  I  P  I  P  H  R  Q  L  F  I  D  G  D  W  K  V  P  V
ctcaagaatcggattcccatcatcaaccctccacccaacacatcatcggggatatccca
 L  K  N  R  I  P  I  I  N  P  S  T  Q  H  I  I  G  D  I  P
gcagctactaaggaagacgttgatctcgctgtcgctgccgccaaagctgccctctcccgc
 A  A  T  K  E  D  V  D  L  A  V  A  A  A  K  A  A  L  S  R
aacaagggcgccgattggcctccgcttccggctccgttcgggctcgctacctccgcgcc
 N  K  G  A  D  W  A  S  A  S  G  S  V  R  A  R  Y  L  R  A
atcgctgccaagatcaccgagaaaaagcctgaactagcaaaactcgaagctattgactgt
 I  A  A  K  I  T  E  K  K  P  E  L  A  K  L  E  A  I  D  C
ggaaaaccgctcgatgaagccgcctgggacatcgacgatgttgctggttgctttgagttc
 C  K  P  L  D  E  A  A  W  D  I  D  D  V  A  G  C  F  E  F
tatgctgaccttgctgaaaattggacgcacagcaaaaggctcatgtgtctcttcccatg
 Y  A  D  L  A  E  K  L  D  A  Q  Q  K  A  H  V  S  L  P  M
gacacattcaagagttatgttcttaaggagccgattggagtcgttgctttaataactcct
 D  T  F  K  S  Y  V  L  K  E  P  I  G  V  V  A  L  I  T  P
tggaattatcctctgttgatggctacgtggaaggttgctcctgctctgcggccggctgt
 W  N  Y  P  L  L  M  A  T  W  K  V  A  P  A  L  A  A  G  C
gctgcaatattgaagccctcrgagttggcatctgtgacatgtttggagctcgctgaaatt
 A  A  I  L  K  P  S  E  L  A  S  V  T  C  L  E  L  A  E  I
tgcaaagaagtcgggcttcctcctggcgtgttgaacattctcactggattaggacctgaa
 C  K  E  V  G  L  P  P  G  V  L  N  I  L  T  G  L  G  P  E
gcgggtgctccttagcagctcatcccgatgtagacaagattgcctttactggaagctct
 A  G  A  P  L  A  A  H  P  D  V  D  K  I  A  F  T  G  S  S
gcaactgggagcaaaattatgacagctgcagctcagctgatcaagcctgtttcactagag
 A  T  G  S  K  I  M  T  A  A  A  Q  L  I  K  P  V  S  L  E
cttggtgggaaaagccaatcattgttttgaggatgttgaccttgacaagctgctgaa
 L  G  G  K  S  P  I  I  V  F  E  D  V  D  L  D  K  A  A  E
tggaccatattggttgcttctggacaaatggtcagatatgcagtgcacttcccgcctt
 W  T  I  F  G  C  F  W  T  N  G  Q  I  C  S  A  T  S  R  L
attgtacatgaaagtatagcaacagaatttgaatatggattgtgaaatgggtcaaaacat
 I  V  H  E  S  I  A  T  E  F  E  *
caaaatttctgatcccttggaagaaggttgcagactaggccctattgttagtgaaggaca
gtatgaaaagatattgaagtttatctcaaatgctaagagtgaaggqtgcaaccatttqac
tggtgggtctcgcccagagcatctaaagaagggattctttgttgaaccaactgtcataac
tgatgtaactaccccatgcaaatttggagagaagaagtatttggaccagttctctgtgt
aaaaccatttagcactgaggaagaagctattgatctagcaatgacactgtatatggctt
gggttctgctgtaatatcaaatgatctagaaagatgtgagcgcattactaaggctttaa
ggctggaattgtgtggattaattgctccaaccatgcttcactcaagcccatggggagg
cattaaacgcagtggttttggtcgtgaattaggagaatgggacttgataattacttgag
tgtgaagcaagtgacccaatatatctctgatgaaccgtgggctggtaccagtctccttc
aaggctgtga
```

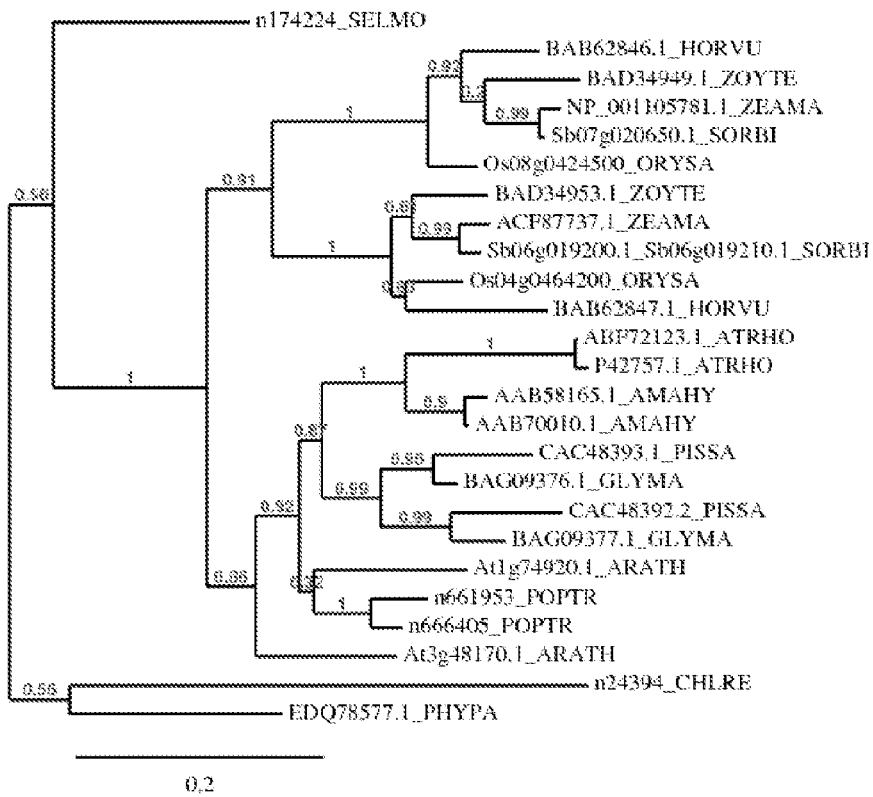

B.

| Monocotyledonous plant | | Dicotyledonous plant | |
|---|---|---|---|
| Os08g0424500_ORYSA | FwTNGQICSATS | At3g48170.1_ARATH | FwTNGQICSATS |
| NP_001105781.1_ZEAMA | FwTNGQICSATS | At1g74920.1_ARATH | FwTNGQICSATS |
| Sb07g020650.1_SORBI | FwTNGQICSATS | 661953_POPAL | FwTNGQICSATS |
| BAD34949.1_ZOYTE | FwTNGQICSATS | 666405_POPAL | FwTNGQICSATS |
| BAD86758.1 LEYCH | FwTNGQICSATS | BAG09376.1_GLYMA | FwTNGQICSATS |
| BAB62846.1_HORVU | FwTNGQICSATS | BAG09377.1_GLYMA | FfTNGQICSATS |
| | | CAC48393.1_PISSA | FwTNGQICSATS |
| Os04g0464200_ORYSA | FaNAGQVCSATS | CAC48392.2_PISSA | FfTNGQICSATS |
| ACF87737.1_ZEAMA | FaNAGQVCSATS | BAB18544.1_AVIMA | FwTNGQICSATS |
| Sb06g019200.1_Sb06g019210.1_SORBI | FaNAGQVCSATS | BAB18543.1_AVIMA | FwTNGQICSATS |
| BAD34953.1_ZOYTE | FaNGGQVCSATS | CAO14879.1_VITVI | FpNNGQICSATS |
| BAD86757.1 LEYCH | FfNGGQVCSATS | CAO64403.1_VITVI | FwTNGQICSATS |
| BAB62847.1_HORVU | FfNGGQVCSATS | AAB58165.1_AMAHY | FwTNGQICSATS |
| Primitive | | AAB70010.1 AMAHY | FwTNGQICSATS |
| XP_001756623.1_PHYPA | FwTNGQICSATS | ABF72123.1_ATRHO | FwTNGQICSATS |
| n174224_SELMO | FwTNGQICSATS | P42757.1_ARTHO | FwTNGQICSATS |
| n24394_CHLRE | FwTNGQICSSTS | | |

[FYLVA] - x - {GVEP} - [DILV] - G - [QE] - {LPYG} - C - [LIVMGSTANC] - [AGCN] - {HE} - [GSTADNEKR]

TRANSGENIC PLANTS WITH REDUCED EXPRESSION OF AMADH2 AND ELEVATED LEVELS OF 2-ACETYL-1-PYRROLINE

CROSS-REFERENCE TO RELATED APPLICATIONS

This application is a continuation-in-part of U.S. patent application Ser. No. 12/013,404, filed Jan. 11, 2008, which is a divisional of U.S. patent application Ser. No. 11/043,520, filed Jan. 25, 2005, now U.S. Pat. No. 7,319,181, all of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 584572000120SubSeqList2.txt, date recorded: Dec. 23, 2014, size: 63 KB).

FIELD OF THE INVENTION

The present invention relates generally to plant molecular genetics. In particular, it relates to non-naturally occurring plants and fungi that have elevated levels of 2-acetyl-1-pyrroline, methods for making such plants and fungi, and nucleic acids involved in the synthesis of 2-acetyl-1-pyrroline.

BACKGROUND OF THE INVENTION

Grain aroma is the most attractive characteristic of high quality rice increasingly demanded not only by the Asian market but also widely recognized in Europe and all over the world. Cooked rice fragrance is composed of more than one hundred volatile compounds such as hydrocarbons, alcohols, aldehydes, ketones, acids, esters, phenols, pyridines, pyrazines, and other compounds (Yajima et al., 1978; Maga, 1984; Takashi et al., 1980; Paule and Power, 1989). The "popcorn-like" aromatic compound, 2-acetyl-1-pyrroline (2AP), was discovered as the major potent flavor component of all aromatic rice, crust of bread wheat and rye bread (Buttery et al., 1982, 1983). 2-acetyl-1-pyrroline is chiefly responsible for the characteristic fragrance of many aromatic rice varieties (Tanchotikul and Hsieh, 1991). Surprisingly, this rice fragrance has also been isolated and identified from pandan leaves (Buttery et al., 1983), bread flowers (Vallaris Glabra Ktze.) (Wongpornchai et al., 2003), wet millet (Seitz et al., 1993), popcorn (Schieberle, 1991), *Bacillus ceres* (Romanczyk et al., 1995), fungi (Nagsuk et al., 2004), and aromatic vegetable soybean (*Glycine max*) (Fushimi and Masuda, 2001). 2-acetyl-1-pyrroline is present in all parts of the aromatic rice plant (stems, leaves, grains) except roots (Lorieux et al., 1996). While this fragrance is present in aromatic grains, it is not present in all grains.

The aromatic compound 2-acetyl-1-pyrroline has a pyrroline ring similar to the amino acid proline (FIG. 1). The first evidence linking the amino acid proline as the precursor synthesizing 2-acetyl-1-pyrroline was found in experiments in cell and callus culture (Suprasanna et al., 1998; Suprasanna et al., 2002). That conclusion was supported by experiments using isotopic labeling showing that the precursor of the grain 2-acetyl-1-pyrroline is most likely the amino acid proline in That Hom Mali (THM) Rice (Yoshihashi et al., 2002) and probably in other aromatic rice. However, the exact biosynthetic pathway of 2-acetyl-1-pyrroline is yet to be elucidated.

Thus, there is a need to identify genes involved in 2-acetyl-1-pyrroline synthesis and provide a method to increase 2-acetyl-1-pyrroline levels in plants and fungi to increase aroma.

SUMMARY OF THE INVENTION

The present invention meets these needs by providing non-naturally occurring plants and fungi in which the compound 2-acetyl-1-pyrroline (2AP) is produced at an elevated level compared to control plants and fungi. Control plants and fungi refer to plants and fungi of a similar or related genotype that have lower levels of the compound 2-acetyl-1-pyrroline. Such control plants can be non-naturally occurring. The present invention further provides methods for screening for and creating such non-naturally occurring plants and fungi, and seeds produced from said plants.

The exact biosynthetic pathway of the compound 2-acetyl-1-pyrroline is known as a product of the polyamine pathway (Vanavichit and Yoshihashi, 2010). It was hypothesized that gamma amino butyraldehyde (GBAL) can be converted to gamma amino butyraldehydev(GABA) by amino aldehyde dehydrogenase (AMADH), which is also known as Os2AP. In naturally occurring aromatic plants, mutations in coding sequences of Os2AP inactivate the enzyme and subsequently generate much less GABA than naturally occurring non-aromatic plants. Therefore, in aromatic plants, GBAL is more available for conversion to 1-pyrroline and 2-acetyl-1-pyrroline. Inhibition of AMADH increases the availability of GBAL for 1-pyrroline and 2-acetyl-1-pyrroline synthesis (FIG. 4A). A gene encoding a protein controlling aroma in rice, named Os2AP was identified as a member of the aldehyde dehydrogenase (AMADH) family that may play a key role in the conversion of GBAL to GABA. All aromatic rice varieties tested have an eight nucleotide deletion in this gene. The deletion creates a premature stop codon that leads to nonsense mediated degradation against its own mRNA, leading to a loss-of-function phenotype. RNA interference (RNAi) studies showed that disruption of transcription of the Os2AP gene led to elevated levels of 2-acetyl-1-pyrroline in plants, along with increased aroma.

Further, a gene encoding a homolog of rice Os2AP, GmAMADH2, was identified in soybean. All aromatic soybean varieties tested have a two nucleotide deletion in this gene. The deletion creates a premature stop codon that leads to nonsense mediated degradation against its own mRNA, leading to a loss-of-function phenotype. RNA interference (RNAi) studies showed that disruption of transcription of the soybean Os2AP gene led to elevated levels of 2-acetyl-1-pyrroline in plants. Moreover, *Arabidopsis thaliana*, a another model dicot, was transformed with heterologous GmAMADH2 RNAi, which resulted in increased production of 2-acetyl-1-pyrroline. These experiments show that Os2AP-like homologs can be used to generate aromatic plants in any plant species.

The present invention provides non-naturally occurring plants and fungi with an elevated level of 2-acetyl-1-pyrroline created by inhibiting the expression of the Os2AP gene or genes encoding homologs of Os2AP, reducing the mRNA levels of the Os2AP gene or genes encoding homologs of Os2AP, and/or reducing the activity of the Os2AP protein or homologs of the Os2AP protein. The level of Os2AP protein or homologs of Os2AP protein can be decreased by 25 percent, 50 percent, or 100 percent compared to a control plant. The inhibition of expression of the Os2AP gene or genes encoding homologs of Os2AP or reduction of mRNA levels of the Os2AP gene or genes encoding homologs of Os2AP can be accomplished by: a) expression of the Os2AP gene or genes encoding homologs of Os2AP or a fragment thereof in the antisense orientation; b) cloning part of the gene into an RNA interference construct and expression of this construct in transgenic plants; or c) mutagenesis by various methods (including Targeting Induced Local Lesions IN Genomes (TILLING) and tDNA insertion mutagenesis) followed by screening by PCR or other methods for an aromatic variant.

The present invention further provides a transgenic plant having an elevated level of the compound 2-acetyl-1-pyrroline compared to its level in a control non-transgenic plant wherein the level of the compound is increased in the transgenic plant by reducing the mRNA or protein levels encoded by the Os2AP gene or genes encoding homologs of Os2AP in the transgenic plant compared to the mRNA or protein levels encoded by the Os2AP gene or genes encoding homologs of Os2AP in the control non-transgenic plant. In one format, the mRNA and protein levels are reduced by RNA interference or by antisense. The invention is further directed to transgenic seed produced from the transgenic plants of the invention.

Although the examples to follow describe experiments performed in rice, the invention relates to other plants and fungi, including but not limited to wheat, barley, rye, coconut, sorghum, soybean, and oats.

Another aspect of the present invention provides methods for increasing aromatic fragrance in transgenic plants by increasing the level of the compound 2-acetyl-1-pyrroline in a transgenic plant compared to its level in a control, non-transgenic plant by reducing the level of an mRNA in the plant, wherein the mRNA is encoded by the Os2AP gene or genes encoding homologs of Os2AP and wherein the mRNA level is reduced by expression of the nucleic acid in an antisense orientation, or by expression of an RNA interference (RNAi) construct comprising at least a fragment of 20 contiguous nucleotides of the nucleic acid. The methods further comprise the step of screening the resulting plants for an increase in popcorn-like aroma or for an increase in the compound 2-acetyl-1-pyrroline relative to the control, non-transgenic plant. In some embodiments the mRNA level of the nucleic acid is reduced by expressing the nucleic acid in the antisense orientation. In some embodiments the mRNA level of the nucleic acid is reduced by expressing the nucleic acid in an RNA interference (RNAi) construct.

The present invention further provides an isolated nucleic acid encoding the Os2AP gene, where said nucleic acid includes a nucleic acid which hybridizes to the nucleic acid sequence depicted in SEQ ID NO: 1, SEQ ID NO: 2, SEQ ID NO: 4 or SEQ ID NO: 5 or its complement under hybridization conditions that include at least one wash in 0.1×SSC and 0.1% SDS at 60-65° C. for thirty minutes, a nucleic acid which is at least 70% identical, 80% identical, 90% identical, 95% identical, or greater than 95% identical to the sequence depicted in SEQ ID NO: 1, SEQ ID NO: 2, SEQ ID NO: 4 or SEQ ID NO: 5, and a nucleic acid that encodes a polypeptide that is at least 70%, at least 80%, at least 90%, at least 95%, or greater than 95% identical to the amino acid sequence depicted in SEQ ID NO: 3 or SEQ ID NO: 6.

The amount of 2-acetyl-1-pyrroline in rice can vary depending on harvest conditions and soil type. A non-aromatic variety, Nipponbare, has 2-acetyl-1-pyrroline levels in the range of 0 to 0.1 ppm (parts per million). In contrast an aromatic rice variety, That Hom Mali, has an amount of 2-acetyl-1-pyrroline in the range of 1 to 2.5 ppm. Example 2 details an RNA interference experiment against the rice Os2AP gene, which increased the 2-acetyl-1-pyrroline levels in Nipponbare rice up to 2.5 ppm. The present invention thus provides methods for increasing the level of fragrance in a non-aromatic plant to aromatic levels.

The present invention further provides an isolated nucleic acid encoding the GmAMADH2 gene, where said nucleic acid includes a nucleic acid which hybridizes to the nucleic acid sequence depicted in SEQ ID NO:97, SEQ ID NO:98, SEQ ID NO:100 or SEQ ID NO:101 or its complement under hybridization conditions that include at least one wash in 0.1×SSC and 0.1% SDS at 60-65° C. for thirty minutes, a nucleic acid which is at least 70% identical, 80% identical, 90% identical, 95% identical, or greater than 95% identical to the sequence depicted in SEQ ID NO:97, SEQ ID NO:98, SEQ ID NO:100 or SEQ ID NO:101 and a nucleic acid that encodes a polypeptide that is at least 70%, at least 80%, at least 90%, at least 95%, or greater than 95% identical to the amino acid sequence depicted in SEQ ID NO:99 or SEQ ID NO:102.

The amount of 2-acetyl-1-pyrroline in soybean can vary depending on harvest conditions and soil type. A non-aromatic variety, Chiang Mai 60, has undetectable levels of 2-acetyl-1-pyrroline. In contrast an aromatic soybean variety, Chamame, has an amount of 2-acetyl-1-pyrroline in the range of 579.5±28.8 ppm (parts per million). Example 10 details an RNA interference experiment against the soybean GmAMADH gene, which increased the 2-acetyl-1-pyrroline levels in Chiang Mai 60 up to 324.2±45.2 ppb. The present invention thus provides methods for increasing the level of fragrance in a non-aromatic plant to aromatic levels.

The invention further provides recombinant constructs and expression vectors containing the nucleic acids of the invention, where the nucleic acid can be operably linked to a promoter. One useful promoter is a cauliflower mosaic virus (CaMV) promoter, which confers high levels of expression in most plant tissues. The ubiquitin promoter, another strong promoter, also confers high levels of expression in monocot species.

The invention further provides host cells that contain the nucleic acids, constructs, and expression vectors of the invention.

The invention also provides methods for screening plants and nucleic acids for a mutation in an Os2AP gene leading to a decrease in Os2AP protein expression or activity and a consequent increase in aroma resulting from increased production of the 2-acetyl-1-pyrroline compound. One specific mutation is an eight nucleotide deletion associated with an aromatic phenotype in the rice Os2AP gene. Screening for this and other mutations can be done by a variety of methods, such as PCR, sequencing, hybridization, or microarray experiments. Another option is to look for the reduction of Os2AP protein levels or a change in structure or activity of the Os2AP protein. This could be done, for example, by using an antibody which binds to the active Os2AP protein, or by an assay for Os2AP protein activity.

The invention further provides a non-naturally occurring plant where SEQ ID NO: 101 is overexpressed. Overexpression may be achieved by any method known in the art.

The sequences described herein can be used as probes or primers in nucleic acid hybridization experiments. Nucleic acid segments that include at least a 14 nucleotide long contiguous sequence that has the same sequence as, or is complementary to, a 14 nucleotide long contiguous DNA segment of the nucleotide sequence depicted in SEQ ID NO: 1, SEQ ID NO: 2, SEQ ID NO: 4 or SEQ ID NO: 5 can be used. SEQ ID NO:97, SEQ ID NO:98, SEQ ID NO:100 or SEQ ID NO:101.

Longer contiguous identical or complementary sequences, e.g., those of about 20, 30, 40, 50, 100, 200, 500, 1,000, 2,000, 5,000, 10,000 etc. (including all intermediate lengths and up to and including full-length sequences will also be of use in certain embodiments.

The ability of such nucleic acid probes to specifically hybridize to sequences of the Os2AP gene and genes encoding homologs of Os2AP will enable them to be of use in detecting the presence of complementary sequences in a given sample.

However, other uses are envisioned, including the use of the sequence information for the preparation of mutant species primers, or primers for use in preparing other genetic constructions.

Figure 2:
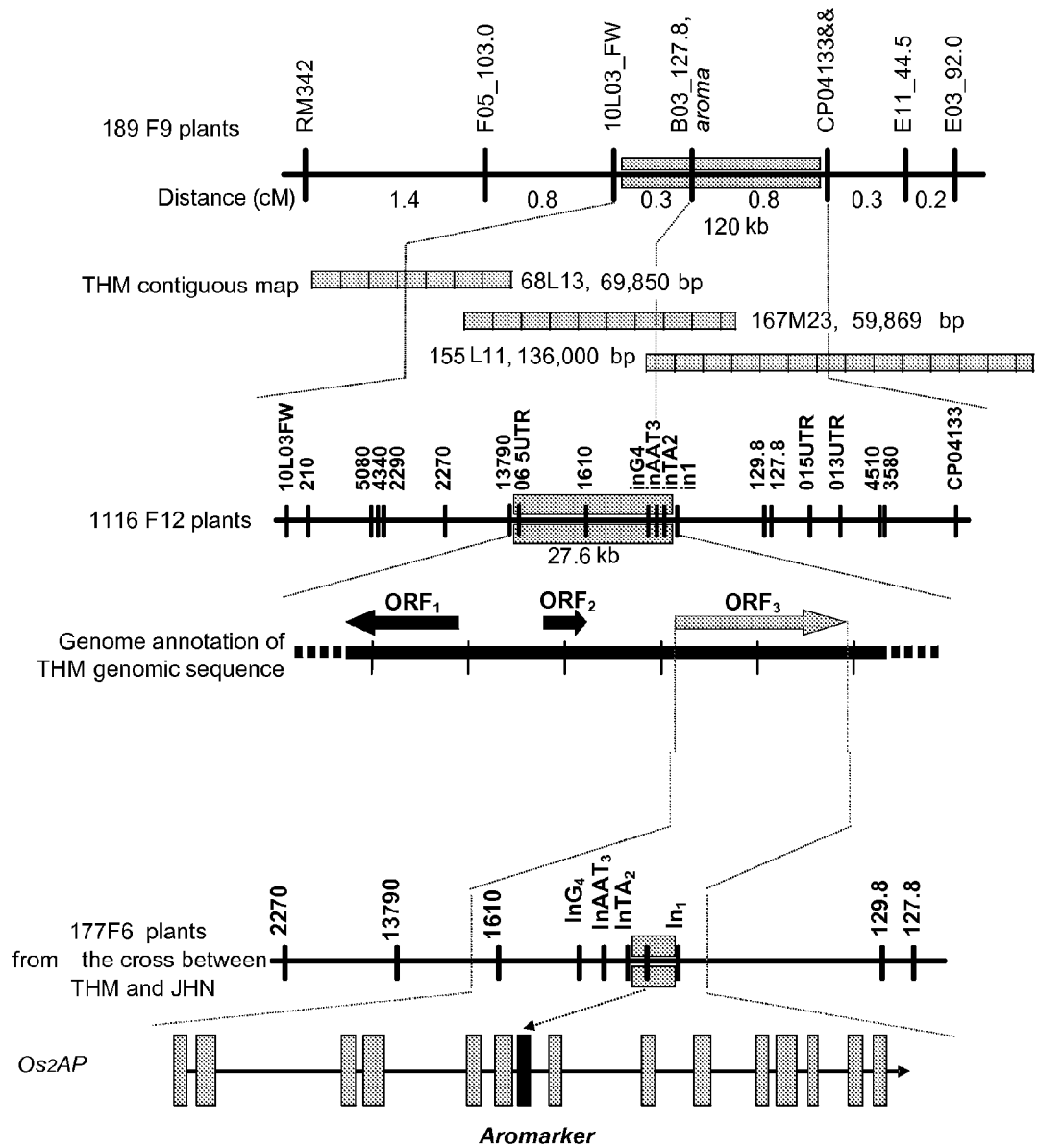
FIG. 2 depicts fine-scale mapping of the aroma gene in rice using 186 F9 plants derived from a single F6 plant segregating for grain aroma and the construction of a physical map encompassing the gene for grain aroma.

The first part of FIG. 2 shows the graphical genotypes of eight F11 plants from the single F6 plant. The second part shows ultrascale mapping using 1116 F12 plants derived from a single F6 plant to narrow down the critical region to 27 kb in a single BAC. The third part shows the annotation of genomic sequence from KDML105 which revealed three open-reading frames. The fourth part shows that using 177 F6 plants from the cross between KDML105 and JHN identified three double recombinants within exon 7 of the unknown protein gene that significantly affects grain aroma and 2-acetyl-1-pyrroline contents. The unknown protein gene was named Os2AP. "Aromarker" is the PCR-based marker defining the 8 base pair deletion and 3 SNPs (single nucleotide polymorphisms) specific to grain aroma.

Figure 3A:
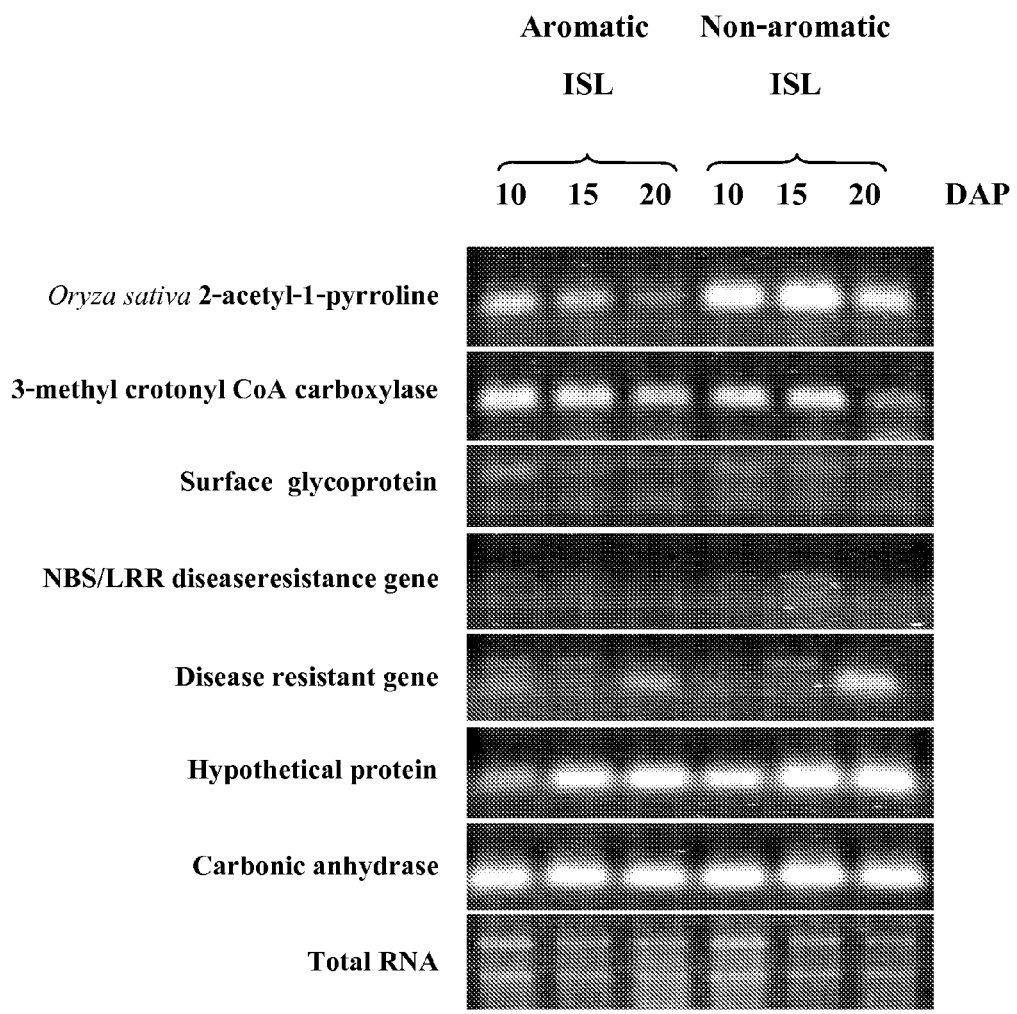

FIG. 3A depicts expression of seven candidate genes using RT-PCR from total RNA isolated from 10, 15 and 20 days after pollination between aromatic and non-aromatic isogenic lines.

Figure 3B:
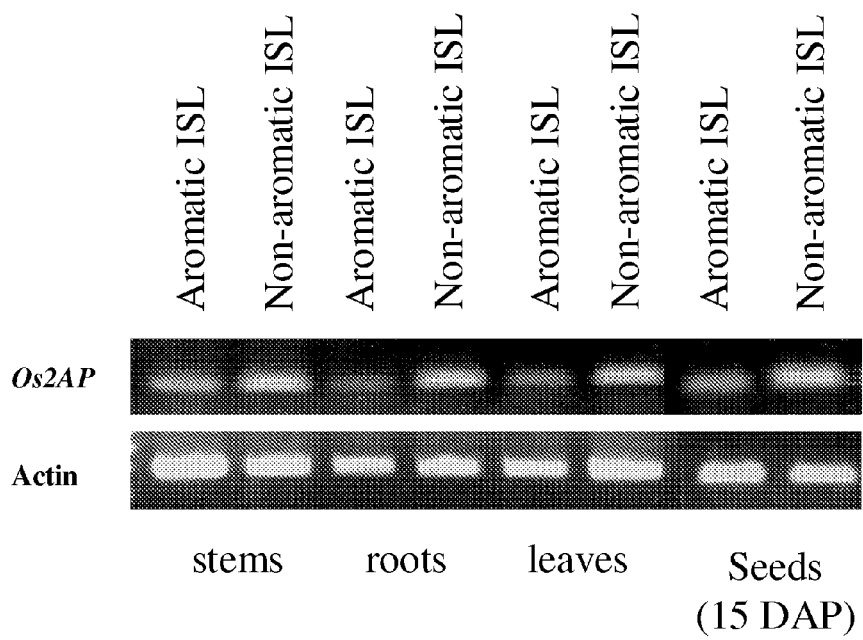

FIG. 3B depicts differential expression of Os2AP transcripts in leaves, stems and roots from total RNA isolated 15 days after pollination between aromatic and non-aromatic isogenic lines.

Figure 3C:
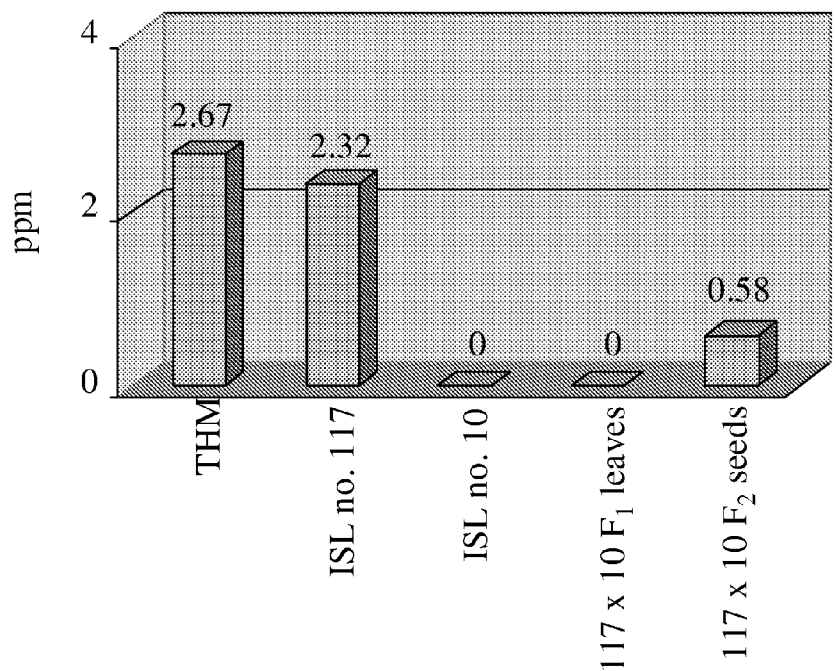

FIG. 3C depicts analysis of 2-acetyl-1-pyrroline levels in grains of THM (KDML105), aromatic isogenic line 117, non-aromatic isogenic line 10, and their F2 (ISL117×ISL10). In F1, analysis of 2-acetyl-1-pyrroline levels was conducted in leaves.

Figure 3D:
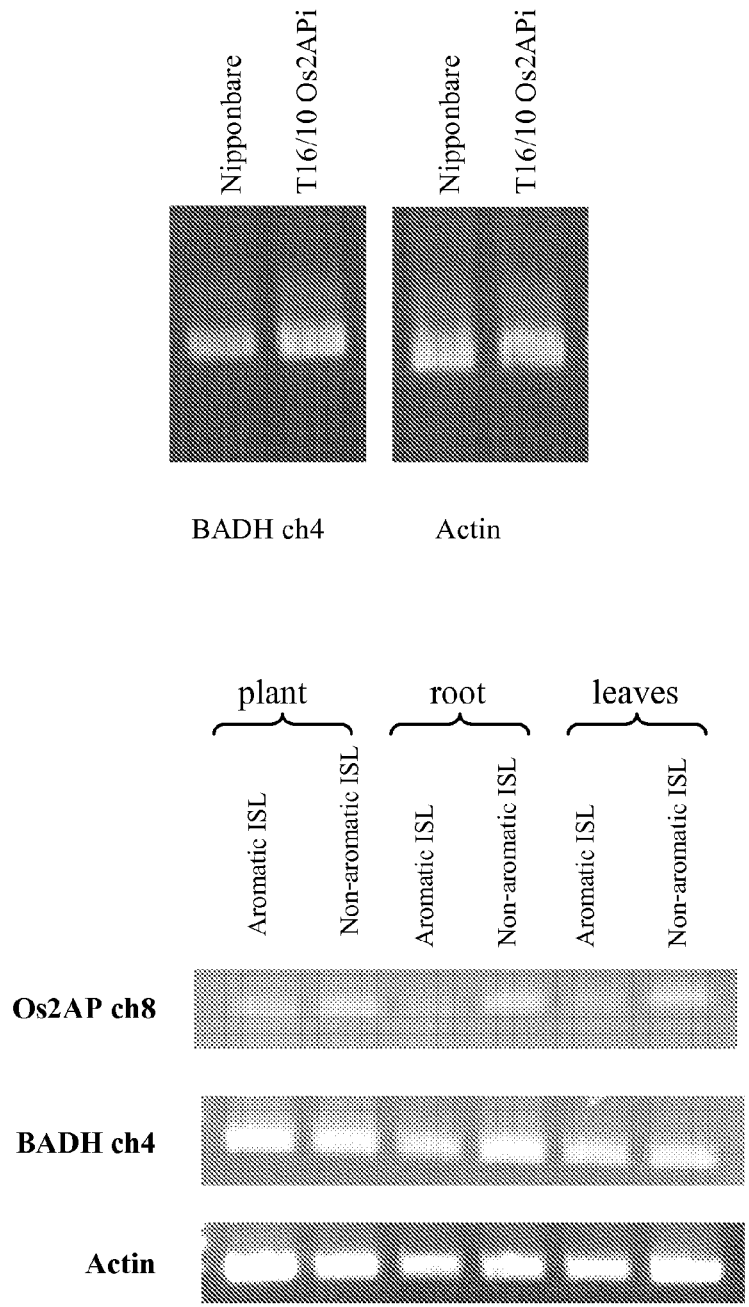

FIG. 3D, upper panel, depicts expression of the BADH gene from chromosome 4 and actin in transgenic Nipponbare carrying the Os2AP RNAi construct. FIG. 3D, lower panel, depicts the Os2AP gene on chromosome 8, not the BADH gene on chromosome 4, showing differential expression in aromatic and non-aromatic isogenic lines of rice.

Figure 4A:
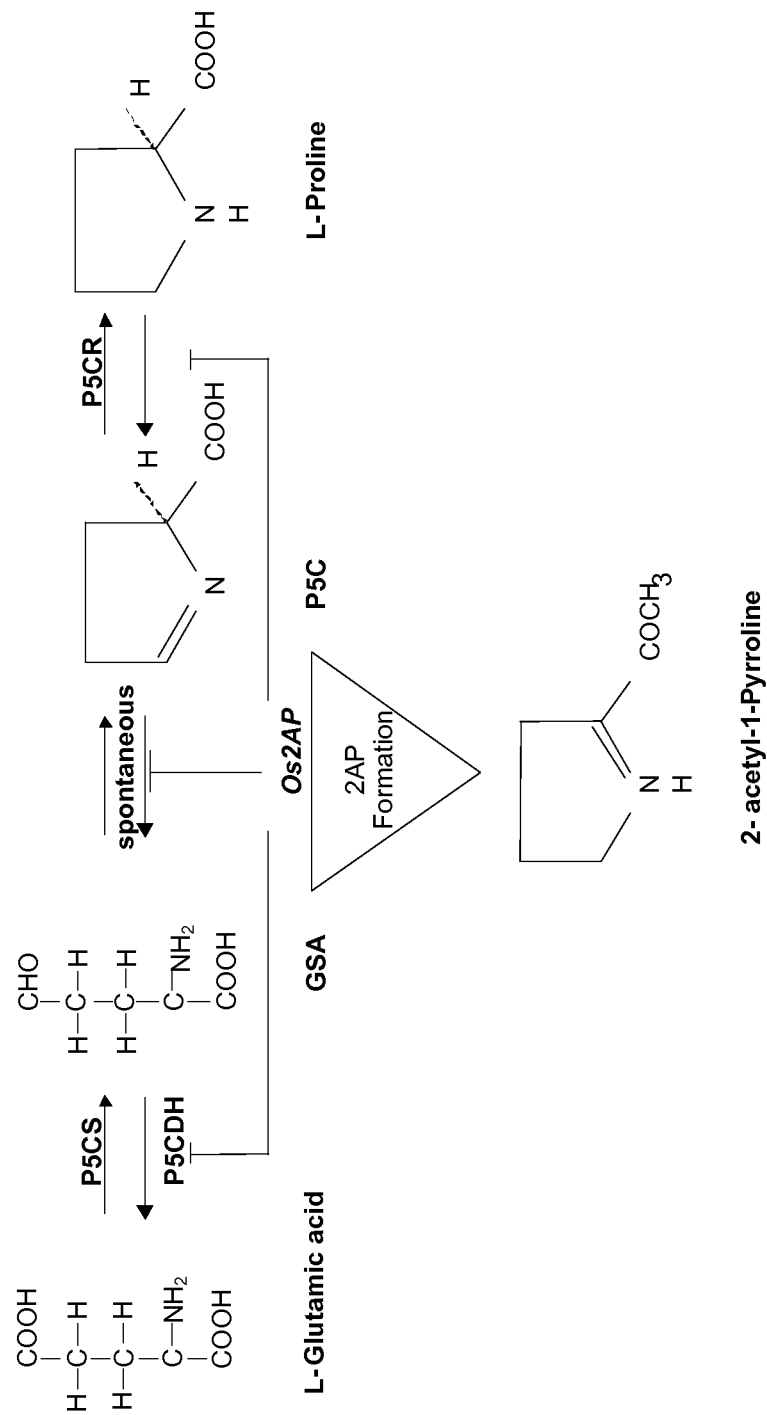

FIG. 4A shows the polyamine metabolic pathway leading ornithine, putrescine or spermidine to GBAL, the precursor of 1-pyrroline and GABA. The proposed metabolic shift was mediated by nonsense mutation of the Os2AP gene.

Figure 4B:
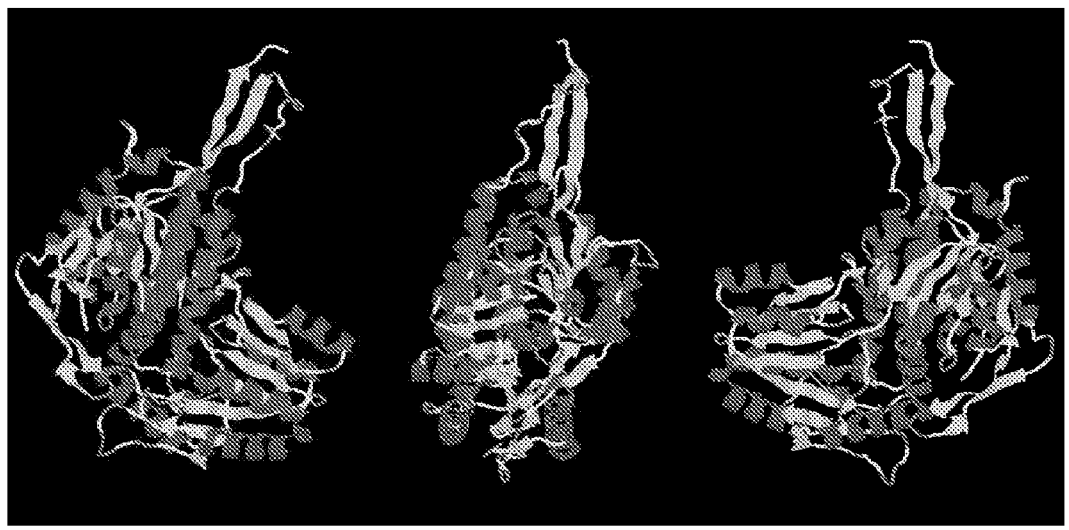

FIG. 4B shows the predicted protein structure of the Os2AP enzyme created by using RASMOL, a program available through the website of the Microbiology Department of the University of Massachusetts, Amherst, USA (new version is Protein Explorer).

FIG. 5A-C shows the genomic sequence comparison of Os2AP genes from KDML105 (aromatic) and Nipponbare (non-aromatic).

FIG. 5D depicts a DNA alignment showing an eight base pair deletion in Os2AP in an aromatic strain, That Hom Mali (THM) as compared to Nipponbare, a non-aromatic strain, and the amino acid sequence comparison between the two strains. The nucleotide sequences in the alignment include nucleotides 701 to 765 from SEQ ID NO: 5 and nucleotides 701 to 757 from SEQ ID NO: 2.

Figure 6:
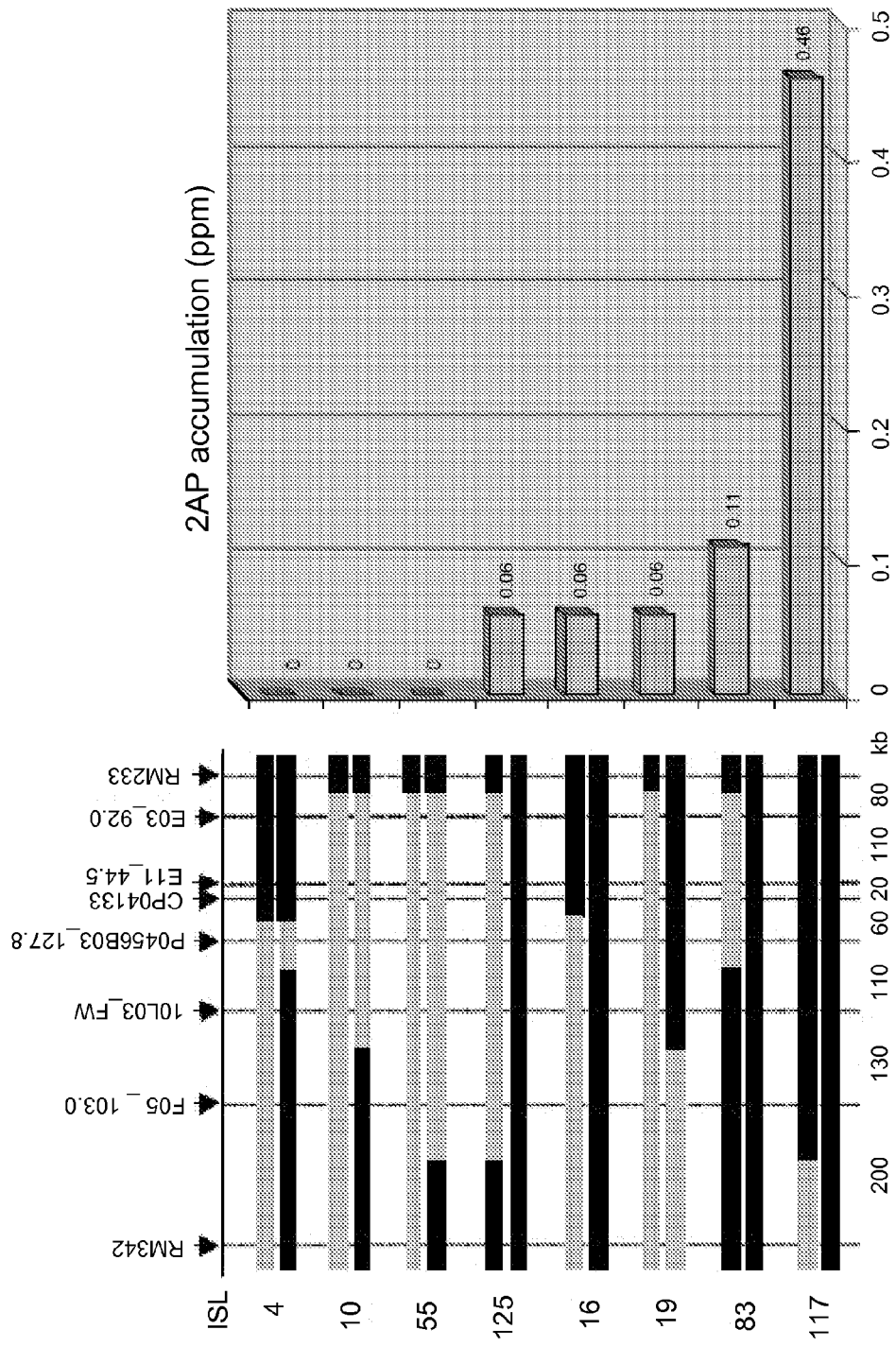

FIG. 6 depicts graphical genotypes of eight F11 plants from the single F6 plant and the analysis of 2-acetyl-1-pyrroline levels from the rice grains.

Figure 7A:
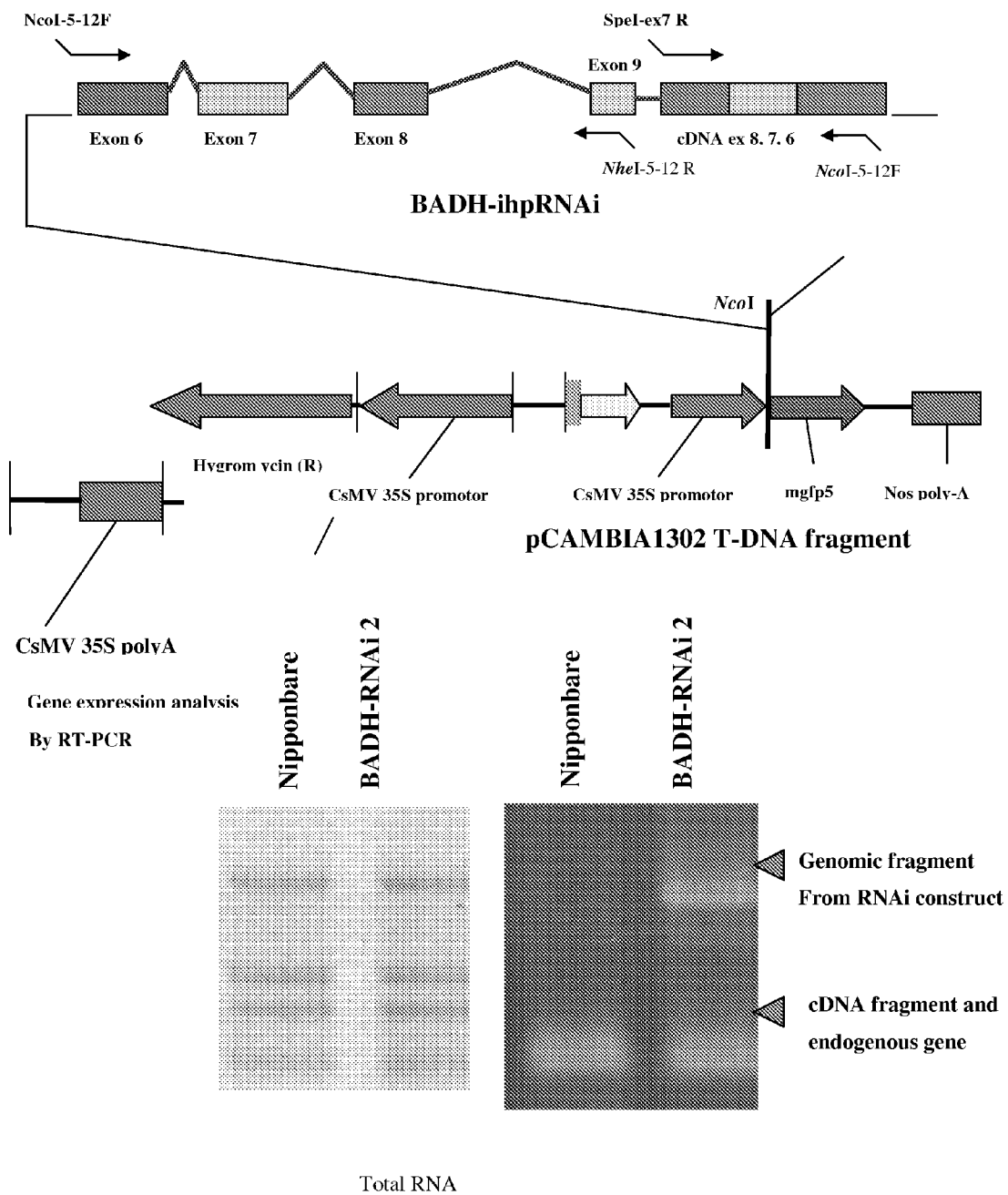

FIG. 7A depicts an RNA interference construct and vector for transformation. The lower panel shows confirmation of expression of the construct.

Figure 7B:
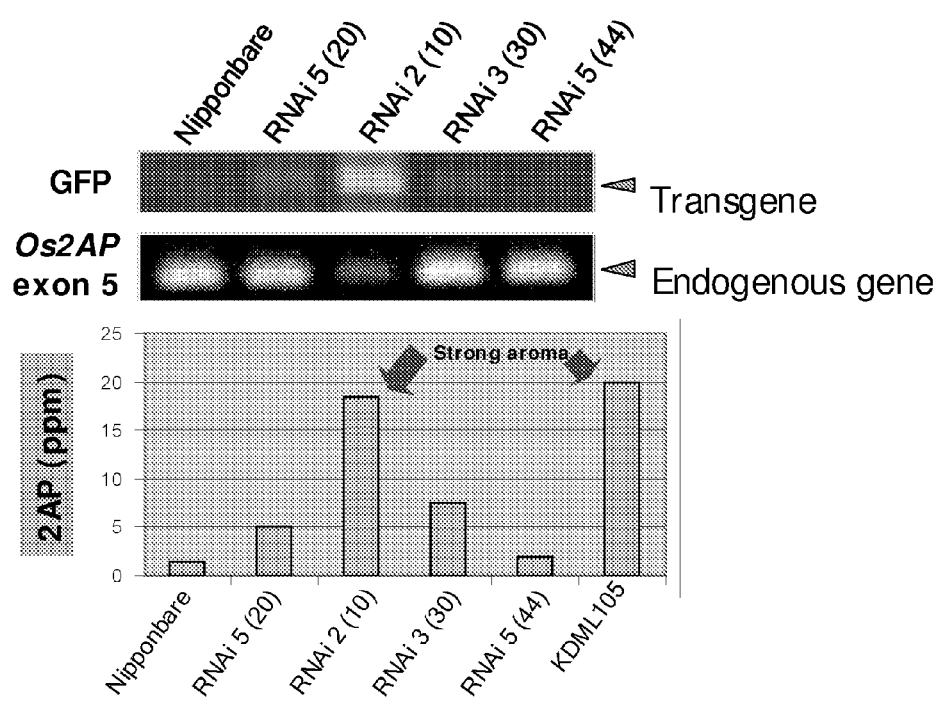

FIG. 7B depicts expression of the RNAi construct, GFP, and the endogenous Os2AP. The lower panel shows 2-acetyl-1-pyrroline levels and aroma. Os2AP-RNAi2 is an RNAi construct against the Os2AP gene.

Figure 8A:
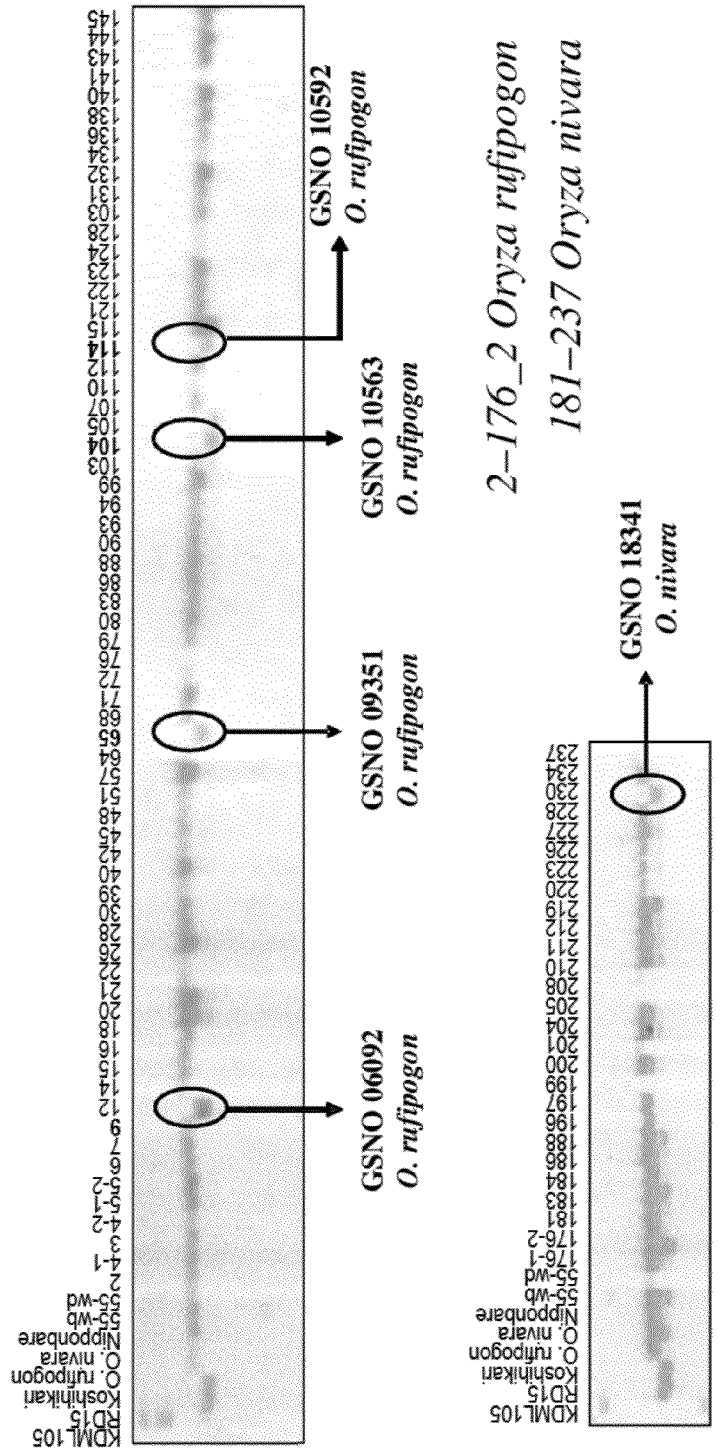

FIG. 8A depicts the results from screening F6 progeny for the Os2AP variant correlated with increased aroma using the "Aromarker" primer set.

Figure 8B:
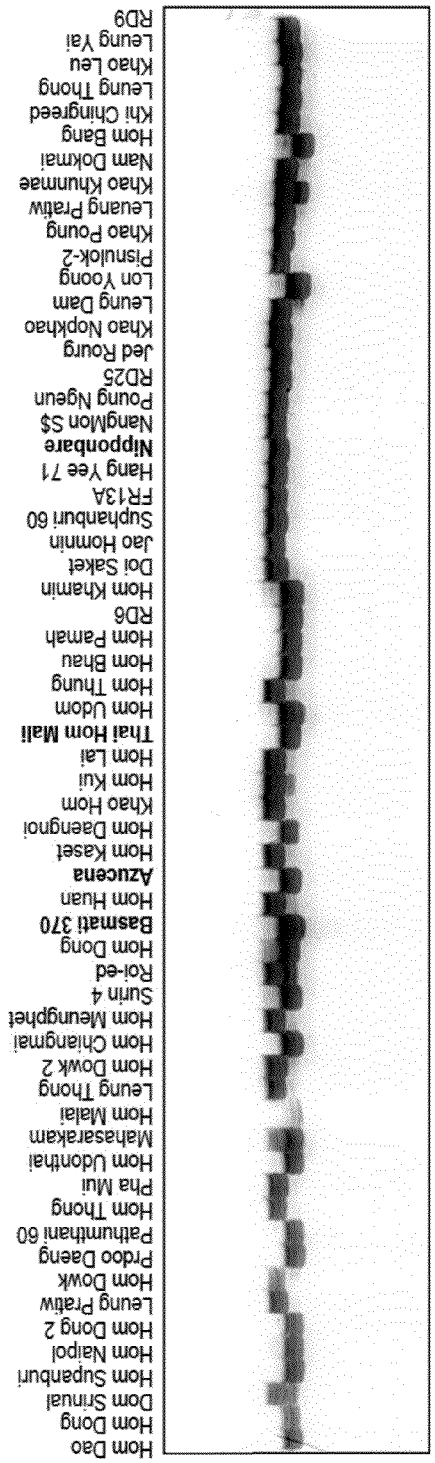

FIG. 8B depicts the results from screening various varieties of rice for the aromatic Os2AP allele.

FIG. 9A shows the DNA sequences of the Os2AP orthologs from various strains of rice. The nucleotide sequences in the alignment include nucleotides 701 to 765 from SEQ ID NO: 5 and nucleotides 701-757 from SEQ ID NO: 2, SEQ ID NO: 5, and SEQ ID NOS: 89-95.

Figure 9B:
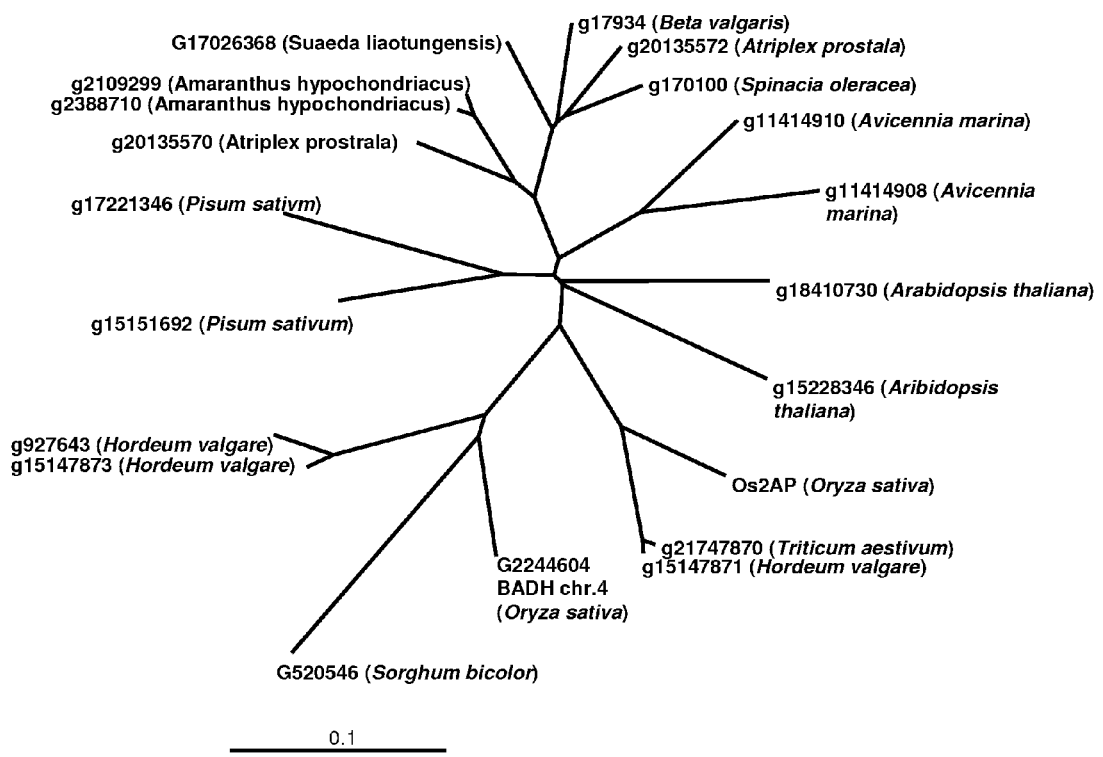

FIG. 9B shows the phylogenetic tree constructed using Neighbor-Joint tree of 22 orthologs of BADH and Os2AP.

Figure 10:
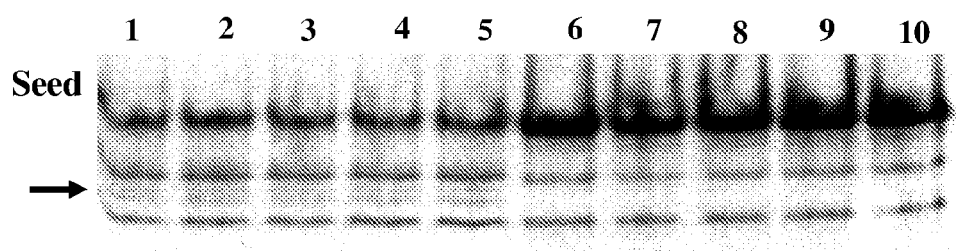

FIG. 10 shows AMADH activity assay on a PAGE gel of partially-purified enzymes extracted from vegetable soybean seeds. Lane 1 (Okuhara wase), lane 2 (Oishi Edamame), lane 3 (Shirono Mai), lane 4 (Chiang Mai 60) and lane 5 (Jack) contain non-aromatic varieties. Lane 6 (Chamame), lane 7 (Kouri), 8 (Kaori Hime), lane 9 (Fukunari) and lane 10 (Yoagari musume) contain aromatic varieties. The arrow indicates the candidate AMADH activity band that is different between aromatic and non-aromatic vegetable soybean seeds.

Figure 11:
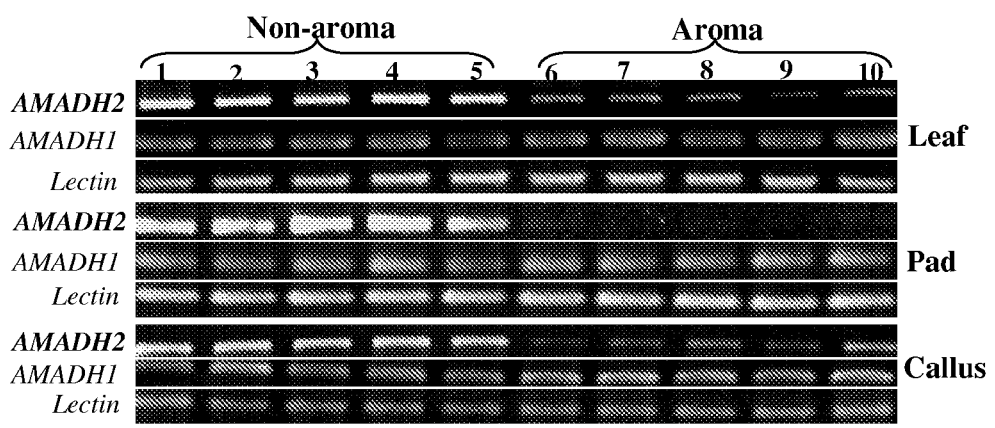

FIG. 11 shows RT-PCR analysis of GmAMADH1 and GmAMADH2 expression identified in leaves, young seeds, and callus tissues of non-aromatic and aromatic vegetable soybean varieties. The Lectin gene was used as control.

FIG. 12 shows (a) the gene structure of GmAMADH2 and the sequence variation in exon 10. The rectangles represent exons and the gray bars represent introns. The TT deletion at nucleotide 928 and 929 is indicated. The [NA] fragment is set forth as SEQ ID NO:103, and the [A] fragment is set forth as SEQ ID NO:104. Part (b) shows the in silico translation of the GmAMADH2 coding sequence (SEQ ID NO:98) from the start codon (ATG). The premature stop codon (TAG) is indicated with an asterisk. The amino acid sequence of the Chamame GmAMADH2 protein is set forth as SEQ ID NO:99.

Figure 13:
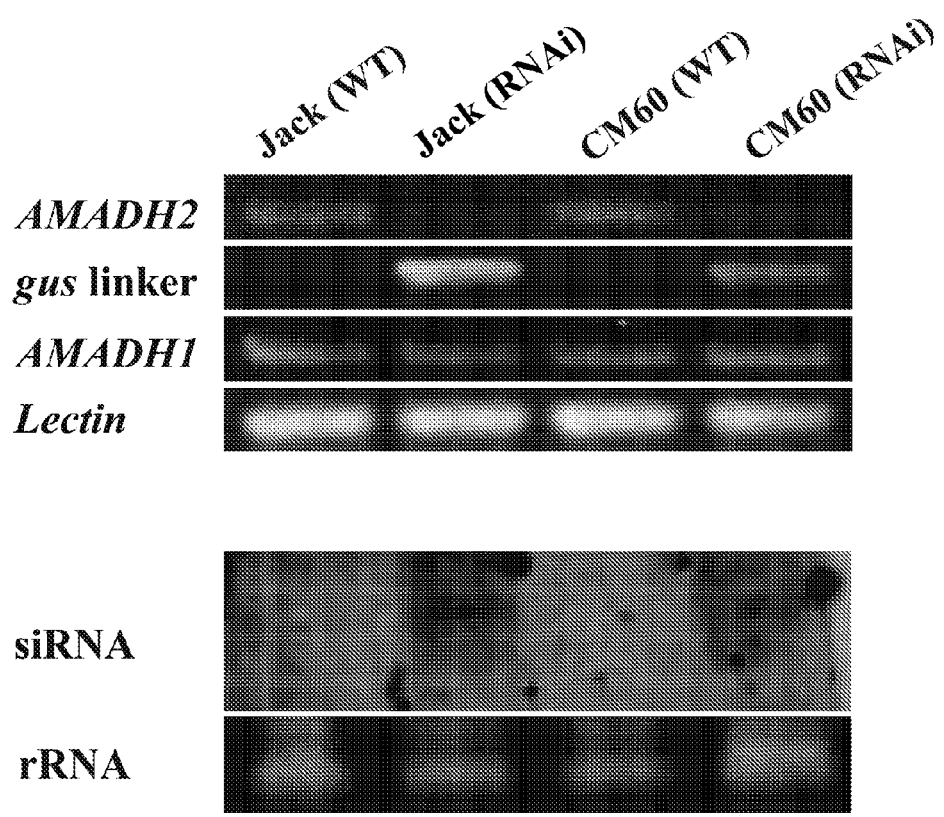

FIG. 13 shows (a) RT-PCR analysis of endogenous GmAMADH2, the transgene (gus linker), and GmAMADH1 among the wild type varieties Jack and CM60 and their RNAi lines, Jack-RNA1 and CM60-RNAi, respectively. The Lectin gene was used as control. Part (b) shows an RNA gel blot of the siRNA specific to the GmAMADH2 probe in the wild type varieties Jack and CM60 and their RNAi lines, Jack-RNA1 and CM60-RNAi, respectively. rRNA was used to determine the amount of RNA in the four samples.

Figure 14:
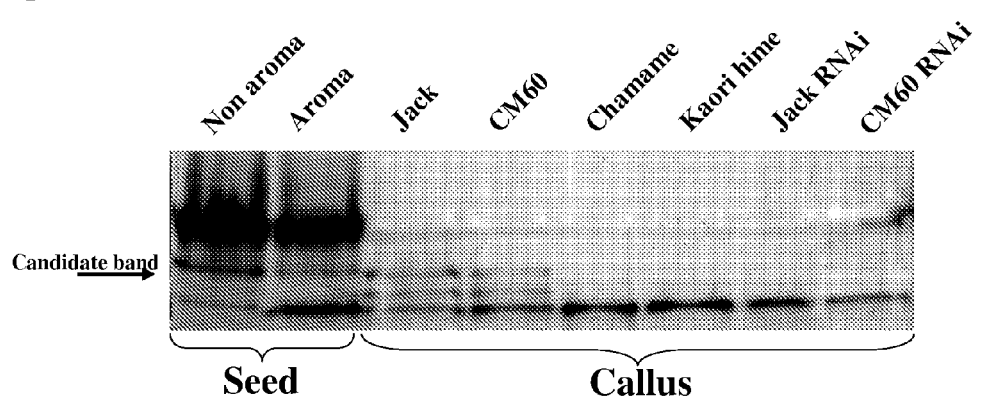

FIG. 14 shows an AMADH gel activity assay of the partially-purified enzymes in callus tissues of the wild type species Jack and CM 60 and their RNAi lines, Jack RNAi and CM 60 RNAi, respectively. The varieties Chamame and Kaori hime were used as aromatic line controls for the enzyme activity in callus tissues. The varieties Okahara and Kaori hime were used as non-aromatic and aromatic lines controls, respectively, for the enzyme activity in seeds.

FIG. 15 shows (a) a phylogenetic tree of BADH homologs among higher plants, including *Pisum sativum* (CAC48392.2_PISSA and CAC48393.1_PISSA), *Zoysia tenuifolia* (BAD34953.1_ZOYTE and BAD34949.1_ZOYTE), *Oryza sativa* (Os04g0464200_ORYSA and Os08g0424500_ORYSA), *Zea mays* (ACF87737.1_ZEAMA and NP_001105781.1_ZEAMA), *Sorghum bicolor* (Sb07g020650.1_SORBI and Sb06g019200.1_Sb06g019210.1_SORBI), *Arabidopsis thaliana* (At3g48170.1_ARATH and At1g74920.1_ARATH), *Populus trichocarpa* (661953_POPTR and 666405_POPTR), *Glycine max* (BAG09376.1_GLYMA and BAG09377.1_GLYMA), *Amaranthus hypochondriacus* (AAB58165.1_AMAHY and AAB70010.1_AMAHY), *Atriplex hortensis* (ABF72123.1_ATRHO and P42757.1_ATRHO), and *Hordeum vulgare* (BAB62846.1_HORVU and BAB62847.1_HORVU); a Lycophyte (Selaginella moellendorffii; 24394_CHLRE), a Chlorophyte genome (*Chlamydomonas reinhardtii;* 174224_SELMO), and a Bryophyte genome (*Physcomitrella patens; EDQ*78577.1_PHYPA). The bootstrap values are indicated at the branch points. Part (b) shows consensus sequences of the aldehyde dehydrogenase cysteine active site domain contained in all BADH homologous proteins. The BADH homologs were grouped as monocotyledonous (SEQ ID NOS:105-108), dicotyledonous (SEQ ID NOS:105, 110 and 111), and primitive classes (SEQ ID NOS:105 and 109). The two subgroups of the monocotyledonous class are separated from each other. The cysteine active site is in the middle of each sequence. The regular pattern of the aldehyde dehydrogenase cysteine active site domain from Prosite was provided (SEQ ID NO:112).

Figure 16:
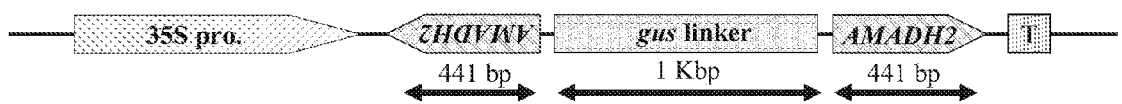

FIG. 16 shows the structure of the pANGmAMADH2 RNAi vector. The two fragments in sense and antisense directions were taken from the genomic sequence of GmAMADH2 including exon 1, intron 1, and part of exon 2. The gus linker fragment interrupting the gene fragments was serves as a loop. The 35S promoter and terminator flank either side of the construct.

Figure 17:
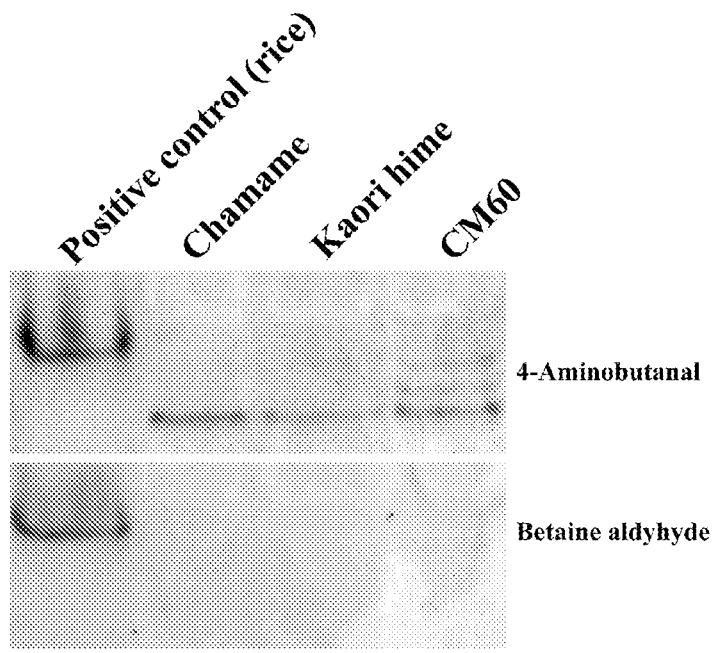

FIG. 17 shows a substrate-specific test with 4-aminobutanal and betaine aldehyde of enzyme extracts from soybean and rice calli. The positive control is the non-aromatic rice c.v. Nipponbare. Chamame and Kaori hime represent aromatic varieties and CM60 represents a non-aromatic variety of soybean.

BRIEF DESCRIPTION OF SOME OF THE SEQUENCES IN THE SEQUENCE LISTING

SEQ ID NO: 1 is the genomic nucleotide sequence of the Os2AP gene from an aromatic rice strain, That Hom Mali.

SEQ ID NO: 2 is the protein-encoding nucleotide sequence of That Hom Mali Os2AP.

SEQ ID NO: 3 is the amino acid sequence of the That Hom Mali Os2AP protein.

SEQ ID NO: 4 is the genomic nucleotide sequence of the Os2AP gene from a non-aromatic rice strain, Nipponbare.

SEQ ID NO: 5 is the protein-encoding nucleotide sequence of Nipponbare Os2AP.

SEQ ID NO: 6 is the amino acid sequence of Nipponbare Os2AP protein.

SEQ ID NO: 7 through 88 are primers which can be used to amplify portions of the Os2AP nucleotide sequence, GFP, or actin. (TABLE 1).

SEQ ID NO: 89 through 95 are sequences of fragments of Os2AP gene orthologs.

SEQ ID NO: 96 is the decapeptide which is highly conserved among general aldehyde dehydrogenases.

SEQ ID NO: 97 is the genomic nucleotide sequence of the GmAMADH2 gene from an aromatic soybean strain, Chamame.

SEQ ID NO: 98 is the protein-encoding nucleotide sequence of Chamame GmAMADH2.

SEQ ID NO: 99 is the amino acid sequence of the Chamame GmAMADH2 protein.

SEQ ID NO: 100 is the genomic nucleotide sequence of the GmAMADH2 gene from non-aromatic soybean strain, CM60.

SEQ ID NO: 101 is the protein-encoding nucleotide sequence of CM60 GmAMADH2.

SEQ ID NO: 102 is the amino acid sequence of the CM60 GmAMADH2 protein.

DETAILED DESCRIPTION OF THE INVENTION

The invention relates to Os2AP genes and genes encoding homologs of Os2AP. Nucleic acid sequences from these genes are used to enhance the levels of 2-acetyl-1-pyrroline, a major aromatic compound found in rice, wheat, maize, oat, pandan leaf, aromatic coconut, aromatic vegetable soybean, and some bacteria and fungi.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols in Molecular Biology (F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) Current Protocols in protein Science (John Wiley & Sons, Inc.); the series Methods in Enzymology (Academic Press, Inc.): PCR 2: A Practical Approach (M. J. MacPherson, B. D. Hames and G. R. Taylor eds. (1995), Harlow and Lane, eds. (1988) Antibodies, a Laboratory Manual, and Animal Cell Culture R. I. Freshney, ed. (1987).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-

569-8); Ausubel et al. (1987) Current Protocols in Molecular Biology, Green Publishing; Sambrook et al. (1989) Molecular Cloning: A Laboratory Manual, Cold Spring Harbor, N.Y. Definitions of common terms in plant biology may be found in Esau, Plant Anatomy, published by John Wiley & Sons (1977) (ISBN 0-471-24520-8); and Solomon et al., Biology, published by Saunders College Publishing (1993).

Definitions

In order to facilitate review of the various embodiments of the invention, the following definitions are provided:

Os2AP polynucleotide sequences: The genes according to the subject invention include not only the full-length sequences disclosed herein but also fragments of these sequences, which retain the characteristic activity of the sequences specifically exemplified herein.

The rice Os2AP gene sequence is disclosed herein. The rice Os2AP gene sequence is also known as OsBADH2. It is apparent to a person of skill in this art that Os2AP polynucleotide sequences from another plant can be readily identified and obtained through several means using the rice Os2AP gene sequence. These means include, for example, identifying orthologs of the protein encoded by rice Os2AP and isolating the nucleotide sequences that encode such homologous proteins. The specific genes, or portions thereof, may be obtained from a culture depository, or constructed synthetically, for example, by use of a gene machine. In general, Os2AP polynucleotide sequences encode aldehyde dehydrogenase enzymes.

Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Various enzymes may be used to directly obtain active fragments of these Os2AP polynucleotide sequences.

Equivalent Os2AP polynucleotide sequences and/or genes encoding these equivalent Os2AP polynucleotide sequences can also be isolated from strains and/or DNA libraries using the teachings provided herein. For example, antibodies to the Os2AP proteins disclosed herein can be used to identify and isolate other Os2AP proteins from a mixture of proteins. Specifically, antibodies may be raised to the portions of the Os2AP proteins which are most constant and most distinct from other proteins. These antibodies can then be used to specifically identify equivalent Os2AP proteins with the characteristic activity by immunoprecipitation, enzyme linked immunoassay (ELISA), or Western blotting.

A further method for identifying the genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying genes of the subject invention. Exemplary probes are described in Table 1.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed are due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the Os2AP proteins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of an Os2AP polynucleotide sequence encoding a gene of the invention. Such mutants can be made by techniques well known to persons skilled in the art. For example, UV irradiation can be used to prepare mutants of host organisms, tDNA insertion mutagenesis can be used, or TILLING (Targeted Induced Local Lesion of Genome) can be used. Likewise, such mutants may include asporogenous host cells which also can be prepared by procedures well known in the art.

Os2AP polynucleotide sequences, including those from rice, may be obtained using the PCR primers of the invention. These primers are shown in TABLE 1, and correspond to the sequences depicted in SEQ ID NO: 7 through SEQ ID NO: 79 and SEQ ID NO: 88 through SEQ ID NO: 100. Combinations of these primers may be used to amplify different regions of the Os2AP genes. PCR conditions which work for this amplification are as follows: 10 μL reaction mixture with 10 ng of template DNA, 0.1 mM dNTP, 0.5 (M of each primer, 0.5 unit of Taq polymerase, 2.0 mM MgCl2, and 1× Thermophilic Polymerase Buffer (Promega). This mixture should undergo 30 cycles of PCR with the following times and temperatures: 94° C. for 30 seconds (denaturation), 60° C. for 30 seconds (annealing), and 72° C. for 2 min (extension).

TABLE 1

List of primers

| SEQ ID NO: | Primer name | Sequence (5'→3') |
|---|---|---|
| 7 | OS2AP-8L | GCCATGCCAACTGAGTAAAG |
| 8 | OS2AP-8R | CAATTTTATTCGCTCTGTGC |
| 9 | OS2AP-9L | TGCAACATCGCGTCTTATTC |
| 10 | OS2AP-9R | GCAACTAGCAAGAGCATACACC |
| 11 | OS2AP-12L | ACCTGACATCATGCCTTTGG |
| 12 | OS2AP-12R | CCGGTCATCAGCTAACTTCC |
| 13 | OS2AP-13R | CCCTTCGTCATAAAATATACTAGCAA |
| 14 | OS2AP-14L | TCCTCCAACATGCTCTTTCG |
| 15 | OS2AP-14R | CAGAGAAGTTTACGCCGTTG |
| 16 | OS2AP-15L | TTTTTAAATAAGATGAACGGTCAAA |
| 17 | OS2AP-16L | CTCTCCACCCTCTGCTTCTG |
| 18 | OS2AP-16R | CTCTCCGCTTGAACCCATC |
| 19 | OS2AP-17L | GCATGGCTGATTGTGTATCTG |
| 20 | OS2AP-17R | TTCCAAACCTACGGACAAAAG |
| 21 | OS2AP-18L | TTCCTCTTCTCTTGTGCAAAC |
| 22 | OS2AP-18R | CACGGAAGCCAATTCAGATG |
| 23 | OS2AP-19L | CTATCCTCTCCTGATGGCAAC |
| 24 | OS2AP-19R | TGGCTACTAGAATGATGCTCAAAG |
| 25 | OS2AP20L | CCTTTTGTGTCGCTTTTGAG |
| 26 | OS2AP20R | AAAATAGCCTTCACTCGTTGC |
| 27 | OS2AP21L | CCATCGATTTCGAGGGTAAC |
| 28 | OS2AP21R | CGCATCCGATAATATGTTG |
| 29 | OS2AP22L | GTAATTAGGAGTACGACTCTCGTC |
| 30 | OS2AP22R | GCTTATAGCCTACTGTATCCTCCTC |
| 31 | OS2AP23L | AATTGGTTAACCCAGCAAGC |
| 32 | OS2AP23R | ACATTGTGAAACGGAGGAAG |
| 33 | OS2AP24L | GCTATAAGCCAGCTGCAAAC |
| 34 | OS2AP24R | GCAGTTGGTACGGACTTCG |
| 35 | OS2AP25L | CCTAAATATTTGACGCCGTTG |
| 36 | OS2AP25R | TGAAGAGGAGGGTACCGATG |
| 37 | OS2AP26L | CACCACTCCACACCTGACAC |
| 38 | OS2AP26R | GTACGGAACACACGCACAAG |

TABLE 1-continued

List of primers

| SEQ ID NO: | Primer name | Sequence (5'→3') |
|---|---|---|
| 39 | OS2AP27L | TGTTGTTGTTGTTGCTGCTG |
| 40 | OS2AP27R | GCCGTGAGCCATATACACTTG |
| 41 | 023088C02 1L | AGCTCCAGCTCCTCCTCGAT |
| 42 | 023088C02 2L | TATCTCTCACCGACCCCAAA |
| 43 | 023088C02 2R | TGTTGCCATCAGGAGAGGA |
| 44 | 023088C02 3R | CTCTTGATGAAGCAGCATGG |
| 45 | 023088C02 3R | CCCAGTAAATGCAACCTTGTC |
| 46 | 023088C02 4R | GGCAACATGGAAGGTAGCTC |
| 47 | 023088C02 4R | CCATGCAACCATCCTTTCTT |
| 48 | 023088C02 5R | TTATGGCTTCAGCTGCTCCT |
| 49 | 023088C02 5R | CAATGGCTTCTTCTTCAGTGC |
| 50 | 023088C02 6R | GCCCGTTGTTAGTGAAGGAC |
| 51 | 023088C02 6R | GTACCATCCCCACGGCTCAT |
| 52 | 023088C02 7L | CGAGCGATGCCAGAGATTA |
| 53 | 023088C02 7R | AGCACATGGCAAATCAAACA |
| 54 | OS2AP-exon 7.1-del_F | TGCTCCTTTGTCATCACACC |
| 55 | OS2AP-exon 7.1-del_R | TTTCCACCAAGTTCCAGTGA |
| 56 | OS2AP_in1L | TTCGCTGCAGAACAGATGAC |
| 57 | OS2AP_in1R | CTGATGGTTACGCGACAATTT |
| 58 | OS2AP_inTA2L | ATTTGAACCGGGACAGAACA |
| 59 | OS2AP_inTA2R | TTTTGATGTGCCCTCTCCTT |
| 60 | OS2AP_inAAT3L | TGGGTAATCTTGTTCTGGAG |
| 61 | OS2AP_inAAT3R | AGTGCCAAATGCATGCTAGA |
| 62 | OS2AP_inG4L | TGGGGCTCAAAAACCTACTG |
| 63 | OS2AP_inG4R | GTCCGGGCCAAGTACCTC |
| 64 | OS2AP-5-UTR-EX1-5F | ATCTCTCACCGACCCCAAAT |
| 65 | OS2AP-5-UTR-EX1-5R | CCATTGGAAGAGAGACAGGTG |
| 66 | OS2AP-ATG1-600 F | TGTTGTTGTTGTTGCTGCTG |
| 67 | OS2AP-ATG1-600 R | TGGGGCTCAAAAACCTACTG |
| 68 | OS2AP-EX5-12 F | GGTTGGTCTTCCTTCAGGTG |
| 69 | OS2AP-EX5-12 R | GGTCCAAAAGCAACCAAAGA |
| 70 | Aromarker BigL | ACTGGTAAAAGATTATGGC |
| 71 | Aromarker BigR | CAAGCCGATCAACCAGTACA |
| 72 | Aromarker SmallL | CCATGCTGCAAGCAATGTA |
| 73 | Aromarker SmallR | AACCATAGGAGCAGCTGAAATA |

TABLE 1-continued

List of primers

| SEQ ID NO: | Primer name | Sequence (5'→3') |
|---|---|---|
| 74 | OS2AP8_OUT_F | ACCCTGGTGTAGACAAGGTA |
| 75 | OS2AP8_IN_F | GGGAGTTATGAAACTGGTATAT |
| 76 | OS2AP8_IN_R | ATAGGAGCAGCTGAAGCCAT |
| 77 | OS2AP8_OUT_R | GTCCCGCACTTCAGAATTAG |
| 78 | OS2AP8_ex2_F | CTCTGCTTCTGCCTCTGATT |
| 79 | OS2AP-exon9.1-del_RN | CTGGCTACTAGAATGATGCTC |
| 80 | Exon6to9NcoIF | AATTCCATGGGGTTGGTCTTCCTTCAGGTG |
| 81 | Exon6to9SpeIR | AATTACTAGTTTCCACCAAGTTCCAGTGAA |
| 82 | Exon6to8NheIR | AATTCCATGGGGTTGGTCTTCCTTCAGGTG |
| 83 | GFPU | CTTGTTGAATTAGATGGTGATGTT |
| 84 | GFPL | GTTGTGGGAGTTGTAGTTGTATTC |
| 85 | Os2APCH4U | TAGCTTCACATCCCCATGTG |
| 86 | Os2APCH4L | GCACCTTCACATCTTGCTGT |
| 87 | ActinU | ACATCGCCCTGGACTATGAC |
| 88 | ActinL | TGCTGAGAGATGCCAAGATG |
| 89 | GmAMADH2-1F | AGAGACTGGACTAGCTGAGT |
| 90 | GmAMADH2-1R | CTTTTGCTGTGCGTCCAATTT |
| 91 | GmAMADH2-2F | AAAGATCACCGAGAAAAGCC |
| 92 | GmAMADH2-2R | ACCTGAAGCGGGTGCTCCTT |
| 93 | GmAMADH2-3F | TGTTGATGGCTACGTGGAAG |
| 94 | GmAMADH2-3R | TGCATATCTGACCATTTGTCC |
| 95 | GmAMADH2-1F | TTTGAGGATGTTGACCTTGAC |
| 96 | GmAMADH2-1R | GATATTGAAGTTTATCTCAAATG |
| 97 | GmAMADH2-2F | GCAACAGAATTTTTGAATAGGA |
| 98 | GmAMADH2-2R | CAGCAGAACCCAAGCCATAT |
| 99 | GmAMADH2-3F | GATTCTTTGTTGAACCAACTG |
| 100 | GmAMADH2-3R | GCAGTCAAGATTATGTTGGTAG |

Os2AP homologs: Sequences that show similarity to those described in this application can be identified by computer-based methods, using public domain sequence alignment algorithms and sequence similarity search tools to search sequence databases (public domain databases include Gen-Bank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences or two amino acid sequences may be expressed in terms of sequence identity (or, for proteins, also in terms of sequence similarity). Sequence identity is frequently measured in terms of percentage identity; the higher the percentage, the more similar the two sequences are. As described herein, homologs and variants of the Os2AP protein-encoding nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

The alignment may include the introduction of gaps in the sequences to be aligned. In addition, for sequences which contain either more or fewer amino acids than the protein depicted in SEQ ID NO: 3 or SEQ ID NO: 6, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein for nucleic acids, and the protein homology described for proteins or polypeptides.

Os2AP polypeptide: As used herein, the term "Os2AP polypeptide" means a gene product having substantially the amino acid sequence of an Os2AP ortholog. The Os2AP protein is also known as OsBADH2. An Os2AP polypeptide is characterized, in part, in that a decrease in its expression, reduction in its mRNA levels, or reduction in protein amount or activity results in an increase in the levels of the compound 2-acetyl-1-pyrroline in the plant. An Os2AP polypeptide also is characterized, in part, by having an amino acid sequence with at least about 30%, 40%, 50%, 60%, 70%, 80%, 90% or 95% amino acid identity with the amino acid sequence depicted in SEQ ID NO: 3 or SEQ ID NO: 6. [SEQ ID NO: 99 or SEQ ID NO: 102.]

Substantially identical: By "substantially identical" is meant a polypeptide or nucleic acid exhibiting at least 30%, preferably 50%, more preferably 80%, and most preferably 90%, or even 95% homology to a reference amino acid sequence (for example, the amino acid sequence depicted in SEQ ID NO: 3 or SEQ ID NO: 6) [SEQ ID NO: 99 or SEQ ID NO: 102] or nucleic acid sequence (for example, the nucleic acid sequence depicted in SEQ ID NO: 1, SEQ ID NO: 2, SEQ ID NO: 4 or SEQ ID NO: 5) [SEQ ID NO: 97, SEQ ID NO: 98, SEQ ID NO: 100 or SEQ ID NO: 101.]. For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, or PILEUP/PRETTYBOX programs). For example, such software when set to standard parameters matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Elevated level: Elevated level, as used herein, means an increase in the average level of the compound 2-acetyl-1-pyrroline in a non-naturally occurring plant when compared to the average level of the compound 2-acetyl-1-pyrroline in the corresponding naturally occurring plant. Given that the level of the compound 2-acetyl-1-pyrroline in a plant will vary from plant to plant depending upon a number of variables, one of skill in the art would understand that in comparing the average level of the compound 2-acetyl-1-pyrroline in a non-naturally occurring plant and the corresponding naturally occurring plant, a reasonably sized sample population of each type of plant grown under similarly controlled conditions should be compared. The level of the compound 2-acetyl-1-pyrroline is preferably measured in several plants from each population and averaged to determine whether the non-naturally occurring plant contains an elevated level. The elevated level in the non-naturally occurring plant of the present invention is, on average, at least about 20% greater, 40% greater, 60% greater, 80% greater, 100% greater, 150% greater, 200% greater, 250% greater, 300% greater, 400% greater, or 500% greater than in the corresponding naturally occurring plant.

Promoter: A recognition site on a DNA sequence or group of DNA sequences that provide an expression control element for a structural gene and to which RNA polymerase specifically binds and initiates RNA synthesis (transcription) of that gene.

Examples of plant expression constructs using these promoters are found in Fraley et al., U.S. Pat. No. 5,352,605. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2:591, 1990; Terada and Shimamoto, Mol. Gen. Genet. 220:389, 1990). Moreover, activity of this promoter can be further increased (i.e., between 2-10 fold) by duplication of the CaMV 35S promoter (see e.g., Kay et al., Science 236:1299, 1987; Ow et al., Proc. Natl. Acad. Sci., U.S.A. 84:4870, 1987; and Fang et al., Plant Cell 1:141, 1989, and McPherson and Kay, U.S. Pat. No. 5,378,142).

Other useful plant promoters include, without limitation, the nopaline synthase (NOS) promoter (An et al., Plant Physiol. 88:547, 1988 and Rodgers and Fraley, U.S. Pat. No. 5,034,322), the octopine synthase promoter (Fromm et al., Plant Cell 1:977, 1989), figwort mosaic virus (FMV) promoter (Rogers, U.S. Pat. No. 5,378,619), and the rice actin promoter (Wu and McElroy, WO91/09948).

Exemplary monocot promoters include, without limitation, commelina yellow mottle virus promoter, sugar cane badna virus promoter, rice tungro bacilliform virus promoter, maize streak virus element, and wheat dwarf virus promoter.

Construct: Unless otherwise stated, the term "construct" refers to a recombinant genetic molecule comprising one or more isolated polynucleotide sequences of the invention.

Genetic constructs used for transgene expression in a host organism include a gene promoter sequence operably linked to an open reading frame and optionally a gene termination sequence 3' downstream of the open reading frame. The open reading frame may be orientated in either a sense or anti-sense direction, depending upon the intended use of the gene sequence. The construct may also include selectable marker gene(s) and other regulatory elements for gene expression.

Vector: A DNA molecule capable of replication in a host cell and/or to which another DNA segment can be operatively linked so as to bring about replication of the attached segment. Plasmids, phagemids, cosmids, phage, virus, YACs, and BACs are all exemplary vectors.

The term "vector" refers to a nucleic acid molecule which is used to introduce a polynucleotide sequence into a host cell, thereby producing a transformed host cell. A "vector" may include genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

Electroporation: The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding. To effect transformation by electroporation one may employ either friable tissues such as a suspension culture of cells or embryogenic callus, or alternatively one may transform immature embryos or other organized tissues directly. One would partially degrade the cell walls of the chosen cells by exposing them to pectin-degrading enzymes (pectolyases) or mechanically wounding in a controlled manner. Such cells would then be receptive to DNA transfer by electroporation, which may be carried out at this stage, and transformed cells can then identified by a suitable selection or screening protocol dependent on the nature of the newly incorporated DNA.

Microprojectile Bombardment: A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly obtaining stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust some of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-Mediated Transfer: *Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods.

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for elevated 2-acetyl-1-pyrroline levels relative to a control (native, non-transgenic) or an independent segregant transgenic plant.

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large genomic DNA fragment such as a contig is not sufficiently purified away from other biological components to be considered isolated due to the relatively large amount of extra DNA found in the average contig. As outlined below "recombinant nucleic acids" and "recombinant proteins" also are "isolated" as described above.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell; however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that such artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Non-naturally occurring plant: As used herein, the term "non-naturally occurring," when used in reference to a plant, means a plant that has been genetically modified by human intervention to alter the levels of the compound 2-acetyl-1-pyrroline in the plant. The naturally occurring plant that has been genetically modified is referred to as the "control" plant. Within the context of the invention, the control plant may be a transgenic plant. For example, the control plant may be an herbicide resistant transgenic plant. In this example, a non-naturally occurring plant would be herbicide resistant and would have elevated levels of the compound 2-acetyl-1-pyrroline compared to the control herbicide resistant plant. A transgenic plant of the invention, for example, is a non-naturally occurring plant that contains an exogenous nucleic acid molecule encoding an Os2AP gene or fragment thereof and, therefore, has been genetically modified by human intervention. In addition, a plant that contains a mutation in, for example, an Os2AP gene regulatory element or coding sequence as a result of calculated exposure to a mutagenic agent, such as a chemical mutagen, or an "insertional mutagen," such as a transposon or T-DNA, also is considered a non-naturally occurring plant, since it has been genetically modified by human intervention. In contrast, a plant containing only spontaneous or naturally occurring mutations is not a "non-naturally occurring plant" as defined herein. One skilled in the art understands that, while a non-naturally occurring plant typically has a nucleotide sequence that is altered as compared to a naturally occurring plant, a non-naturally occurring plant also can be genetically modified by human intervention without altering its nucleotide sequence, for example, by modifying its methylation pattern.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

I. The Os2AP Gene

A. Isolation of orthologs/homologs: The Examples section below, which describes the isolation and characterization of Os2AP polynucleotides in rice and soybean, is exemplary of a general approach for isolating Os2AP genes. Such Os2AP polynucleotides encode Os2AP polypeptides. The isolated polynucleotides can then be used to construct recombinant vectors for decreasing Os2AP gene expression in plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., (1989).

The isolation of an Os2AP polynucleotide may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaf, and a cDNA library which contains the Os2AP gene transcript is prepared from the mRNA. Alternatively, cDNA may be prepared from mRNA extracted from other tissues in which Os2AP genes or homologs are expressed.

The cDNA or genomic library can then be screened using a probe based upon the sequence of a cloned Os2AP gene such as the rice and soybean Os2AP genes disclosed here. Probes may be used to hybridize with genomic DNA or cDNA sequences to isolate homologous genes in the same or different plant species.

Nucleic acid molecules having sequence regions consisting of contiguous nucleotide stretches of 10-14, 15-20, 30, 50, or even of 100-200 nucleotides or so, identical or complementary to the DNA sequences depicted in SEQ ID NO: 1, SEQ ID NO: 2, SEQ ID NO: 4, SEQ ID NO: 5, SEQ ID NO: 97, SEQ ID NO: 98, SEQ ID NO: 100 or SEQ ID NO: 101 are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length of the complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating Os2AP polypeptide- or protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate Os2AP protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

Alternatively, the nucleic acids of interest can be amplified from nucleic acid samples using amplification techniques. For instance, polymerase chain reaction (PCR) technology can be used to amplify the sequences of Os2AP polynucleotides directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes Appropriate primers and probes for identifying Os2AP polynucleotide sequences from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983). Double stranded DNA fragments may then be obtained either by synthesizing the complementary strand and annealing the strands together under appropriate conditions, or by adding the complementary strand using DNA polymerase with an appropriate primer sequence.

B. Organisms from which to isolate an Os2AP gene ortholog A broad range of plants and fungi can be used, including species from the genera *Zea, Avena, Hordeum, Secale, Triticum, Glycine*, and *Sorghum*. 2-acetyl-1-pyrroline has been shown to be the major potent flavor compound of all aromatic rice, wheat and rye bread (Buttery et al., 1982, 1983), wet millet (Seitz et al., 1993), popcorn (Schieberle et al., 1991), aromatic vegetable soybean (Fushimi and Masuda, 2001), *Bacillus ceres* (Romanczyk et al., 1995), and some fungal species such as *Aspergillus oryzae, Aspergillus awamori*, and *Sporobolus virginicus* (Nagsuk et al., 2004). There are several reports which show genome-wide synteny among cereals as well as a well-conserved proline metabolic pathway in plants and microorganisms (found online at the web page for the Kyoto Encyclopedia of Genes and Genomes, Kyoto University, Bioinformatics Center, Institute for Chemical Research). Therefore, orthologs of the Os2AP gene may act in a comparable fashion among cereal plants, and the teachings provided in this invention can enhance the accumulation of the compound 2-acetyl-1-pyrroline in other plants in a similar way as in rice.

II. Reduction of Os2AP Gene Expression or Os2AP Protein Levels or Activity to Increase 2-acetyl-1-pyrroline Levels in Plants A. Mutagenesis Chemical mutagens such as EMS (methanesulfonic acid, ethyl ester) and both gamma ray and fast neutron radiation can create mutations in DNA. Some examples of mutations are deletions, insertions, and missense mutations. After mutation, screening can be done to identify deletions which create premature stop codons or otherwise non-functional Os2AP genes. Screening of mutants can be done by sequencing, or by the use of probes or primers specific to the Os2AP gene or protein, which are provided by the present invention. Specific mutations in Os2AP genes can also be created by TILLING (Targeted Induced Local Lesion of Genome) (Till et al., 2003) and tDNA insertion. Such mutations can result in decreases in Os2AP gene expression, decreased stability of Os2AP mRNA, or decreased activity and/or stability of the Os2AP protein. Such plants as defined herein are non-naturally occurring.

B. Antisense technology Antisense technology prevents the translation of target mRNA, such as Os2AP mRNA. As such, antisense technology generally reduces the levels of the target protein, here the Os2AP protein. The Os2AP gene or fragments thereof can be introduced into the plant in antisense orientation. The fragments can be as small as 18 nucleotides and as large as 3,000 nucleotides or larger. cDNA fragments of an Os2AP gene can be cloned into a vector (for example, pCAMBIA1302) in the opposite orientation as the native gene. The inverted transcript will form a heteroduplex structure with the native Os2AP gene transcript, which is then degraded before translation. The sense and antisense sequences need not be identical, even partial homology can be sufficient to achieve suppression of target gene expression. So, a sequence from rice Os2AP (SEQ ID NO: 1, SEQ ID NO: 2, SEQ ID NO: 4 and SEQ ID NO: 5) or from soybean GmAMADH2 (SEQ ID NO: 97, SEQ ID NO: 98, SEQ ID NO: 100 or SEQ ID NO: 101.) can be used to suppress Os2AP gene expression in other plants, without knowing the sequence of the Os2AP gene orthologs from that plant.

C. RNA interference: RNA interference (RNAi) is another technique which pertains to elimination of target mRNA. There are variations in the construction of vectors for RNAi, but the basic result is the formation of a hairpin loop structure in the RNA (Horiguchi 2004). In Example 2 a fragment of Os2AP nucleotide sequence encompassing exons 6, 7, and 8 in the opposite direction to its cDNA was cloned into a vector to result in an inverted hairpin structure in the mRNA. These hairpin structures are cleaved into small fragments by an endonuclease named Dicer, whose function is to prevent erroneous transcripts from being translated (Hamilton and Baulcombe, 1999, Matzke et al., 2001). The small fragments of mRNA are generally about 20 to 21 nucleotides in size, and have been termed siRNAs, or small interfering RNAs. Larger and smaller fragments can also be utilized. These siRNAs can downregulate the expression of homologous genes. Again, the homology need not be complete, so sequences from rice and soybean detailed in this invention could be used to create RNAi constructs for other plants. Example 2 shows how an RNAi experiment targeting the Os2AP gene in a non-aromatic rice strain resulted in elevated 2-acetyl-1-pyrroline levels, and fragrance, to a level found in aromatic rice. Example 10 shows how an RNAi experiment targeting the GmAMADH2 gene in a non-aromatic soybean strain resulted in elevated 2-acetyl-1-pyrroline levels.

III. Creation of Transgenic Plants

To use isolated Os2AP gene sequences in the previous techniques, recombinant DNA vectors suitable for transformation of plant cells can be prepared. Techniques for transforming a wide variety of higher plant species are well known and described in the technical and scientific literature. See, for example, Weising et al. Ann. Rev. Genet. 22:421-477 (1988).

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. Embo J. 3:2717-2722 (1984). Electroporation techniques are described in Fromm et al. Proc. Natl. Acad. Sci. USA 82:5824 (1985). Ballistic transformation techniques are described in Klein et al. Nature 327:70-73 (1987). Using a number of approaches, cereal species such as rye (de la Pena et al., Nature 325:274-276 (1987)), corn (Rhodes et al., Science 240:204-207 (1988)), and rice (Shimamoto et al., Nature 338:274-276 (1989) by electroporation; Li et al. Plant Cell Rep. 12:250-255 (1993) by ballistic techniques) can be transformed.

Agrobacterium tumefaciens-meditated transformation techniques are well described in the scientific literature. See, for example Horsch et al. Science 233:496-498 (1984), and Fraley et al. Proc. Natl. Acad. Sci. USA 80:4803 (1983). Although Agrobacterium is useful primarily in dicots, certain monocots can be transformed by Agrobacterium. For instance, Agrobacterium transformation of rice is described by Hiei et al., Plant J. 6:271-282 (1994).

Transformed plant cells which are derived by any of the above transformation techniques can be cultured to regenerate a whole plant which possesses the transformed genotype, and thus an elevated level of 2-acetyl-1-pyrroline and increased aroma. Such regeneration techniques rely on manipulation of certain phytohormones in a tissue culture growth medium, typically relying on a biocide and/or herbicide marker which has been introduced together with the Os2AP nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. of Plant Phys. 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

IV. Testing for 2-acetyl-1-pyrroline Levels

A. Sensory evaluation The volatile fragrance can be sensed from dry seeds, cooked rice, or ground leaves. (Dhulappanavar, 1976, Ghose et al., 1952, Kadam et al., 1938). Such sensing includes taste testing. Another popular practice among rice breeders is to heat leaf tissue in water followed by application of a solution of dilute KOH (Sood and Siddiq, 1978). These tests are not always consistent and reliable, and are prone to human error and preference.

Figure 1:
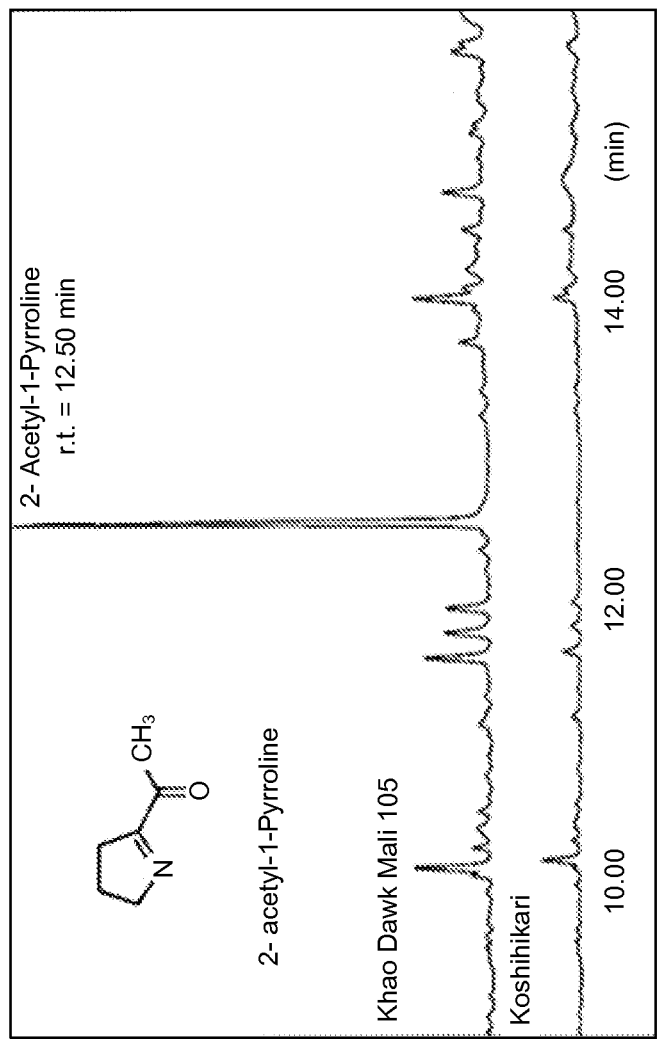
FIG. 1 depicts the chemical structure of 2-acetyl-1-pyrroline from GC-MS extracted from Khao Dawk Mali (KDML105), the That Jasmine rice (aromatic), and Koshihikari, a non-aromatic rice.

B. Chromatography: A more reliable method using gas chromatography was created for quantification of volatile compounds from 100 grams of cooked rice (Petrov et al., 1995). Recently, a gas chromatography/mass spectrometry (GCMS) technique was developed to analyze 2-acetyl-1-pyrroline levels as low as 1 part per billion from only one gram of rice (Mahatheeranont et al., 1995). As such, GCMS can be utilized to test levels of 2-acetyl-1-pyrroline in naturally occurring and non-naturally occurring plants. See FIG. 1.

Description of Preferred Embodiments

EXAMPLE 1

Positional Cloning of Gene Controlling Aroma in Rice

The rice aroma trait had been previously mapped onto chromosome 8 based on both qualitative and quantitative aroma determination methods (Lorieux et al. 1996). The aroma gene has been mapped at 4.5 cM away from RG28 (Ahn et al. 1992) and within 12 cM in between RG28 and RG1 (Lorieux et al. 1996). Recently, the single nucleotide polymorphism (SNP) marker RSP04 developed from the public rice genomic sequence has been mapped 2 cM away from the aroma gene (Jin et al. 2003).

The single QTL was located on the 4.5 cM region flanked by RFLP markers RG1 and RG28 on chromosome 8 (Lorieux et al., 1996; Lanceras et al. 2000). The EcoRI BAC library from KDML105 consisted of 75,264 clones representing 17 haploid genomes. An initial BAC contig consisting of twenty five BAC clones were selected by using six mapped markers within the region (Wanchana et al., 2005) and further refined using Hind III fingerprinting. To identify genes involved in the accumulation of 2-acetyl-1-pyrroline, the critical region was narrowed down using the following strategy.

Initially the single F6 plant that was segregating for grain aroma in F7 was selected as the source for generating new recombinants within the critical region. From F7 to F12, for each generation, heterozygous plants were selected based on both grain aroma and marker genotypes. In the F10 generation, the critical region was narrowed down to 380 kb by screening 374 F10 plants using eighteen polymorphic markers developed from KDML105 BAC end-sequences. The region was further refined to 120 kb by screening 274 µl plants (FIG. 2). Based on graphical genotyping and the amount of 2-acetyl-1-pyrroline, 8 µl plants were selected to generate aromatic, non-aromatic and heterozygous isogenic lines (FIG. 2). At this stage, three KDML BAC clones, 155L11, 68L13 and 167M23, were selected for shotgun sequencing. Alignment of the sequences from the KDML and corresponding Nipponbare genomic contigs resulted in the identification of 21 insertion/deletion ("indel") markers for further screening in the F12 generation. By using 1,116 F12 plants, the target region was narrowed down to 27 kb within the 58 kb BAC, 167M23 (FIG. 2). No further recombination was identified in this cross. Several pairs of isogenic lines were developed that clearly showed differences in 2-acetyl-1-pyrroline accumulation in rice grains (FIG. 6)

Sequence analysis revealed that the BAC 167M23 contains 19 genes. However, only ten genes have similarity to known proteins or coding sequences. Within the 27 kb region, three candidate genes were identified: 3-methycrotonyl-CoA carboxylase (MCCase), a hypothetical gene, and an unknown protein. Using 177 F6 plants from a cross between KDML105 and Jao Hom Nin (JHN), a non-aromatic black rice, a recombination site was identified within exon 7 of the unknown protein that affected grain aroma and 2-acetyl-1-pyrroline levels. To study the expression of these seven candidate genes from both BAC 167M23 and BAC 68L13, RT-PCR was performed during the grain filling period when 2-acetyl-1-pyrroline accumulates in rice grains. The total RNA was collected from rice panicles 10, 15 and 20 days after pollination from aromatic and non-aromatic isogenic lines. No expression was detected for the NBS/LRR gene. Most of the candidate genes did not show differential expression between the aromatic and non-aromatic isogenic lines. Only in the case of Os2AP, gene expression declined sharply in the aromatic isogenic lines 15 days after pollination (FIG. 3A). The decline in Os2AP gene expression was also pronounced in leaves, stems and roots (FIG. 3B). Therefore, both expression studies and positional cloning support Os2AP as the regulator responsible for accumulation of grain aroma and the synthesis of 2-acetyl-1-pyrroline in vivo.

Researchers had previously reported a single recessive nuclear gene controlling grain aroma (Berner and Hoff, 1986; Yanjuan et al., 1992; Ali et al., 1993). This is in accordance with the findings reported here. 2-acetyl-1-pyrroline accumulations were compared in aromatic and non-aromatic isogenic lines and the F1 plants. The results showed that 2-acetyl-1-pyrroline was not detected in F1 leaves. Because of segregation in the F2 generation, the 2-acetyl-1-pyrroline level was a quarter of the level found in the donor parents (FIG. 3C). Therefore, both classical and molecular genetics supported that the mutation in exon 7 is the molecular mechanism regulating 2-acetyl-1-pyrroline accumulation in planta.

The structures of the Os2AP genes were compared among KDML105, an aromatic isogenic line, a non-aromatic isogenic line, and Nipponbare. The 5.8 kb Os2AP gene consisted of 15 exons with several synonymous mutations found in exon 2 (FIG. 5A-C). For KDML105 and the aromatic isogenic lines, two important mutation events were identified in exon 7. First, two transitive mutations were found at positions 730 (A to T) and 732 (T to A), followed by the 8 base pair deletion 'GATTAGGC' starting at position 734. Analysis of 2-acetyl-1-pyrroline levels among 8 isogenic lines showed that the 8 base pair deletion is associated with the accumulation of 2-acetyl-1-pyrroline in rice grains (FIG. 6A). This mutation caused a frameshift translation start at position 729 and created the premature stop codon starting at position 753 (FIG. 5D). In Nipponbare, the Os2AP full-length cDNA is translated into 503 amino acids. The deletion created a truncated peptide of 252 amino acids (FIG. 5D). In the 177 F6 plants derived from KDML105 and JHN, double recombination flanking the 8 base pair deletion explains the failure to produce 2-acetyl-1-pyrroline in rice grains.

This premature stop codon may have significant effects on expression of Os2AP. Most mRNAs that contain a premature translational termination codon often fail to be translated. Consequently, they often trigger nonsense-mediated mRNA decay (NMD), a surveillance system whose function is to reduce errors in gene expression (Pulak and Anderson, 1993). This phenomenon may explain the low level of Os2AP gene expression in aromatic rice.

It is possible that Os2AP plays a role in the metabolic pathway of proline. The synthesis of glutamic acid from proline requires proline dehydrogenase (PropH) and delta-1-pyrroline-5-carboxylase dehydrogenase (P5CDH). During the grain filling period, expression of proline dehydrogenase was undetectable while Os2AP gene expression was up-regulated in non-aromatic isogenic lines. Therefore, it is possible that Os2AP replaces PropH in non-aromatic rice whereas in aromatic rice the degradation of Os2AP may shift the proline pool to be used for 2-acetyl-1-pyrroline synthesis. The isotopic labeling experiments also supported this hypothesis (Yoshihashi et al., 2002).

EXAMPLE 2

Plant Transformation Using Os2AP Genes

The Os2AP gene was incorporated into an RNAi construct which was used to down regulate Os2AP gene expression and enhance 2-acetyl-1-pyrroline levels in rice.

Construction of Os2AP-ihpRNA containing vector A pCAMBIA1302 vector was used for expressing sense-antisense fragments of the Os2AP gene. Sense and antisense fragments were made by PCR using genomic DNA and total RNA from KDML105 as templates, respectively. A sense fragment-containing genomic DNA sequence corresponding to exons 6 through 9 was amplified with the primers containing NcoI and SpeI restriction sites (underlined) (forward: AATTCCATGGGGTTGGTCTTCCTTCAGGTG (SEQ ID NO: 80); reverse: AATTACTAGTTTCCACCAAGTTC-CAGTGAA (SEQ ID NO: 81)). An antisense fragment containing a cDNA sequence corresponding to exons 6 through 8 was amplified with the primers containing NcoI and NheI restriction sites (forward: AATTCCATGGGGTTGGTCT-TCCTTCAGGTG (SEQ ID NO: 80); reverse: AAT-TGCTAGCGGTCCAAAAGCAACCAAAGA (SEQ ID NO: 82). The PCR products were first digested with SpeI and NheI and subsequently ligated with T4 DNA ligase. The ligated fragments were then digested with NcoI. The purified ligated fragments were cloned into pCAMBIA1302 vector at the NcoI cloning site (FIG. 7A).

Rice transformation Embryogenic calli of a non-aromatic rice variety (*Oryza sativa* L. *japonica* variety Nipponbare) were used as target tissues for particle bombardment transformation (Nimlek, 1999). Hygromycin-resistant calli were screened by PCR using the primers Os2AP-exon 7.1-del_F and R (U: 5'-TGCTCCTTTGTCATCACACC-3' (SEQ ID NO: 54) and L: 5'-TTTCCACCAAGTTCCAGTGA-3' (SEQ ID NO: 55)) and primers for GFP (U: 5'-CTTGTTGAATTA-GATGGTGATGTT-3' (SEQ ID NO: 83) and L: 5'-GT-TGTGGGAGTTGTAGTTGTATTC-3' (SEQ ID NO: 84).

Southern blot analysis Total DNA was isolated from leaves of transgenic (R0) and control (Nipponbare) plants. Genomic DNA (10 mg) was digested with NcoI for detection of Os2AP-ihpRNA fragments. As a positive control, the DNA isolated form the plasmid Os2AP-RNAi was digested with NcoI. Following electrophoresis through a 0.8% agarose gel, DNA was transferred to Hybond-N+ Nylon membranes (Southern 1975). Hybridization with the probe was done according to the instructions of the manufacturer (Amersham). The radioactive probe was prepared by the random primer method using ($\alpha$-$^{32}$P)-dCTP. The probe consisted of the coding region of the Os2AP gene (SpeI-NcoI fragment of pOs2AP-RNAi, 210 nucleotides).

RT-PCR To investigate transcription levels at different growth stages and in different tissues, total RNA was extracted from young plants (10 days), adult leaves (30 day) and roots (14 days), and flowering panicles of Nipponbare and transgenic plants and used for RT-PCR analysis. The Os2AP gene aroma locus on chromosome 8 was amplified by PCR using the Os2AP-exon7.1 primers (U: 5'-TGCTC-CTTTGTCATCACACC-3' (SEQ ID NO: 54) and L: 5'-TTTCCACCAAGTTCCAGTGA-3' (SEQ ID NO: 55)). A homolog of the Os2AP gene on chromosome 4 also referred to as BADH (Os2AP-chr4; Genbank Accession No. AB001348) was amplified by PCR using Os2APch4 primers (U: 5'-TAGCTTCACATCCCCATGTG-3' (SEQ ID NO: 85) and L: 5'-GCACCTTCACATCTTGCTGT-3'(SEQ ID NO: 86) As a control, the rice actin gene (GenBank Accession No.: X16280) was amplified with ActinU: 5'-ACATCGCCCTG-GACTATGAC-3' (SEQ ID NO: 87) and ActinL: 5'-TGCT-GAGAGATGCCAAGA TG-3' (SEQ ID NO: 88).

Real-time quantitative PCR Real-time quantitative PCR was performed by utilizing TAQMAN detection chemistry and the ABI PRISM 7700 Sequence Detection System (Applied Biosystems, Foster City, Calif., USA) according to the manufacturer's instructions. Relative amounts were calculated as the ratio of the copy number of Os2AP to that of rice actin. A TAQMAN detection probe was designed to differentiate between the aromatic and non-aromatic alleles of the Os2AP gene.

Results: Four hygromycin-GFP positive plantlets were regenerated. Expression of the GFP varied in the transgenic rice plants. T$_0$RNAi2 (10), the line with the best expression of the GFP, has the least expression of endogenous Os2AP (FIG. 7B). Analysis of 2-acetyl-1-pyrroline contents and sensory evaluation using the KOH method were well correlated. T$_0$RNAi2 (10) contained the highest amount of 2-acetyl-1-pyrroline and had the most aromatic leaves. T$_0$RNAi5(20) and T$_0$RNAi3(30), which express low amounts of the interfering sequence, accumulated less 2-acetyl-1-pyrroline and had lower aromatic leaf scores (FIG. 7B). Segregation analysis of grain aroma in T$_1$RNAi2 (10) confirmed this result. Therefore, the suppression of Os2AP gene expression by RNA interference enhances the accumulation of 2-acetyl-1-pyrroline in rice plants. This suggests that the natural suppression of Os2AP gene expression by NMD in aromatic rice caused by the 8 base pair deletion is the direct cause of aromatic rice aroma.

EXAMPLE 3

Characterization of the Os2AP/BADH Loci of Rice

Os2AP is a homolog of BADH (betaine aldehyde dehydrogenase) previously found on chromosome 4 (Nagamura et al., 1997). The genomic sequence of the BADH gene from chromosome 4 and the Os2AP gene on chromosome 8 were characterized from the Genbank sequence accession numbers AB001348 and AP004463, respectively. According to gene annotation results from RiceGAAS (Rice Genome Automated Annotation System, from Sakata et al., 2002), the structural genes of both BADH and Os2AP comprise 15 exons interrupted by 14 introns. The ORFs encode proteins of 505 and 503 amino acid residues for BADH and Os2AP respectively. Both proteins are 77% identical at the amino acid level and share between 88% to 99% identity with other plant BADH proteins. Moreover, these two proteins contain nucleotide sequences encoding the decapeptide Val-Thr-Leu-Glu-Leu-Gly-Gly-Lys-Ser-Pro (SEQ ID NO: 96), which is highly conserved among general aldehyde dehydrogenases (Weretilnyk et al. 1990). According to Pfam analysis of the protein sequences, both BADH and Os2AP belong to the aldehyde dehydrogenase family. Proteins in this family have putative function in the synthesis of glycine betaine in certain plant species. However, in cereals like rice, maize, and wheat which do not accumulate glycine betaine, the function of these proteins is not known. It was surprising that pyrroline-5-carboxylate dehydrogenase (P5CDH), (Genbank Accession No. P30038) which functions in proline catabolism is also included in this family, since proline has been reported as the precursor of 2-acetyl-1-pyrroline. It is possible that the function of Os2AP is to catalyze the dehydrogenation of other aldehydes than betaine aldehyde.

Os2AP gene expression and rice aroma In order to identify whether Os2AP on chromosome 8 and BADH on chromosome 4 relate to aroma biosynthesis, the expression levels of aromatic and non-aromatic isogenic lines (whose genomic backgrounds were identical except for the aroma gene region) were analyzed. As a result, BADH did not show differential expression between both isogenic lines, while Os2AP consistently showed gene suppression in all tissues of the aromatic isogenic lines (FIG. 3D). The expression of both proteins in isogenic lines and Nipponbare and K105 (aromatic strain) was also studied. Os2AP gene expression was down regulated only in the aromatic isogenic lines and KDMLL105. In contrast, there was no detection of down regulation of Os2AP gene expression in the non-aromatic isogenic lines and Nipponbare rice (non-aromatic strain).

EXAMPLE 4

Marker Assisted Selection

To develop new aromatic rice by conventional cross-breeding, one may cross an aromatic rice donor and a more productive recipient rice variety. The progeny from the cross will segregate for grain aroma among other traits. This situation confuses breeders and makes conventional breeding for better aromatic rice less successful. The discovery of the aroma gene will turn out to be a new paradigm for conventional breeders. Specific molecular markers can be developed to detect the aroma gene so that thousands of plants can be screened with the highest accuracy. DNA marker technology can allow breeders to detect the aromatic allele of the Os2AP gene at an early stage with high sensitivity. This leaves more opportunity for breeders to add preferred traits into aromatic plants at a later stage. The molecular basis of aroma identified in rice can possibly be found in other cereals and this will open ways to develop DNA markers for other cereals as well.

EXAMPLE 5

Phylogenetic Analysis of Os2AP Gene

Proline biosynthesis is a highly conserved pathway in the plant kingdom. The biosynthesis of 2-acetyl-1-pyrroline proposed here may be a common theme utilized by other 2-acetyl-1-pyrroline-producing plants. To illustrate this point, the amino acid sequences of Os2AP genes were compared using multiple sequence alignment. The resulting phylogenetic tree shows that the Os2AP genes from rice, wheat and barley may share a common ancestor (FIG. 9B). Therefore, biosynthesis of 2-acetyl-1-pyrroline among cereals may share a common theme. Experiments with Os2AP gene orthologs in other cereals must be conducted in the future to illustrate this point.

It is interesting to trace back where the Os2AP gene came from. By scanning 95 landrace varieties using the "Aromarker" PCR primers, it was found that the allele with the 8 base pair deletion correlates exactly with increased aroma. Exon 7 was also sequenced for the 8 base pair deletion among wild species including *Oryza nivara* and *O. rufipogon* (FIG. 9A). Most aromatic varieties including That Jasmine, Basmati and Azucena were found to have the deletion, and therefore share a common ancestor that may trace back to the ancient time. The aromatic allele in aromatic wild rice was identified as well. Therefore, a single mutation arose long before cultivation by humans to give rise to the aromatic rice of today.

EXAMPLE 6

Aroma Determinant and AMADH Activity Analyses Among Aromatic and Non-aromatic Vegetable Soybean Ten varieties of aromatic and non-aromatic vegetable soybean were selected to characterize the aminoaldehyde dehydrogenase (AMADH) activity in their young seeds. The phenotypes of the ten varieties were analyzed by detecting the 2AP content contained in the seeds using a headspace gas chromatography (HS-GC) to confirm that 2AP was the major determinant of the aromatic phenotype. 2AP was detected in seeds of all five aromatic varieties but not detected in those of non-aromatic varieties (Table 2). The AMADH activity of the crude enzyme preparations isolated from young seeds of the ten soybean varieties was then analyzed in a non-denaturing polyacrylamide gel (native PAGE). The proper substrate of soybean AMADH between 4-aminobutyaldehyde and betaine aldehyde was tested. The result showed that only 4-aminobutyraldehyde can be catalyzed by the AMADH (FIG. 17). Therefore, only 4-aminobutyraldehyde was used as a substrate for AMADH in the enzyme activity gel staining assays for the ten soybean varieties. The activity gel staining assay revealed that there were four AMADH activity bands on the PAGE gel. Interestingly, one of these bands appeared in all non-aromatic soybean samples but was absent in all aromatic soybean samples (FIG. 10). This activity band was marked as the AMADH enzyme that was associated with the non-aromatic phenotype because it was expressed only in the non-aromatic soybean varieties.

TABLE 2

The relative content of 2AP in soybean seed was determined by automated headspace gas chromatography with a nitrogen-phosphorus detector (HSGC-NPD).

| Variety | Peak area ratio of 2AP (mean ± SD) | Phenotype |
| --- | --- | --- |
| Okuhara wase | n.d. | Non-aromatic |
| Oishi Edamame | n.d. | Non-aromatic |
| Shirono Mai | n.d. | Non-aromatic |
| Chiang Mai 60 | n.d. | Non-aromatic |
| Jack | n.d. | Non-aromatic |
| Chamame | 0.1434 ± 0.0048 | Aromatic |
| Kouri | 0.1441 ± 0.0063 | Aromatic |
| Kaori Hime | 0.2419 ± 0.0084 | Aromatic |
| Fukunari | 0.1484 ± 0.0073 | Aromatic |
| Yoagari musume | 0.2160 ± 0.0095 | Aromatic | n.d. = not detected

Plant materials: Ten varieties of aromatic and non-aromatic vegetable soybean [*Glycine max* (L.) Merrill.] were used in this experiment. The five aromatic soybean varieties, Chamame, Kouri, Kaori Hime, Yuagari musume and Fukunari, and the three non-aromatic soybean varieties, Okuhara Wase, Oishi Edamame and Shirono Mai, were collected from market shelves in Japan. Another non-aromatic soybean variety, Jack, was provided by Professor Randall L. Nelson, USDA, Agricultural Research Service, Illinois, USA. In addition, non-aromatic variety, Chiang Mai 60 (CM60), was provided by Professor Peerasak Srinives, AVRDC, Kasetsart University, Thailand. Mature seeds of each variety were grown in pots under open-air conditions at Kasetsart University, Nakhon Pathom, Thailand. Fresh pods from each plant were harvested from October through November 2008. The samples were kept in sealed plastic bags and stored at −20° C. for further experiments.

2-Acetyl-1-Pyrroline analysis in soybean seed: An automated headspace gas chromatography (HSGC) comprising an Agilent Technologies (Wilmington, Del.) model 6890N gas chromatograph, an Agilent Technologies model G1888 headspace autosampler, and a nitrogen-phosphorus detector (NPD) was utilized for headspace volatile extraction and quantitative analysis of 2AP in the soybean samples. Identification of 2AP in the soybean headspace was accomplished using a HP 5973 mass-selective detector (Agilent Technologies, Palo Alto, Calif.) equipped with the Wiley 7N Mass Spectral Library and the NIST 05 Mass Spectral Library, both purchased from Agilent Technologies. Additionally, structural confirmation by mass spectral comparison with that of an authentic 2AP was performed. The HSGC conditions were the same as those reported by Sriseadka et al. (2006) with some modifications. Chromatographic separation was performed on a fused silica capillary column, phase HP-5MS (60 m×0.32 mm i.d.×1.0 µm) (Agilent Technologies). Purified helium gas at a flow rate of 1 mL/min was used as the GC carrier gas. The mass spectrometer was operated in the electron impact (EI) mode with an electron energy of 70 eV; ion source temperature, 230° C.; quadruple temperature, 150° C.; mass range m/z 29-550; scan rate, 0.68 s/scan; EM voltage, 1423 V. The GC-MS transfer line was set to 280° C. The system operation, as well as data acquisition, collection, and evaluation, were accomplished using an Agilent ChemStation software version A.01.04 and B.01.03 (Agilent Technologies, Waldbronn, Germany).

Partially-purified AMADH preparation: Crude enzymes from soybean callus were extracted with cold extraction buffer (100 mM KPi (pH7.5), 10% (v/v) glycerol, 2% (w/v) PVPP, 1 mM EDTA, 1 mM NAD and 1 mM DTT, at a ratio of 400 mg fresh weight/ml) after grinding the young seeds using a mortar and pestle. The homogenate was centrifuged at 14,000 rpm for 15 minutes. The supernatant was fractionated with solid $(NH_4)_2SO_4$, and the fraction containing 55-75% saturation was collected. The fraction was resuspended in 500 µl of 100 mM KPi (pH 7.5) buffer and desalted through a NAP-5 column (GE Lifesciences). 1 mM NAD, 1 mM EDTA and 1 mM DTT were added to obtain desalted solutions, and the crude extracts were assayed immediately. All extraction procedures were done at 4° C.

AMADH activity gel staining assay: A non-denaturing polyacrylamide mini-gel system (Bio-Rad Laboratories, Inc. USA) was used in this study to assay AMADH activity. Total enzyme extract (20 µg in 16 µl) was mixed with 4 µl gel-loading buffer containing 50% (v/v) glycerol and 0.05% (w/v) bromophenol blue. The samples were then separated in the 10% PAGE gel, Tris-HCl, pH 8.8. The electrode buffer contained 25 mM Tris-HCl and 192 mM glycine. Separation was performed with constant current at 20 mA/gel at 4° C. Staining was performed at 37° C. in a solution containing 100 mM glycine-NaOH buffer (pH 9.5), 1 mM NAD, 5 mM 4-Aminobutanal, 1 mM (3-4,5-dimethylthiazol-2-yl)-2,5-diphenoy-tetrazolium bromide (MTT), and 0.15 mM 1-methoxy-phenazine methosulphate, until the bands were visible. The reaction was terminated by adding 10% acetic acid, then distilled water.

EXAMPLE 7

Identification of Candidate Genes for Aroma and AMADH in Soybean

The identification of candidate genes for the aromatic trait in the vegetable soybean was achieved by a sequence comparative approach using the rice gene responsible for 2AP biosynthesis, OsBADH2 (Os08g0424500), as a reference. The deduced protein sequence of OsBADH2, GenBank Accession No. NP_001061833, derived from the japonica cultivar Nipponbare was used to perform a protein homology search against NCBI's protein database using BLASTP (Basic Local Alignment Search Tool for protein searching). Two proteins, Accession Nos. BAG09376 and BAG09377, highly matched to the rice query protein with amino acid sequence identities of 75 and 74%, respectively. Both BAG09376 and BAG09377 were previously identified in soybean's peroxisome and annotated as peroxisomal betaine-aldehyde dehydrogenase (BADH) (Arai et al., 2008). The number of rice OsBADH2 homologous genes in soybean was confirmed by using the two coding sequences (CDSs), AB333793 and AB333794, associated with BAG09376 and BAG09377, respectively, to perform a nucleotide search (BLASTN) against a recently released (assembly Glymal) shotgun genome sequence database of soybean (*Glycine max*) (Phytozome: available at www.phytozome.net/soybean). Two gene locus models, Glyma05g01770 and Glyma06g19820, which were annotated as BADH, hit the query CDSs with the highest scores. The two genes in soybean associated with the CDSs AB333794 and AB333793 were named GmAMADH1 and GmAMADH2, respectively, in this study. Both GmAMADH1 and GmAMADH2 comprise 15 exons interrupted by 14 introns. The CDSs and deduced amino acid sequences of GmAMADH1 and GmAMADH2 were identical to those of previously reported soybean sequences (Arai et al., 2008). Because the homology of the two BADHs in soybean was higher when compared within species than when compared to rice, both genes were considered to be putative candidate genes for the aromatic trait.

EXAMPLE 8

Transcription Profiling of the Two Aromatic Candidate Genes Among Aromatic and Non-aromatic Soybean Varieties The transcription profile of the two candidate genes, GmAMADH1 and GmAMADH2, was analyzed in order to observe whether it was linked to the AMADH activity difference between aromatic and non-aromatic soybean. The same vegetable soybean varieties as those used in the AMADH activity analysis were subjected to transcription profiling. RT-PCR analyses of GmAMADH1 and GmAMADH2 expression in young seeds clearly demonstrated that GmAMADH2 was down regulated in all five aromatic soybean varieties. On the other hand, the expression level of GmAMADH1 was unchanged among the ten soybean varieties (FIG. 11). The transcription profiles of the two genes were also analyzed in young leaves and callus tissues of the ten varieties. The results revealed the same pattern of that found in young seeds (FIG. 11).

Total RNA isolation: Total RNA was extracted from immature seed, leaf, and callus tissues of the ten varieties of soybean by using the RNeasy mini kit (QIAGEN). The total quantity of RNA was examined by using a spectrophotometer.

Reverse transcriptase polymerase chain reaction (RT-PCR): The DNAase-treated RNA was reverse-transcribed and PCR amplified using Titan One Tube RT-PCR Kit (Roche Applied Science) according to the manufacturer's instructions. The reverse transcription and PCR thermal cycle conditions were as follows: reverse-transcription at 50° C. for 30 min, then starting the PCR cycles by initial heating at 95° C. for 3 min followed by 27-37 cycles for 95° C., 30 sec; 55° C., 30 sec; 68° C., 1 min, and a final extension at 68° C. for 5 min. The number of cycles was adjusted to avoid over-cycling, and all RT-PCR assays were carried out in triplicate. The primers were designed based on the two mRNA accessions AB333794.1 and AB333793.1 for GmAMADH1 and GmAMADH2, respectively (Table 1) [.

EXAMPLE 9

Sequence Variation in the CDS of GmAMADH2

The two representative varieties, Chamame and Chiang Mai 60 (CM60), for aromatic and non-aromatic soybean, respectively, were selected for sequencing of their full-length CDSs based on their amplified RT-PCR products covering the GmAMADH2 coding region. The sequence alignment comparing the coding regions between the two varieties revealed that both of them contained almost identical CDSs, except for a region in exon ten at nucleotide 928 to 932 downstream of the first ATG where two Thymine (T), TT, were absent in the aromatic variety Chamame (FIG. 12a). In silico translated amino acid sequences from the CDS of the aromatic variety that contained the TT deletion was truncated and comprised only 311 amino acids. The fully-translated amino acid sequence comprising 503 amino acids identical to the protein accession BAG09376 was present in the non-aromatic variety CM60. Accordingly, it was shown that the frame-shifted 2-bp deletion caused a premature stop codon at the location just after three bases following the deletion (FIG. 12b). The presence of this 2-bp deletion in other aromatic varieties was confirmed by sequencing the genomic DNA of all ten soybean varieties used in this study. As expected, the 2-bp deletion in exon ten of GmAMADH2 was found only in aromatic varieties but not in non-aromatic varieties (FIG. 12a).

Total RNA and genomic DNA isolation: Total RNA was extracted from immature seed, leaf, and callus tissues of the ten varieties of soybean by using the RNeasy mini kit (QIAGEN). Genomic DNA was extracted from young leaves by using the DNeasy mini kit (QIAGEN). The total quantity of RNA and genomic DNA was examined by using a spectrophotometer. RT-PCR was performed as described in Example 8.

Polymerase chain reaction (PCR): PCR was performed in 25 µl reaction mixtures containing 50 ng of DNA template, 0.1 mM of dNTPs, 0.25 mM of each forward and reverse primer, 0.25 unit of Taq DNA polymerase, 2.0 mM $MgCl_2$ and 1× Thermophilic DNA Polymerase buffer (Promega). After pre-heating at 94° C. for 2 min, the PCR reaction was carried out for 30 cycles under the following conditions: 94° C. denaturation for 30 sec, 55° C. annealing for 30 sec, 72° C. extension for 1 min, and final extension at 72° C. for 5 min.

DNA sequencing and sequence assembly: The amplified PCR fragments were purified and cloned into pGEM-T Easy Vector (Promega, USA). The templates were sequenced from both directions by an automatic sequencing using the ABI PRISM™ Big Dye™ Terminator Cycle (Applied Biosystem/Perkin-Elmer, San Jose, Calif.). Sequences were assembled and viewed using the phred/phrap/consed software (phrap.org).

EXAMPLE 10

Functional test of GmAMADH2 by RNAi-mediated Suppression

In order to verify that the production of 2AP in aromatic soybean was indeed associated with the inactivation of GmAMADH2, the gene was knocked out in a non-aromatic soybean by an RNAi-mediated gene suppressor (Miki and Shimamoto, 2004). An *Agrobacterium*-based gene transformation method was used to introduce an RNAi vector containing GmAMADH2 fragments, pANGmAMADH2 (FIG. 16), to the callus tissues of the two non-aromatic soybean varieties, CM60 and Jack. The pANGmAMADH2-transformed lines were identified based on the presence of GUS-linker fragment, which served as a loop in the transcribed RNAi construct. In this study, gene suppression, aroma phenotype and enzyme activity was investigated at the callus stage without the regeneration of soybean plant from the callus. RT-PCR analysis revealed that the expression of GmAMADH2 in both pANGmAMADH2-transformed lines was highly suppressed compared to the both wild type controls (FIG. 13). The pANGmAMADH2 RNAi vector was highly effective in suppressing the expression of GmAMADH2 and was highly specific only to this gene without affecting its paralog, GmAMADH1 (FIG. 14). The Northern blot showed that siRNA generated by the RNAi mechanism resulted in the accumulation of pANGmAMADH2-transformed lines (FIG. 13). Quantification of 2AP content in the pANGmAMADH2-transformed lines compared to the wild type controls showed that 2AP was detected in transformed lines but not in wild type (Table 3).

TABLE 3

2AP content of soybean callus

| Variety | 2AP content (ppb; as FW) (mean ± SD) | Phenotype |
| --- | --- | --- |
| Wild type | | |
| Yuagari musume | 457.26 ± 32.25 | Aromatic |
| Kaori hime | 325.22 ± 48.27 | Aromatic |
| Okuhara wase | n.d. | Non-aromatic |
| Chiang Mai 60, CM60 | n.d. | Non-aromatic |
| Jack | n.d. | Non-aromatic |
| Transgenic line | | |
| CM60-RNAi (5-1) | 324.25 ± 45.21 | RNAi |
| Jack-RNAi (2) | 343.25 ± 50.23 | RNAi | n.d. = not detected

An assay of AMADH activity staining in a PAGE gel was performed to confirm the loss of enzyme activity in pANGmAMADH2-transformed callus. The assay was performed as described in Example 6. The results showed that the candidate AMADH activity band disappeared in pANGmAMADH2-transformed lines as well as in natural aromatic soybean varieties (FIG. 14). However, it is worth noting that the banding patterns of partially-purified soybean AMADH in young seeds and callus tissues showed some differences. First, one AMADH activity band was completely invisible in aromatic soybean callus in concordance with that in pANGmAMADH2-transformed callus. Second, another activity band was highly stained in young seed samples of both aromatic and non-aromatic soybean but was faintly stained in callus samples of all varieties.

Construction of RNAi vector: The DNA fragment of GmAMADH2 was amplified from genomic DNA of the vegetable soybean variety Jack by a PCR using the forward primer 5'-CACCATGAGCATCCCAATTCCCCA-3' and the reverse primer 5'-TTCGAGTTTTGCTAGTTCAGG-3'. The fragment spanned 441 bp covering exon 1, intron 1, and part of exon 2. The resulting amplified PCR fragment was cloned into the Gateway pENTR/D-TOPO cloning vector (Invitrogen), which carries two recombination sites (attL1 and attL2) for LR Clonase reaction. Subsequently, the target fragment was transferred into the pANDA destination vector (Miki and Shimamoto, 2004) by recombinase reactions. The resulting pANGmAMADH2 RNAi vector comprised a 35S promoter, and 441-bp sense and 441-bp antisense GmAMADH2 fragments that were interrupted by a 1-kb fragment of the gus linker (FIG. 16).

Callus induction and gene transformation: Soybean seeds were disinfected with 0.1% $HgCl_2$ with 1 drop of Tween-20 for 6-7 min, followed by a 3 to 5 times wash in distilled water. The sterilized seeds were placed on callus induction medium (CC) (Potrykus et al., 1979) with some modifications and incubated for 1 month at 25° C. in dark conditions. Induced callus tissues were excised from explant/callus complexes and proliferated in liquid Finer and Nagasawa Lite (FNL) medium (FNL macro salts, MS micro salts, B5 vitamins, 1% sucrose, 1 g 1-1 asparagine and 5 mg 1-1 2,4-D, pH 5.8), in which FNL macro salts consist of 2830 mg 1-1 KNO3, 463 mg 1-1×(NH4)2SO4, 370 mg 1-1 MgSO4.7H2O, 185 mg 1-1 KH2PO4 and 300 mg 1-1 CaCl2.2H2O (Samoylov et al., 1998). Flasks were placed on a shaker at 125 rpm, in dim light (5-10 µE m-2 s-1) at 25° C. The medium was replaced at weekly intervals by pipetting the spent medium out of the flask and replacing with fresh medium.

The construct pANGmAMADH2 was mobilized into the *Agrobacterium tumefaciens* strain AGL1 by electroporetion. *Agrobacterium* cultures harboring the RNAi vector were grown on the plate of YEB medium containing 50 mg/l Kanamycin and 50 mg/l hygromycin B at 28° C. until colony formation. Then, 50 ml liquid YEB medium containing 50 mg/l Kanamycin and 50 mg/l hygromycin B was inoculated with a single colony and shaken at 28° C. and 180 rpm until OD650 of 0.6-0.8. *Agrobacterium* cultures were pelleted at 3,000 rpm for 10 min, and resuspended in liquid co-cultivation medium (FNL medium) to OD650 of 0.2 for use in the inoculations. The wounded callus tissues were soaked in *Agrobacterium* inoculum suspension for 30 min. The inoculated callus tissues were randomly placed on co-cultivation medium (MSD20-ASG medium which consists of Murashige and Skoog (MS) salts (Murashige and Skoog, 1962), Gamborg's B5 vitamins (Gamborg et al., 1968), 3% sucrose, 20 mg 1-1 2,4-D, 200 µM acetosyringone, and 0.3% Phytagel (pH 5.8). Plates were incubated in the dark for 2 days at 25° C. Following co-cultivation, transgenic callus tissues were selected in selection medium (FNL, 30 mgl-1 hygromysin B and 300 mgl-1 Cefotaxime). The medium was replaced every week for 6 additional weeks then transgenic callus tissues were placed on solid selective medium (CC, 30 mgl-1 hygromycin B).

2-Acetyl-1-Pyrroline analysis in soybean callus: Portions of callus samples (0.1 g) were homogenized (Ika Ultra-Turrax T8 homogeniser, Staufen, Germany) with 0.5 mL of ethanol containing 200 ppb of 2-acetyl-(13C-methyl)-1-pyrroline (Yoshihashi et al., 2002). They were extracted at room temperature for 1 hour. After centrifugation, 2 µL of supernatant was injected onto a DB-Wax extr, 60 m×0.25 mm i.d.×0.25 µm thickness fused silica capillary column (Agilent, Calif.) installed in a Shimadzu GCMS-QP2010 GCMS system (Kyoto, Japan) with helium at a carrier velocity of 41.2 cm/sec. The injector and interface temperatures were set at 150 and 250° C., respectively. The oven program was as follows: column temperature was isothermally maintained at 40° C. for 2 min, programmed first at a rate of 10° C./min to 100° C., then 5° C./min to 140° C., and then 20° C./min to 250° C.; the column temperature was maintained isothermally at 250° C. for 10 min. The mass spectrometer was used in the electron ionisation mode with the ion source temperature set at 250° C., the analyser temperature set at 100° C., and ionisation energy at 70 eV. Single ion monitoring was set up to monitor m/z 111 for 2AP and m/z 112 for carbon-13 labelled 2AP. Under these conditions, the retention times of 2-acetyl-1-pyrroline and carbon-13 labelled 2AP were found to be 12.46 min. Quantification was performed by measuring the area ratios between ions at m/z 111 and 112, corresponding to 2AP and carbon-13 labelled 2AP. Each extract was analysed three times to obtain an average peak area.

RNA gel blot analysis: The total RNA was isolated from callus of vegetable soybean varieties Jack, Chiang Mai 60 (CM60), the RNAi-transformed Jack (Jack-RNAi), and the RNAi-transformed CM60 (CM60-RNAi), by using TRIZOL® Reagent (Invitrogen). The RNA samples were visualized on 1% agarose gel electrophoresis and quantified by a spectrophotometry (OD260). The total RNA samples were dissolved in 1 volume of 100% formamide and mixed well. Twenty µg of total RNA was resolved on a PAGE gel (15% polyacrylamide gel containing 7 M of urea), then transferred onto a Hybond-NX membrane (Amersham Biosciences) by electro-blotting. The hybridization was performed with a DIG-labeled DNA probe complementary to coding sequence of GmAMADH2 from the exon 1 to exon 2. The detection of signals was performed as previously described by Goto et al. (2003).

EXAMPLE 11

A Phylogenetic Tree of BADH and AMADH Homologs in Plants

Eleven plant species for which their genomes have been sequenced or for which the complete sets of BADH and AMADH homologs have been identified were selected for the construction of a phylogenetic tree. Six species are dicotyledonous and five are monocotyledonous. A homology search for BADH homologs demonstrated that all selected plants contained two paralogous genes in each species. The phylogenetic tree showed two distinct groups separating monocotyledonous from dicotyledonous species (FIG. 15a). In the monocotyledonous group, two clear orthologies were identified among the four species. However, such clear orthology was not found among dicotyledonous species. The two paralogs in each species were likely to be clustered together. Clusters of orthology were observed in some species that are evolutionarily related such as soybean and pea. The two paralogs of *Arabidopsis* were unusual in that one of its paralogs was out-grouped from other dicotyledonous homologs.

An interesting region in the amino acid sequences of BADH homologs was observed upon comparison of the multiple sequence alignment and the in silico protein domain analysis results. This region was predicted as an aldehyde dehydrogenase cysteine active site (E. A. and A. D., 1990) with Prosite regular expression [FYLVA]-x-{GVEP}-{DILV}-G-[QE]-{LPYG}-C-[LIVMGSTANC]-[AGCN]-{HE}-[GSTADNEKR]. All BADH homologous proteins could be separated into two groups based on the two patterns, FaNAGQVCSATS and FwTNGQICSATS. The first pattern was found only in the monocotyledonous subgroup of OsBADH1 orthologs. The second pattern was found in the other monocotyledonous subgroup of OsBADH2 orthologs, as well as in almost all BADH homologous proteins from dicotyledonous species, except for the paralog in soybean and one paralog in pea that contains FfTNGQICSATS instead (FIG. 15b). The BADH homologs in primitive green plants and green algae were added to the phylogenetic tree and protein domain analyses. Only one BADH homologous protein was found in each primitive species, and all of them contained the FwTNGQICSATS domain pattern.

Phylogenetic and protein domain analyses: A set of BADH homologous proteins in eleven higher plant (Angiosperms) genomes (*Pisum sativum, Zoysia tenuifolia, Oryza sativa, Zea mays, Sorghum bicolor, Arabidopsis thaliana, Populus trichocarpa, Glycine max, Amaranthus hypochondriacus, Atriplex hortensis* and *Hordeum vulgare*), a Lycophyte (*Selaginella moellendorffii*), a Chlorophyte genome (*Chlamydomonas reinhardtii*), and a Bryophyte genome (*Physcomitrella patens*) were obtained by using the rice OsBADH2 protein sequence as the sequence query in BLASTP searches against NCBI and Phytozome databases. Multiple sequence alignments and a phylogenetic tree were analyzed by using Phylogeny.fr, a robust phylogenetic tree analysis web service (available at www.phylogenyfr/version2_cgi/index.cgi) with the "One click" mode. This mode for the phylogenetic analysis pipeline allows for multiple sequence alignments using the MUSCLE program, curation of the aligned sequences using GBLOCK, identification of phylogeny using PhyML, and tree rendering using TreeDyn (Dereeper et al., 2008). The protein domains were predicted by the Prosite program (available at au.expasy.org/prosite/) with the default parameters.

EXAMPLE 12

Discussion

Detection of the volatile compound 2-Acetyl-1-pyrroline, 2AP, in all aromatic soybean varieties confirmed that it is the same aroma determinant as that found in aromatic rice. The 2AP produced in all aromatic soybean varieties was associated with a lack of AMADH activity. Although the mechanism underlying the production of the 2AP compound in plants is not clear, according to the previously reported genetic pathway of 2AP biosynthesis in rice, it is possible that plants produce 2AP in order to detoxify the 4-aminobutyraldehyde generated via the polyamine degradation pathway (Bradbury et al., 2008). In non-aromatic rice it was demonstrated that AMADH converted 4-aminobutyraldehyde to GABA. However, due to the lack of AMADH function in aromatic rice, another alternative pathway was needed. Bradbury et al. found that accumulated 4-aminobutyraldehyde was utilized to produce 2AP instead (Bradbury et al., 2008). It has been thought that the major biosynthetic pathway of GABA in plants is via glutamate catabolism (Shelp et al., 1999). Recently, Xing et al reported that in salt-stressed soybean roots up to 30% of GABA was produced through polyamine degradation (Xing et al, 2007). This result suggested that the biosynthetic pathway of GABA from 4-aminobutyraldehyde exists in plants.

Due to the use of partly-purified enzymes from soybean tissues in this study, four enzyme activity bands appeared in the enzyme activity gel-staining assay (FIG. 10). This result suggested the existence of putative AMADH isoforms or non-specific ALDHs in the partially purified enzymes (Sebela et al., 2001). Although several activity bands occurred, one band was absent in all aromatic varieties. It has been suggested that most plants are likely to contain two BADH homologs in their genomes (Fitzgerald et al 2009). However, the likely functions of the two BADHs are still ambiguous. Some researchers suggest they have both BADH and AMADH activities, e.g. in oat (*Avena sativa*) (Livingstone et al., 2002, 2003) and rice (*O. Sativa*) (Bradbury et al. 2008), but others suggest they have only AMADH activity, e.g. in pea (*Pisum sativum*) (Sebela et al. 2000). It is not easy to distinguish an AMADH from a BADH since their protein sequences are highly similar (Tylichová et al, 2007). The difference between the two enzymes might only be with respect to substrate specificity. Several studies reported that BADH can utilize betaine aldehyde as a substrate as well as some other amino aldehydes (Tylichová et al, 2007). However, many AMADHs are unable to utilize betaine aldehyde as a substrate and can only use aminoaldehydes. The partially purified enzymes from the crude extract analyzed on the activity gel in this study showed that 4-aminobutyraldehyde can be used as a substrate in soybean but not betaine aldehyde. This result suggested that the two BADH homologs in soybean contain AMADH function rather than BADH function.

Although two homologs of rice OsBADH2 were identified in soybean, it is likely that GmAMADH2 rather than GmaBADH1 plays a role in the 2AP biosynthesis in soybean according to the correlation of 2AP content in young seeds and gene expression patterns. Even though a sequence variation in the CDS of GmAMADH2 that led to a loss of function was found in all aromatic soybean varieties, it is unlikely that this reflected the same lineage of sequence variation between GmAMADH2 and OsBADH2. The TT deletion found in GmAMADH2 of aromatic soybean was not related to any type of sequence variations previously reported in rice OsBADH2. It was concluded that sequence variations in the BADH2 of rice and soybean have evolved independently but have the same effect. At present, only one type of sequence variation, TT-deletion, was discovered among the aromatic soybean varieties used in the study. However, other novel sequence variations could be found in an expanded collection of aromatic soybean varieties.

The functional test using the RNAi-mediated suppressor confirmed the interpretation that the candidate band present in all non-aromatic samples but absent in all aromatic samples was the AMADH activity band of the enzyme encoded by GmAMADH2, the rice OsBADH2 homolog. The other three activity bands are likely to be GmAMADH1 and the other aldehyde dehydrogenases (FIGS. 10 and 14).

Due to the high protein sequence similarity of genes encoding BADH and AMADH in plants are likely to be derived from the same evolutionary ancestor. The protein sequence alignments revealed two distinct groups of BADH homologous proteins in monocots (FIG. 15a), which can be separated based on the substrate-binding domain pattern [FYLVA]-x-{GVEP}-{DILV}-G-[QE]-{LPYG}-C-[LIVMGSTANC]-[AGCN]-{HE}-[GSTADNEKR] (E. A. and A. D., 1990). However, this is not the case for dicot species since only one type of consensus was found as the same pattern as AMADH monocot sub-groups (FIG. 15b). According to this result, it is likely that all BADH homologs in dicotyledonous species were closer to the monocotyledonous BADH2 subgroup than the BADH1 subgroup. It also suggested that the proteins in the BADH subgroup in monocot species derived from the AMADH progenitor before speciation events after monocot-dicot divergence. However, the two copies of BADH homologous proteins in dicot species were independently duplicated within species after speciation events. According to the phylogenetic tree in this study (FIG. 15a), the true orthologs of the two BADHs can be characterized among monocot plants, but the orthology of BADHs among dicot species or comparison across dicot and monocot species is not as easily characterized. Therefore, the gene orthologs to the rice OsBADH2 might be easily identified in monocots, but it is more difficult to identify such orthology in dicot species because as described above all BADHs in dicot species contained the same putative consensus domain as found in rice OsBADH2.

In summary, the conserved regulation of 2AP biosynthesis in rice and soybean was demonstrated in this study. The gene responsible for 2AP biosynthesis in soybean, GmAMADH2, was identified as the ortholog of rice OsBADH2. The protein encoded by GmAMADH2 has a similar function to that of rice OsBADH2, catalysis of 4-aminobutyraldehyde to produce GABA. The inactivation of GmAMADH2 caused by the 2-bp deletion in exon 10 led to 2AP compound production. According to this discovery, the inactivation of the rice OsBADH2 orthologs in other plants might also lead to the accumulation of the aromatic compound 2AP and may open the way to engineer the metabolic pathway for 2AP production in other plants by the inactivation of their BADH and AMADH homologs.

References

Abdullah et al., Biotechnology, 4:1087, 1986.

Ahn, S. N., C. N. Bollich and S. D. Tanksley. 1992. RFLP tagging of a gene for aroma in rice. Theor. Appl. Genet. 84:825-828.

Ali, S. S., S. J. H. Jafri, M. G. Khan and M. A. Butt. 1993. Inheritance studies for aroma in two aromatic varieties of Pakistan. IRRN 18:6.

Altschul, S. F. et al. (1990) J. Mol. Bio. 215:403-410.

Altschul, S. F. et al. (1994) Nat. Genet. 6(2):119-29.

Altschul S F, Gish W. Local alignment statistics. Methods Enzymol. 1996; 266:460-80.

An, A., and Norbert, D. K. (2006). Chemistry of 2-acetyl-1-pyrroline, 6-acetyl-1,2,3,4-tetrahydropyridine, 2-acetyl-2-thiazoline, and 5-acetyl-2,3-dihydro-4H-thiazine: Extraordinary maillard flavor compounds. Chemical reviews 106, 2299-2319.

Arai, Y., Hayashi, M., and Nishimura, M. (2008). Proteomic Analysis of Highly Purified Peroxisomes from Etiolated Soybean Cotyledons. Plant Cell Physiol. 49, 526-539.

Berner, D. R. and B. J. Hoff. 1986. Inheritance of scent in America long grain rice. Crop Sci. 26: 876-878.

Bradbury, L., Gillies, S., Brushett, D., Waters, D., and Henry, R. (2008). Inactivation of an aminoaldehyde dehydrogenase is responsible for fragrance in rice. Plant Molecular Biology 68, 439-449.

Buttery, R. G., L. C. Ling, B. O. Juliano, J. G. Turnbauhg. 1983. Cooked rice aroma and 2-acetyl-1-pyrroline. J. Agric. Food Chem: 823-826.

Buttery, R. G., L. C. Ling and O. B. Juliano. 1982. 2-acetyl-1-pyrroline: an important aroma component of cooked rice. Chem Ind (London). p. 958.

Callis and Walbot, Genes and Develop., 1:1183-1200, 1987.

Capecchi, "High efficiency transformation by direct microinjection of DNA into cultured mammalian cells," Cell, 22(2):479-488, 1980.

Clapp, "Somatic gene therapy into hematopoietic cells. Current status and future implications," Clin. Perinatol., 20(1): 155-168, 1993.

Corpet, F. (1988) Nucleic Acids Res. 16:10881-10890.

Cristou et al., Plant Physiol, 87:671-674, 1988.

Curiel, Agarwal, Wagner, Cotten. "Adenovirus enhancement of transferrin-polylysine-mediated gene delivery," Proc Natl. Acad. Sci. USA, 88(19):8850-8854, 1991.

Curiel, Wagner, Cotten, Bimstiel, Agarwal, Li, Loechel, Hu, "High-efficiency gene transfer mediated by adenovirus coupled to DNA-polylysine complexes," Hum. Gen. Ther., 3(2):147-154, 1992.

Dereeper, A., Guignon, V., Blanc, G., Audic, S., Buffet, S., Chevenet, F., Dufayard, J. F., Guindon, S., Lefort, V., Lescot, M., Clayerie, J. M., and Gascuel, O. (2008). Phylogeny.fr: robust phylogenetic analysis for the non-specialist. Nucl. Acids Res. 36, W465-469.

Dhulappanavar, C. V. 1976. Inheritance of scent in rice. Euphytica 25:659-622.

E. A., W., and A. D., H. (1990). Molecular cloning of a plant betaine-aldehyde dehydrogenase, an enzyme implicated in adaptation to salinity and drought. Proc. Natl. Acad. Sci. U.S.A. 87, 2745-2749.

Eglitis and Anderson, "Retroviral vectors for introduction of genes into mammalian cells," Biotechniques 6(7):608-614, 1988.

Eglitis, Kantoff, Kohn, Karson, Moen, Lothrop, Blaese, Anderson. "Retroviral-mediated gene transfer into hemopoietic cells," Adv. Exp. Med Biol., 241:19-27, 1988a.

Fraley et al., Bio/Technology. 3:629-635, 1985.

Fromm, Taylor, Walbot, "Expression of genes transferred into monocot and dicot plant cells by electroporation," Proc. Natl. Acad Sci. USA, 82(17):5824-5828, 1985.

Fujimura et al., Plant Tissue Culture Letters, 2:74, 1985.

Fushimi, T., and Masuda, R. (2001). 2-Acetyl-1-Pyrroline Concentration of the Aromatic Vegetable Soybean "Dadacha-Mame". Proceedings of Second International Vegetable Soybean Conference Washington State Univ., Tacoma, Wash. 39.

Fynan, Webster, Fuller, Haynes, Santoro, Robinson, "DNA vaccines: protective immunizations by parenteral, mucosal, and gene gun inoculations," Proc. Natl. Acad Sci. USA 90(24):11478-11482, 1993.

Gamborg, O. L., Miller, R. A., and Ojima, K. (1968). Nutrient requirements of suspension culture of soybean root cells. Experimental Cell Research 50(1), 151-158.

Ghose, R. L. M. and W. T. Butany. 1952. Study on the inheritance of some characters in rice (Oryza sativa L.). Indian J. Genet. Plant Breed. 12:26-30.

Goto, K., Kanazawa, A., Kusaba, M., and Masuta, C. (2003). A Simple and Rapid Method to Detect Plant siRNAs Using Nonradioactive Probes. Plant Molecular Biology Reporter, 51-58.

Graham and van der Eb, "Transformation of rat cells by DNA of human adenovirus 5," Virology 54(2):536-539, 1973.

Hamilton, A. J. and Baulcombe, D. C. 1999. A species of small antisense RNA in posttranscriptional gene silencing in plants. Science 286: 950-952.

Higgins, D. G. and Sharp, P. M. (1988) Gene 73(1):237-44.

Higgins, D. G. and Sharp, P. M. (1989) Comput Appl Biosci. 5(2):151-3.

Horiguchi, G. 2004. RNA silencing in plants: a shortcut to functional analysis. Differentiation 72: 65-73.

Huang X. et al. (1992) Comput. Appl. Biosci. 8(2):155-65.

Jin, Q., D. Walters, G. M. Corderio, R. J. Henry and R. F. Reinke. 2003. A single nucleotide polymorphism (SNP) markers for fragrance in rice by analysis of the rice genome sequence. Mol. Breed. 9; 245-250.

Johnston and Tang, "Gene gun transfection of animal cells and genetic immunization," Methods Cell. Biol, 43(A): 353-365, 1994.

Jorgensen et al., Mol. Gen. Genet, 207:471, 1987.

Kadam, B. S, and V. K. Patankar. 1938. Inheritance of aroma in rice. India J. Genet. Breed. 40:327-329

Kaiser et al., "Amphiphilic secondary structure: design of peptide hormones." Science, 223(4633):249-255, 1984.

Klee et al., Bio/Technology, 3:637-642, 1985.

Klein et al., Nature, 327:70, 1987.

Klein et al., Proc. Natl. Acad. Sci. USA, 85:8502-8505, 1988.

Kuby, In: Immunology 2nd Edition, W. H. Freeman & Company, NY, 1994.

Lanceras, J. C., Z. L. Huang, O, Naivikul, A. Vanavichit, V. Ruanjaichon and S. Tragoonrung. 2000. Mapping of genes for cooking and eating qualities in That jasmine rice (KDML 105). DNA Res 7: 93-101.

Livingstone, J. R., Yoshida, I., Tarui, Y., Hirooka, K., Yamamoto, Y., Tsutui, N., and Hirasawa, E. (2002). Purification and properties of aminoaldehyde dehydrogenase from Avena sativa. J Plant Res 115, 393-400.

Lorieux, M., M. Petrov, N. Huang, E. Guiderdoni, A. Ghesquiere. 1996. Aroma in rice: Genetic analysis of a quantitative trait. Theo. Appl. Genet. 93:1145-1151.

Lorz et al., Mol. Gen. Genet., 199:178, 1985.

Lu, Xiao, Clapp, Li, Broxmeyer, "High efficiency retroviral mediated gene transduction into single isolated immature and replatable CD34(3+) hematopoietic stem/progenitor cells from human umbilical cord blood," J. Exp. Med, 178(6):2089-2096, 1993.

Maga, J. A. 1984. Rice product volatile: A review. J. Agric. Food. Chem. 32:924-970.

Mahatheeranont, S., S. Promdang and A. Chaimpiriyakul. 1995. Volatile aroma compound of Khao Dawk Mali 105. Kasetsart J. (Nat. sci.) 29:508-514

Maloy et al., In: Microbial Genetics, 2nd Edition, Jones and Bartlett Publishers, Boston, Mass., 1994.

Marcotte et al., Nature, 335:454, 1988.

Matzke, M. Matzke, A. J. M. and Kooter, J. M. 2001. RNA: Guiding gene silencing. Science 293: 1080-1083.

McCabe et al., Biotechnology, 6:923, 1988.

Miki, D., and Shimamoto, K. (2004). Simple RNAi Vectors for Stable and Transient Suppression of Gene Function in Rice. Plant Cell Physiol. 45(4), 490-495.

Murashige, T., and Skoog, F. (1962). A revised medium for rapid growth and bioassays with tobacco tissue cultures. Physiol Plant 15, 473-497.

Nagamura Y, Antonio B A, Sasaki T. Rice molecular genetic map using RFLPs and its applications. Plant Mol Biol. 1997 September; 35(1-2):79-87. Review.

Nagsuk et al., 2004 Identification of 2-acetyl-1-pyrroline, the principal aromatic rice flavor compound in fungus cultures. Proceedings: The 2nd International Conference on Medicinal Mushroom and The International Conference on Biodiversity and Bioactive Compounds, 17-19 July, 2003, PEACH, Pattaya, Thailand, p 395-400.

Needleman, S. B. and Wunsch, C. D. (1970) J. Mol. Biol. 48:443-453.

Nimlek, E. 1999. Development of callus culture in four aromatic rices and gene transformation in Khao Dawk Mali 105. M. S. Thesis, Kasetsart University.

Omirulleh et al., Plant Molecular Biology, 21:415-428, 1993.

Paule, C. M. and Powers. 1989. Sensory and chemical examination of aromatic and nonaromatic rices. J. Food Sci. 54: 343-346.

Pearson W R. Using the FASTA program to search protein and DNA sequence databases. Methods Mol Biol. 1994; 24:307-31.

Pearson, W. R., Lipman, D. J., (1988) Proc Natl Acad Sci U.S.A. 85:2444-8.

Petrivalský , M., Brauner, F.e., Luhová , L., Gagneul, D., and Sebela, M. (2007). Aminoaldehyde dehydrogenase activity during wound healing of mechanically injured pea seedlings. Journal of Plant Physiology 164 1410-1418.

Petrov, M., M. Danzart, P. Giampaoli, J. Faure, and H. Richard. 1995. Rice aroma analysis. Discrimination between a scented and a non-scented rice. Sci. Aliments 16:339-352.

Plonjarean, S., Phutdhawong, W., Siripin, S., Suvannachai, N., and Sengpracha, W. (2007). Flavour compounds of the Japanese vegetable soybean "Chakaori" growing in Thailand. Mj. Int. J. Sci. Tech 1, 1-9.

Potrykus, I., Harns, C. T., and Lorz, H. (1979). Callus formation from cell culture protoplasts of corn (Zea mays L.). Theor Appl Genet 54, 209-214.

Potrykus et al., Mol. Gen. Genet., 199:183, 1985.

Prokop and Bajpai, "Recombinant DNA Technology I," Ann. N.Y. Acad. Sci., Vol. 646, 1991.

Pulak R, Anderson P. "mRNA surveillance by the Caenorhabditis elegans smg genes". Genes Dev. 1993 October; 7(10):1885-97.

Rogers et al., Methods Enzymol., 153:253-277, 1987.

Romanczyk, J. R. L. J, C. A. McClelland, L. S. Post and W. Martin Aitken. 1995. Formation of 2-acetyl-1-pyrroline by several Bacillus cereus strains isolated from cocao fermentation boxes. J. Agrc. Food chem. 43 (2): 469-475.

Sakata, K., Nagamura, Y., Numa, H., Antonio, B. A., Nagasaki, H., Idonuma, A., Watanabe, W., Shimizu, Y., Horiuchi, I., Matsumoto, T., Sasaki, T. & Higo, K.: "Rice-GAAS: an automated annotation system and database for rice genome sequence", Nucleic Acids Res., 30: 98-102 (Jan. 2002).

Samoylov, V. M., Tucker, D. M., Thibaud-Nissen, F., and Parrott, W. A. (1998). A liquid-medium-based protocol for rapid regeneration from embryogenic soybean cultures. Plant Cell Rep. 18, 49-54.

Schieberle, P. 1991. Primary odorants in popcorn. J. Agric. Food Chem. 39 (6): 1141-1144.

Schieberle, P., and Wener, G. (1991). Potent odorants of the wheat bread crumb. Z. Lebensm.-Unters. Forsch 192, 130-135.

Sebela, M., Luhová , L., Brauner, F., Galuszka, P., Radová , A., and Pec, P. (2001). Light microscopic localization of aminoaldehyde dehydrogenase activity in plant tissues using nitroblue tetrazolium-based staining method. Plant Physiol Biochem. Genet. 39, 831-839.

Segal, In: Biochemical Calculations, 2nd Edition, John Wiley & Sons, New York, 1976.

Seitz, L. M., R. L. Wright, R. D. Waniska and L. W. Rooney. 1993. Contribution of 2-acetyl-1-pyrroline to odors from wetted ground pearl millet. J. Agric. Food Chem. 41(6): 955-958.

Shelp, B. J., Bown, A. W. and Mclean, M. D. (1999) Metabolism and functions of gamma-aminobutyric acid. Trends Plant Sci. 4: 446-452.

Smith, T. F. and Waterman, M. S. (1981) J. Mol. Biol. 147: 195-197.

Sood, B. C., E. A. Siddiq. 1978. A rapid technique for scent determination in rice. Indian J. Genet. Plant Breed. 38:268-271

Spielmann et al., Mol. Gen. Genet., 205:34, 1986.

Sriseadka, T., Wongpornchai, S., and Kitsawatpaiboon, P. (2006). Rapid Method for Quantitative Analysis of the Aroma Impact Compound, 2-Acetyl-1-pyrroline, in Fragrant Rice Using Automated Headspace Gas Chromatography. J. Agric. Food Chem. 54, 8183-8189.

P. Suprasanna, T. R. Ganaphthi, N. K. Ramaswamy, K. K. Surendranathan, P. S. Rao, Aroma synthesis in cell and callus cultures of rice, Rice Genet. Newsl. 15 (1998) 123-125.

P. Suprasarma, G. Bharati, T. R. Ganaphthi, V. A. Bapat, Aroma in rice: effects of proline supplementation and immobilization of callus cultures, Rice Genet. Newsl. 19 (2002) 9-11.

Takashi, T., T. Kurata and H. Kaio. 1980. Volatile components after cooking rice milled to different degrees. Agric. Biol. Chem. 44(4): 835-840.

Tanchotikul, U., and T. C. Y. Hsieh. 1991. An improved method for quantification of 2-acetyl-1-pyrroline, a "popcorn'—like aroma, in aromatic rice by high-resolution gas chromatography/mass spectrophotometry/selective ion monitoring. J. Agric. Food Chem. 39:944-947.

Till, Bradley J. Reynolds, S H. Greene, E A. Codomo, C A. Enns, L C. Johson, J E. Burtner, C. Odden, A R. Yound, K. Taylor, N E. Henikoff, J G. Comai, L. and Henikoff, S. 2003. Large-scale discovery of induced point mutations with high-throughput TILLING. Genome Research 13:524-530

Toriyama et al., Theor. Appl. Genet., 73:16, 1986.

Tylichová M, Kope•ný D, Snégaroff J and Šebela M. (2007) Aminoaldehyde dehydrogenases: has the time now come for new interesting discoveries? Curr Topics Plant Biol. 8: 45-70.

Uchimiya et al., Mol. Gen. Genet., 204:204, 1986.

Vasil et al., "Herbicide-resistant fertile transgenic wheat plants obtained by microprojectile bombardment of regenerable embryogenic callus," Biotechnology, 10:667-674, 1992.

Vasil, Biotechnology, 6:397, 1988.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," Proc. Natl. Acad. Sci. USA, 89(13):6099-6103, 1992.

S. Wanchana, W. Kamolsukyunyong, S. Ruengphayak, T. Toojinda, S. Tragoonrung, A. Vanavichit, A rapid construction of a physical contig across a 4.5 cM region for rice grain aroma facilitates marker enrichment for positional cloning, Plant Sc. (in press).

Weretilnyk, E. and Hanson A. D. 1990. Molecular cloning of a plant betaine-aldehyde dehydrogenase, an enzyme implicated in adaptation to salinity and drought. Proc. Natl. Acad. Sci. 87: 2745-2749.

Widjaja, R., Craske, J., and Wootton, M. (1996). Comparative studies on volatile components of non-fragrant and fragrant rices. J Sci Food Agric 70, 151-161.

Wong and Neumann, "Electric field mediated gene transfer," Biochim. Biophys. Res. Commun. 107(2):584-587, 1982.

S. Wongpornchai, T. Sriseadka, S. Choonvisase, Identification and quantitation of the rice aroma compound, 2-acetyl-1-pyrroline, in bread flowers (Vallaris glabra Ktze), J. Agric. Food Chem. 51 (2003) 457-462.

Xing, S. G., Jun, Y. B., Hau, Z. W., and Liang, L. Y. (2007). Higher accumulation of g-aminobutyric acid induced by salt stress through stimulating the activity of diamine oxidases in Glycine max (L.) Merr. roots. Plant Physiology and Biochemistry 45, 560-566.

Yajima, I., T. Yanai, and M. Nakamura. 1978. Volatile flavor components of cooked rice. Agric. Biol. Chem. 42: 1229.

Yamada et al., Plant Cell Rep, 4:85, 1986.

Yanjuan, D., H. Zhang and S. Shi. 1992. Genetic studies of aroma in the elite cytoplasmic male sterile (CMS) aromatic Japonica line shanghai A. Int. Rice Res Newsl. 17:2.

Yoshihashi, T. 2002. Quantitative analysis on 2-acetyl-1-pyrroline of an aromatic rice by stable isotope dilution method and model studies on its formation during cooking. Food Sci. 67 (2): 619-622.

Yoshihashi, T., Huong, N. T. T., and Inatomi, H. (2002). Precursors of 2-Acetyl-1-pyrroline, a Potent Flavor Compound of an Aromatic Rice Variety. J. Agric. Food Chem. 50, 2001-2004.

Zatloukal, Wagner, Cotten, Phillips, Plank, Steinlein, Curiel. Birnstiel, "Transferrinfection: a highly efficient way to express gene constructs in eukaryotic cells," Ann. N.Y. Acad. Sci., 660:136-153, 1992.

We claim:

1. A method for increasing the level of 2-acetyl-1-pyrroline in a soybean plant, comprising:
    generating transgenic soybean plants having a reduced level of an mRNA, wherein the mRNA is encoded by a nucleic acid comprising SEQ ID NO: 101 and wherein the mRNA level is reduced by expression of said nucleic acid in an antisense orientation, or by expression of an RNA interference (RNAi) construct comprising at least a fragment of 20 contiguous nucleotides of said nucleic acid, and
    selecting the resulting transgenic soybean plants having an increase in the level of 2-acetyl-1-pyrroline relative to a control, non-transgenic soybean plant.

2. The method of claim 1, wherein said mRNA level of said nucleic acid is reduced by expressing said nucleic acid in the antisense orientation.

3. The method of claim 1, wherein said mRNA level of said nucleic acid is reduced by expressing said nucleic acid in a RNA interference (RNAi) construct.

4. The method of claim 1, wherein said RNAi construct comprises 441 bp of SEQ ID NO: 101.

5. The method of claim 1, wherein the increase in the level of 2-acetyl-1-pyrroline is associated with an increase in aromatic fragrance of the transgenic soybean plant.

6. The method of claim 1, wherein the non-transgenic soybean plant is of a non-aromatic variety.

* * * * *

SEQUENCE LISTING

```
<160> NUMBER OF SEQ ID NOS: 112

<210> SEQ ID NO 1
<211> LENGTH: 5857
<212> TYPE: DNA
<213> ORGANISM: Oryza sativa

<400> SEQUENCE: 1
atggccacgg cgatcccgca gcggcagctc ttcgtcgccg gcgagtggcg cgccccgcg      60 ctcggccgcc gcctccccgt cgtcaacccc gccaccgagt ccccatcgg taccctcctc     120 ttcaccctct ccaccctctg cttctgcctc tgattagcct ttttgttgtt gttgttgttg     180
ctgctgtttt ttgcgtgtcg gtgcgcaagc gagatcccgg cgggcacggc ggaggacgtg     240
gacgcggcgg tggcggcggc gcgggaggcg cttaaaaaga acccgggccg cgactgggcg     300
cccgcgccgg gcgccgtccg ggccaagtac attcgcgcaa tcgctgacaa agtagggtgg     360
tgactaccct tatcagcctg cccgttttaa cgggagcctt gtgcgtgtgt tccgtacagg     420
gggaggagct ccgcgtggct ctccagtagg tttttgagcc ccaaatcgat cgatatgctc     480
tagttttaag tttgctgctt aaattcctca agggtttagt ttgcaaccaa atccttattt     540
tagcttcggt ataagccccc catatgatgt gcgtgcgtcg gcatcggaag tgcgtatcct     600
ctgttctgga ctaggaattg gccataggtt gatcgacagt tcgagtattc tgcttctgtt     660
tggaataagt tggaagcatg gctgattgtg tatctggatg ctgtttttgt ggtgattcgt     720
ttcaagctct tgttaattga tgggttcaag cggagagggt gcgcaacaac aagtgtatat     780
ggctcacggc catgggtgtg cacatttgat tggtgcgcaa caacaagtgt atattgtgtg     840
tgcttcgtta gttggcaggt cctagtcact aaatcactat tggattggta ctagctactt     900
ttgtgccttg acgatgggac tggattacta gccttttggt tgcctttgtg gtattccgtt     960
gttatgggcc tgttgatgga tggatccctt taatttctag tgccaaatgc atgctagatt    1020
```

```
tctcacagtt tttctcttca ggttatattt ctcgtatttc cttttcctaa aggattgctt    1080
tttcatgtat tttctggcat ataggttta ttattattat tattctccag aacaagatta    1140
cccatattat ggatcactag tgtacacttt tttggatgaa aaacctactt actgaaagta    1200
aaacagtgac cagtgcacac tttacttgaa ctgtcaaacc atcaatttc tagcaaagca     1260 ggggatgcta gccttccagt ctaaatgaca gtaaactact atacttttgt ccgtaggttt    1320
ggaaatatgc taatttctat cataaaaatt ttcatggcat atgcgagcat tttatgatca    1380
ccttttccct ttttcttcag ataatcgaga ggaaatctga gctggctaga ctagagacgc    1440
ttgattgtgg gaagcctctt gatgaagcag catgggacat ggtatgtggc cagttatcca    1500
ctgtatgaat atgtagttgc ctacacagca atctttcctg aacatgaatc ctgatgtatg    1560
atattccatt tgtcaggacg atgttgctgg atgctttgag tactttgcag atcttgcaga    1620
atccttggac aaaaggcaaa atgcacctgt ctctcttcca atggaaaact taaatgcta    1680 tcttcggaaa gagcctatcg gtgtagtgg gttgatcaca ccttggtatt tcacatttt     1740 ctctcatcct gcgcttatat ttatttatga cccaagcatg gtactaaata gtactagtaa    1800
catgcatata ctgaatgagt ttacaacttt acatgatttt tttgaactat gaaagttgaa    1860
gacatttgag attttattcc tcttctcttg tgcaaacata ttattgtctc acaaattgta    1920
cctagcagct actctctccg tttcatatta taagtcgttt gactttttc ctagtcaaaa     1980 tgtgttaagt ttgaccaagt ttatagaaaa atttagcaac atctaaaata tcaaagtcat    2040
gttttagtgt tttttcaggc tctcatgtaa gcaattttga tgtgccctct cctttcttct    2100
taatataatg atacacagct cttgtgtatt caaaggaata tatatatata tatatatata    2160
taatgataca cacctctcct ccgtgttaat gcagctcatt tgttctgtcc cggttcaaat    2220
atctattttt ctcatatgtt gtcagcatga ttcacttaat ttagtatata gaagatgcca    2280
ttatttatgt ctggaatctt actgcagaag ggaaaacaat tgataacgga attgattgca    2340
ttctaatttg ttgtttcttt gttatgttct tatcgacaat tacaaatttg attctgagaa    2400
tcatgttcgg gatgtgtatt tctactgcag gaactatcct ctcctgatgg caacatggaa    2460
ggtagctcct gccctggctg ctggctgtac agctgtacta aaaccatctg aattggcttc    2520
cgtgtaagtt taacatgtta acttgttaat gtcatatccca tgctagttgc aatgacattt    2580
gattttaaaa tgttgtggca tgtccatgct gcaagcaatg taatttgaaa tctctctcta    2640
tcattaatta ccaggacttg tttggagctt gctgatgtgt gtaaagaggt tggtcttcct    2700
tcaggtgtgc taaacatagt gactggatta ggttctgaag ccggtgctcc tttgtcatca    2760
caccctggtg tagacaaggt acagctattc ctcctgtaat catgtatacc ccatcaatgg    2820
aaatgatatt cctctcaata catggtttat gttttctgtt aggttgcatt tactgggagt    2880
tatgaaactg gtatatattt cagctgctcc tatggttaag gtttgtttcc aaatttctgt    2940 ggatatttt tgttctcttt ctactaactc tctattatca attctcaatg ttgtcctttt     3000
cttttaactc ctttacttt tagaattgtg atcaagacac tttgagcatc attctagtag     3060
ccagttctat cctgtttctt accttttat ggttcgtctt ttcttgacag cctgtttcac     3120
tggaacttgg tggaaaaagt cctatagtgg tgtttgatga tgttgatgtt gaaaaggta    3180 catgccactt gctatgatta actaattctg aagtgcggga cttttgtaaag cacttaactg    3240 agctggatgc tagaccccca aaagcccttt ttggtgtctt gggcttgttg cagaaatact    3300
ggtcccagac gagcaggatg caagaaaatt aactactttt gccactgatt agtatttctt    3360
```

```
agaagttaca cctcaaggat tagcaatact ttcttaaaat gtgctattga ttaaaaagat    3420
gtcctgtatt attttgagca gatcttgtac tggttgatcg gcttgcatga aaatattgtt    3480
gaggattata atgccatgcc aactgagtaa agaaaagagt tgtaaaatat gttatgcaac    3540
atgaatatat atgtgatttc attttcctt tttcttttcg tggcaaggaa ggcagttagg    3600
aaggactgat gtgaaaagca caagtactat tcttagttct ggaaaactgt gttctttatt    3660
ttcctaacta caattcacct tgattagtca gtaacttgat attggcaatt ctagctgatt    3720
atgaattctg tttatatttc actaattttg aatctttaat tacatttat ggttgaaatt    3780
taacgttttg tctggttatg gactctgttt gtattcactc aatttggatc ttccattaga    3840
tttcattgtt ggtccttctt cttgtacagc tgttgagtgg actctctttg gttgcttttg    3900
gaccaatggc cagatttgca gtgcaacatc gcgtcttatt cttcatgtaa gcattgaata    3960
tatccgtcaa tcataatcta ttgttgtact tgattttttt tctgatcaac tcctgagttc    4020
agattattat atgatgccat tactattgca cagagcgaat aaaattgtat ttatgcacag    4080
catgtattt gagtaatata tgcattgcct attatttaat atatagattg tagcacttaa    4140
ttttgtgtcc atgtctctat gatgtttatt actttattat tgccggcatg aagcaacttt    4200
gaactctatg ttgatcttga actaaaattg aaattaattg gctattgct attaatgata    4260
tagctttcag cttcttgctc ctgaccatga agttttgca gaaaaaaatc gctaagaat    4320
ttcaagaaag gatggttgca tgggccaaaa atattaaggt gtcagatcca cttgaagagg    4380
gttgcaggct tgggcccgtt gttagtgaag gacaggtacc acatgtaaac tttttctaaa    4440
ttcaaaaaag aaatgccact gatcaatggt aggtccttcc aagccttatt gctggattgt    4500
tgcactgttt tgtcaatttt gtgtaatata gttctgaatg aattagtcgg tgtatgctct    4560
tgctagttgc tagtatgtgg tacagggtct tcctactttg agcaaattcg tgttaaaatg    4620
cattgatgaa aaggccacct ttccgtaggt ttatcttgtc ataatttaaa ccccaataaa    4680
attttaattt tttgttttga ccccatggca ctttaatgaa atcacttagc catgagcttt    4740
tgtatatatt ttcaaagcac cagaatgttt agatggtttg ttggaaatct tacacatcct    4800
attgccttgt gtcagtatga aagattaag caatttgtat ctaccgccaa aagccaaggt    4860
gctaccattc tgactggtgg ggttagaccc aaggtaataa tctactacac ggttgtatat    4920
ataggtaccc acatatcatt atgaagtaga aataatcttg tatgtttttg tcagcatctg    4980
gagaaaggtt tctatattga acccacaatc attactgatg tcgatacatc aatgcaaatt    5040
tggagggaag aagttttgg tccagtgctc tgtgtgaaag aatttagcac tgaagaagaa    5100
gccattgaat tggccaacga tactcagtga gttttttttt taatacagtt cattgtcctg    5160
ttcaatcttg cagcatatgt atatactctg tggcatatga acttattctg ctactactac    5220
ttttgatagt tatggtctgg ctggtgctgt gctttccggt gaccgcgagc gatgccagag    5280
attaactgag gtatatccaa gtgaaggggg ttggcattgt ttgattcata tgacatggtt    5340
gcatcaagct gatattcaag aatctcattt attacttgca ttctatgcat ctccagttct    5400
tccctggact ccggtcaatg ttaatatagt ttgtttgcta gtagtatgct actccaatta    5460
agttgctctt cacttccaca tcatctgatc catgacttta tatttgaccc ctttttttg    5520
caaagagag ggaaatactt aacgaaaatt tcctactgca ggagatcgat gccggaatta    5580
tctgggtgaa ctgctcgcaa ccctgcttct gccaagctcc atgggcggg aacaagcgca    5640
gcggctttgg acgcgagctc ggagaagggt gggtagcaca caacaatctc actttaaaac    5700
accatttcga tcgtctgatg atctcgacct gacatcatgc ctttggtatt ttcattcact    5760
```

```
tttcagggc attgacaact acctaagcgt caagcaagtg acggagtacg cctccgatga    5820
gccgtgggga tggtacaaat ccccttccaa gctgtaa                            5857

<210> SEQ ID NO 2
<211> LENGTH: 1504
<212> TYPE: DNA
<213> ORGANISM: Oryza sativa

<400> SEQUENCE: 2
atggccacgg cgatcccgca gcggcagctc ttcgtcgccg gcgagtggcg cgccccgcg      60 ctcggccgcc gctcccccgt cgtcaacccc gccaccgagt cccccatcgg cgagatcccg    120
gcgggcacgg cggaggacgt ggacgcggcg gtggcggcgg cgcgggaggc gcttaaaaag    180
aacccgggcc gcgactgggc gcccgcgccg ggcgccgtcc gggccaagta cattcgcgca    240
atcgctgaca aaataatcga gaggaaatct gagctggcta gactagagac gcttgattgt    300
gggaagcctc ttgatgaagc agcatgggac atggacgatg ttgctggatg ctttgagtac    360
tttgcagatc ttgcagaatc cttggacaaa aggcaaaatg cacctgtctc tcttccaatg    420
gaaaacttta atgctatct tcggaaagag cctatcggtg tagttgggtt gatcacacct      480
tggaactatc ctctcctgat ggcaacatgg aaggtagctc ctgccctggc tgctggctgt    540
acagctgtac taaaccatc tgaattggct tccgtgactt gtttggagct tgctgatgtg     600
tgtaaagagg ttggtcttcc ttcaggtgtg ctaaacatag tgactggatt aggttctgaa    660
gccggtgctc ctttgtcatc acaccctggt gtagacaagg ttgcatttac tgggagttat    720
gaaactggta tatttcag ctgctcctat ggttaagcct gtttcactgg aacttggtgg       780
aaaaagtcct atagtggtgt tgatgatgt tgatgttgaa aaagctgttg agtggactct     840
ctttggttgc ttttggacca atggccagat ttgcagtgca catcgcgtc ttattcttca     900 taaaaaatc gctaaagaat ttcaagaaag gatggttgca tgggccaaaa atattaaggt     960
gtcagatcca cttgaagagg gttgcaggct tgggcccgtt gttagtgaag acagtatga    1020 gaagattaag caatttgtat ctaccgccaa aagccaaggt gctaccattc tgactggtgg    1080
ggttagaccc aagcatctgg agaaaggttt ctatattgaa cccacaatca ttactgatgt    1140
cgatacatca atgcaaattt ggagggaaga agttttggt ccagtgctct gtgtgaaaga    1200
atttagcact gaagaagaag ccattgaatt ggccaacgat actcattatg gtctggctgg    1260
tgctgtgctt tccggtgacc gcgagcgatg ccagagatta actgaggaga tcgatgccgg    1320
aattatctgg gtgaactgct cgcaaccctg cttctgccaa gctccatggg gcgggaacaa    1380
gcgcagcggc tttggacgcg agctcggaga aggggggcatt gacaactacc taagcgtcaa    1440
gcaagtgacg gagtacgcct ccgatgagcc gtggggatgg tacaaatccc cttccaagct    1500
gtaa                                                                1504

<210> SEQ ID NO 3
<211> LENGTH: 251
<212> TYPE: PRT
<213> ORGANISM: Oryza sativa

<400> SEQUENCE: 3

Met Ala Thr Ala Ile Pro Gln Arg Gln Leu Phe Val Ala Gly Glu Trp
 1               5                  10                  15

Arg Ala Pro Ala Leu Gly Arg Arg Leu Pro Val Val Asn Pro Ala Thr
            20                  25                  30
```

```
Glu Ser Pro Ile Gly Glu Ile Pro Ala Gly Thr Ala Glu Asp Val Asp
         35                  40                  45

Ala Ala Val Ala Ala Ala Arg Glu Ala Leu Lys Lys Asn Pro Gly Arg
 50                  55                  60

Asp Trp Ala Pro Ala Pro Gly Ala Val Arg Ala Lys Tyr Ile Arg Ala
 65                  70                  75                  80

Ile Ala Asp Lys Ile Ile Glu Arg Lys Ser Glu Leu Ala Arg Leu Glu
                 85                  90                  95

Thr Leu Asp Cys Gly Lys Pro Leu Asp Glu Ala Ala Trp Asp Met Asp
                100                 105                 110

Asp Val Ala Gly Cys Phe Glu Tyr Phe Ala Asp Leu Ala Glu Ser Leu
            115                 120                 125

Asp Lys Arg Gln Asn Ala Pro Val Ser Leu Pro Met Glu Asn Phe Lys
130                 135                 140

Cys Tyr Leu Arg Lys Glu Pro Ile Gly Val Val Gly Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Thr Ala Val Leu Lys Pro Ser Glu Leu Ala Ser Val
            180                 185                 190

Thr Cys Leu Glu Leu Ala Asp Val Cys Lys Glu Val Gly Leu Pro Ser
        195                 200                 205

Gly Val Leu Asn Ile Val Thr Gly Leu Gly Ser Glu Ala Gly Ala Pro
210                 215                 220

Leu Ser Ser His Pro Gly Val Asp Lys Val Ala Phe Thr Gly Ser Tyr
225                 230                 235                 240

Glu Thr Gly Ile Tyr Phe Ser Cys Ser Tyr Gly
                245                 250

<210> SEQ ID NO 4
<211> LENGTH: 5859
<212> TYPE: DNA
<213> ORGANISM: Oryza sativa

<400> SEQUENCE: 4
atggccacgg cgatcccgca gcggcagctc ttcgtcgccg gcgagtggcg cgccccgcg      60 ctcggccgcc gctcccccgt cgtcaacccc gccaccgagt cccccatcgg taccctcctc    120
ttcaccctct ccaccctctg cttctgcctc tgattagcct ttttgttgtt gttgttgttg    180
ctgctgtttt ttgcgtgtcg gtgcgcaggc gagatcccgg cgggcacggc ggaggacgtg    240
gacgcggcgg tggcggcggc gcgggaggcg ctgaagagga accggggccg cgactgggcg    300
cgcgcgccgg cgccgtccg ggccaagtac ctccgcgcaa tcgcggccaa ggtagggtgg     360
tgactacccc caccccccc cccccccaa cgcgacccgc gtgcgtgtgt tccgtacagg      420
gggaggagct ccgcgtggct ctccagtagg tttttgagcc caaatcgat cgatatgctc     480 tagttttaag tttgctgctt aaattcctca agggtttagt ttgcaaccaa atccttattt    540
tagcttcggt ataagccccc catatgatgt gcgtgcgtcg catcggaag tgcgtatcct     600 ctgttctgga ctaggaattg gccataggtt gatcgacagt tcgagtattc tgcttctgtt    660
tggaataagt tggaagcatg gctgattgtg tatctggatg ctgttttttgt ggtgattcgt   720 ttcaagctct tgttaattga tgggttcaag cggagagggt gcgcaacaac aagtgtatat    780
ggctcacggc catgggtgtg cacatttgat tggtgcgcaa caacaagtgt atattgtttg    840
tgtgcttcgt tagttggcag gtcctagtca ctaaatcact attggattgg tactagttac    900
```

```
ttttgtgcct tgacgatggg actggattac tagccttttg gttgcctttg tggtattccg      960
ttgttatggg cctgttgatg gatggatccc tttaatttct agtgccaaat gcatgctaga     1020
tttctcacag ttttctctt caggttatat ttctcgtatt tccttttcct aaaggattgc     1080
tttttcatgt attttctggc atatataggt tattattatt attattctcc agaacaagat     1140
tacccatatt atggatcact agtgtacact ttttggatg aaaaacctac ttactgaaag      1200
taaaacagtg accagtgcac actttacttg aactgtcaaa ccatcaattt tctagcaaag     1260
caggggatgc tagccttcca gtctaaatga cagtaaacta ctatacttt gtccgtaggt      1320 ttggaaatat gctaatttct atcataaaaa ttttcatggc atatgcgagc attttatgat     1380
caccttttcc cttttcttc agataatcga gaggaaatct gagctggcta gactagagac     1440
gcttgattgt gggaagcctc ttgatgaagc agcatgggac atggtatgtg ccagttatc     1500 cactgtatga atatgtagtt gcctacacag caatctttcc tgaacatgaa tcctgatgta    1560
tgatattcca tttgtcagga cgatgttgct ggatgctttg agtactttgc agatcttgca    1620
gaatccttgg acaaaaggca aaatgcacct gtctctcttc caatggaaaa ctttaaatgc    1680
tatcttcgga aagagcctat cggtgtagtt gggttgatca cccttggta tttcacattt     1740 ttctctcatc ctgcgcttat atttatttat gacccaagca tggtactaaa tagtactagt    1800
aacatgcata tactgaatga gtttacaact ttacatgatt tttttgaact atgaaagttg    1860
aagacatttg agattttatt cctcttctct tgtgcaaaca tattattgtc tcacaaattg    1920
tacctagcag ctactctctc cgtttcatat tataagtcgt ttgactttt tcctagtcaa     1980 aatgtgttaa gtttgaccaa gtttatagaa aaatttagca acatctaaaa tatcaaagtc    2040
atgttttagt gtttttcag gctctcatgt aagcaatttt gatgtgccct ctcctttctt    2100
cttaatataa tgatacacag ctcttgtgta ttcaaggaa aatatatata tataatga      2160 tacacacctc tcctccgtgt taatgcagct catttgttct gtcccggttc aaatatctat    2220
ttttctcata tgttgtcagc atgattcact taatttagta tatagaagat gccattattt    2280
atgtctggaa tcttactgca gagggaaaa caattgataa cggaattgat tgcattctaa     2340
tttgttgttt ctttgttatg ttcttatcga caattacaaa tttgattctg agaatcatgt    2400
tcgggatgtg tatttctact gcaggaacta tcctctcctg atggcaacat ggaaggtagc    2460
tcctgccctg gctgctggct gtacagctgt actaaaacca tctgaattgg cttccgtgta    2520
agtttaacat gttaacttgt taatgtcata cccatgctag ttgcaatgac atttgatttt    2580
aaaatgttgt ggcatgtcca tgctgcaagc aatgtaattt gaaatctctc tctatcatta    2640
attaccagga cttgtttgga gcttgctgat gtgtgtaaag aggttggtct tccttcaggt    2700
gtgctaaaca tagtgactgg attaggttct gaagccggtg ctccttttgtc atcacaccct   2760 ggtgtagaca aggtacagct attcctcctg taatcatgta taccccatca atggaaatga    2820
tattcctctc aatacatggt ttatgttttc tgttaggttg catttactgg gagttatgaa    2880
actggtaaaa agattatggc ttcagctgct cctatggtta aggtttgttt ccaaatttct    2940 gtggatatt tttgttctct ttctactaac tctctattat caattctcaa tgttgtcctt    3000
ttcttttaac tcctttactt tttagaattg tgatcaagac actttgagca tcattctagt    3060
agccagttct atcctgtttc ttaccttttt atggttcgtc ttttcttgac agcctgtttc    3120
actgaaactt ggtggaaaaa gtcctatagt ggtgtttgat gatgttgatg ttgaaaaagg    3180
tacatgccac ttgctatgat taactaattc tgaagtgcgg gactttgtaa agcacttaac    3240
```

```
tgagctggat gctagacccc caaaagccct ttttggtgtc ttgggcttgt tgcagaaata    3300
ctggtcccag acgagcagga tgcaagaaaa ttaactactt ttgccactga ttagtatttc    3360
ttagaagtta cacctcaagg attagcaata ctttcttaaa atgtgctatt gattaaaaag    3420
atgtcctgta ttattttgag cagatcttgt actggttgat cggcttgcat gaaaatattg    3480
ttgaggatta taatgccatg ccaactgagt aaagaaaaga gttgtaaaat atgttatgca    3540
acatgaatat atatgtgatt tcattttttcc tttttctttt cgtggcaagg aaggcagtta    3600
ggaaggactg atgtgaaaag cacaagtact attcttagtt ctggaaaact gtgttcttta    3660
ttttcctaac tacaattcac cttgattagt cagtaacttg atattggcaa ttctagctga    3720
ttatgaattc tgtttatatt tcactaattt tgaatcttta attcattttt atggttgaaa    3780
tttaacgttt tgtctggtta tggactctgt ttgtattcac tcaatttgga tcttccatta    3840
gatttcattg ttggtccttc ttcttgtaca gctgttgagt ggactctctt tggttgcttt    3900
tggaccaatg gccagatttg cagtgcaaca tcgcgtctta ttcttcatgt aagcattgaa    3960
tatatccgtc aatcataatc tattgttgta cttgattttt tttctgatca actcctgagt    4020
tcagattatt atatgatgcc attactattg cacagagcga ataaaattgt atttatgcac    4080
agcatgtatt ttgagtaata tatgcattgc ctattattta atatatagat tgtagcactt    4140
aattttgtgt ccatgtctct atgatgttta ttactttatt attgccggca tgaagcaact    4200
ttgaactcta tgttgatctt gaactaaaat tgaaattaat tggcttattg ctattaatga    4260
tatagctttc agcttcttgc tcctgaccat gaaagttttg cagaaaaaaa tcgctaaaga    4320
atttcaagaa aggatggttg catgggccaa aaatattaag gtgtcagatc cacttgaaga    4380
gggttgcagg cttgggcccg ttgttagtga aggacaggta ccacatgtaa acttttttcta   4440 aattcaaaaa agaaatgcca ctgatcaatg gtaggtcctt ccaagcctta ttgctggatt    4500
gttgcactgt tttgtcaatt ttgtgtaata tagttctgaa tgaattagtc ggtgtatgct    4560
cttgctagtt gctagtatgt ggtacagggt cttcctactt tgagcaaatt cgtgttaaaa    4620
tgcattgatg aaaaggccac ctttccgtag gtttatcttg tcataattta acccccaata    4680
aaattttaat ttttttgtttt gaccccatgg cactttaatg aaatcactta gccatgagct    4740
tttgtatata ttttcaaagc accagaatgt ttagatggtt tgttggaaat cttacacatc    4800
ctattgcctt gtgtcagtat gagaagatta agcaatttgt atctaccgcc aaaagccaag    4860
gtgctaccat tctgactggt ggggttagac ccaaggtaat aatctactac acggttgtat    4920
atataggtac ccacatatca ttatgaagta gaaataatct tgtatgtttt tgtcagcatc    4980
tggagaaagg tttctatatt gaacccacaa tcattactga tgtcgataca tcaatgcaaa    5040
tttggaggga agaagttttt ggtccagtgc tctgtgtgaa agaatttagc actgaagaag    5100
aagccattga attggccaac gatactcagt gagtttttttt tttaatacag ttcattgtcc    5160
tgttcaatct tgcagcatat gtatatactc tgtggcatat gaacttattc tgctactact    5220
acttttgata gttatggtct ggctggtgct gtgctttccg gtgaccgcga gcgatgccag    5280
agattaactg aggtatatcc aagtgaaggg ggttggcatt gtttgattca tatgacatgg    5340
ttgcatcaag ctgatattca agaatctcat ttattacttg cattctatgc atctccagtt    5400
cttccctgga ctccggtcaa tgttaatata gtttgtttgc tagtagtatg ctactccaat    5460
taagttgctc ttcacttcca catcatctga tccatgactt tatatttgac cccttttttt    5520
tgcaaaagaa agggaaatac ttaacgaaaa tttcctactg caggagatcg atgccggaat    5580
tatctgggtg aactgctcgc aaccctgctt ctgccaagct ccatggggcg ggaacaagcg    5640
```

```
cagcggcttt ggacgcgagc tcggagaagg gtgggtagca cacaacaatc tcactttaaa    5700
acaccatttc gatcgtctga tgatctcgac ctgacatcat gcctttggta ttttcattca    5760
cttttcaggg gcattgacaa ctacctaagc gtcaagcaag tgacggagta cgcctccgat    5820
gagccgtggg gatggtacaa atccccttcc aagctgtaa                           5859

<210> SEQ ID NO 5
<211> LENGTH: 1512
<212> TYPE: DNA
<213> ORGANISM: Oryza sativa

<400> SEQUENCE: 5
atggccacgg cgatcccgca gcggcagctc ttcgtcgccg gcgagtggcg cgccccgcg     60 ctcggccgcc gctcccccgt cgtcaacccc gccaccgagt cccccatcgg cgagatcccg    120
gcgggcacgg cggaggacgt ggacgcggcg gtggcggcgg cgcgggaggc gctgaagagg    180
aaccggggcc gcgactgggc gcgcgcgccg gcgccgtcc gggccaagta cctccgcgca     240
atcgcggcca agataatcga gaggaaatct gagctggcta gactagagac gcttgattgt    300
gggaagcctc ttgatgaagc agcatgggac atggacgatg ttgctggatg ctttgagtac    360
tttgcagatc ttgcagaatc cttggacaaa aggcaaaatg cacctgtctc tcttccaatg    420
gaaaacttta aatgctatct tcggaaagag cctatcggtg tagttgggtt gatcacacct    480
tggaactatc ctctcctgat ggcaacatgg aaggtagctc ctgccctggc tgctggctgt    540
acagctgtac taaaaccatc tgaattggct tccgtgactt gtttggagct tgctgatgtg    600
tgtaaagagg ttggtcttcc ttcaggtgtg ctaaacatag tgactggatt aggttctgaa    660
gccggtgctc ctttgtcatc acaccctggt gtagacaagg ttgcatttac tgggagttat    720
gaaactggta aaagattat ggcttcagct gctcctatgg ttaagcctgt ttcactggaa    780
cttggtggaa aaagtcctat agtggtgttt gatgatgttg atgttgaaaa agctgttgag    840
tggactctct ttggttgctt ttggaccaat ggccagattt gcagtgcaac atcgcgtctt    900
attcttcata aaaaaatcgc taaagaattt caagaaagga tggttgcatg gccaaaaat    960 attaaggtgt cagatccact tgaagagggt tgcaggcttg ggcccgttgt tagtgaagga    1020
cagtatgaga agattaagca atttgtatct accgccaaaa gccaaggtgc taccattctg    1080
actggtgggg ttagacccaa gcatctggag aaaggtttct atattgaacc acaatcatt    1140 actgatgtcg atacatcaat gcaaatttgg agggaagaag ttttggtcc agtgctctgt    1200 gtgaaagaat ttagcactga agaagaagcc attgaattgg ccaacgatac tcattatggt    1260
ctggctggtg ctgtgctttc cggtgaccgc gagcgatgcc agagattaac tgaggagatc    1320
gatgccggaa ttatctgggt gaactgctcg caacccgtct tctgccaagc tccatggggc    1380
gggaacaagc gcagcggctt tggacgcgag ctcggagaag ggcgcattga caactaccta    1440
agcgtcaagc aagtgacgga gtacgcctcc gatgagccgt ggggatggta caaatcccct    1500
tccaagctgt aa                                                       1512

<210> SEQ ID NO 6
<211> LENGTH: 503
<212> TYPE: PRT
<213> ORGANISM: Oryza sativa

<400> SEQUENCE: 6

Met Ala Thr Ala Ile Pro Gln Arg Gln Leu Phe Val Ala Gly Glu Trp
 1               5                  10                  15
```

```
Arg Ala Pro Ala Leu Gly Arg Arg Leu Pro Val Val Asn Pro Ala Thr
            20                  25                  30

Glu Ser Pro Ile Gly Glu Ile Pro Ala Gly Thr Ala Glu Asp Val Asp
        35                  40                  45

Ala Ala Val Ala Ala Ala Arg Glu Ala Leu Lys Arg Asn Arg Gly Arg
50                  55                  60

Asp Trp Ala Arg Ala Pro Gly Ala Val Arg Ala Lys Tyr Leu Arg Ala
65                  70                  75                  80

Ile Ala Ala Lys Ile Ile Glu Arg Lys Ser Glu Leu Ala Arg Leu Glu
                85                  90                  95

Thr Leu Asp Cys Gly Lys Pro Leu Asp Glu Ala Ala Trp Asp Met Asp
            100                 105                 110

Asp Val Ala Gly Cys Phe Glu Tyr Phe Ala Asp Leu Ala Glu Ser Leu
        115                 120                 125

Asp Lys Arg Gln Asn Ala Pro Val Ser Leu Pro Met Glu Asn Phe Lys
130                 135                 140

Cys Tyr Leu Arg Lys Glu Pro Ile Gly Val Val Gly Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Thr Ala Val Leu Lys Pro Ser Glu Leu Ala Ser Val
            180                 185                 190

Thr Cys Leu Glu Leu Ala Asp Val Cys Lys Glu Val Gly Leu Pro Ser
        195                 200                 205

Gly Val Leu Asn Ile Val Thr Gly Leu Gly Ser Glu Ala Gly Ala Pro
210                 215                 220

Leu Ser Ser His Pro Gly Val Asp Lys Val Ala Phe Thr Gly Ser Tyr
225                 230                 235                 240

Glu Thr Gly Lys Lys Ile Met Ala Ser Ala Ala Pro Met Val Lys Pro
                245                 250                 255

Val Ser Leu Glu Leu Gly Gly Lys Ser Pro Ile Val Val Phe Asp Asp
            260                 265                 270

Val Asp Val Glu Lys Ala Val Glu Trp Thr Leu Phe Gly Cys Phe Trp
        275                 280                 285

Thr Asn Gly Gln Ile Cys Ser Ala Thr Ser Arg Leu Ile Leu His Lys
290                 295                 300

Lys Ile Ala Lys Glu Phe Gln Glu Arg Met Val Ala Trp Ala Lys Asn
305                 310                 315                 320

Ile Lys Val Ser Asp Pro Leu Glu Gly Cys Arg Leu Gly Pro Val
                325                 330                 335

Val Ser Glu Gly Gln Tyr Glu Lys Ile Lys Gln Phe Val Ser Thr Ala
            340                 345                 350

Lys Ser Gln Gly Ala Thr Ile Leu Thr Gly Gly Val Arg Pro Lys His
        355                 360                 365

Leu Glu Lys Gly Phe Tyr Ile Glu Pro Thr Ile Ile Thr Asp Val Asp
370                 375                 380

Thr Ser Met Gln Ile Trp Arg Glu Glu Val Phe Gly Pro Val Leu Cys
385                 390                 395                 400

Val Lys Glu Phe Ser Thr Glu Glu Ala Ile Glu Leu Ala Asn Asp
                405                 410                 415

Thr His Tyr Gly Leu Ala Gly Ala Val Leu Ser Gly Asp Arg Glu Arg
            420                 425                 430
```

```
Cys Gln Arg Leu Thr Glu Glu Ile Asp Ala Gly Ile Ile Trp Val Asn
            435                 440                 445
Cys Ser Gln Pro Cys Phe Cys Gln Ala Pro Trp Gly Gly Asn Lys Arg
        450                 455                 460
Ser Gly Phe Gly Arg Glu Leu Gly Glu Gly Gly Ile Asp Asn Tyr Leu
465                 470                 475                 480
Ser Val Lys Gln Val Thr Glu Tyr Ala Ser Asp Glu Pro Trp Gly Trp
                485                 490                 495
Tyr Lys Ser Pro Ser Lys Leu
            500
```

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gccatgccaa ctgagtaaag                                           20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
caattttatt cgctctgtgc                                           20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgcaacatcg cgtcttattc                                           20

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gcaactagca agagcataca cc                                        22

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acctgacatc atgcctttgg                                           20

<210> SEQ ID NO 12
<211> LENGTH: 20
<212> TYPE: DNA

```
<213> ORGANISM: Artificial Sequence
<220> FEATURE:
<223> OTHER INFORMATION: Primer

<400> SEQUENCE: 12
ccggtcatca gctaacttcc                                                    20

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
cccttcgtca taaatatac tagcaa                                              26

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcctccaaca tgctctttcg                                                    20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cagagaagtt tacgccgttg                                                    20

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
tttttaaata agatgaacgg tcaaa                                              25

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctctccaccc tctgcttctg                                                    20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ctctccgctt gaacccatc                                                     19
```

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gcatggctga ttgtgtatct g                                    21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ttccaaacct acggacaaaa g                                    21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ttcctcttct cttgtgcaaa c                                    21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cacggaagcc aattcagatg                                      20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ctatcctctc ctgatggcaa c                                    21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
tggctactag aatgatgctc aaag                                 24

<210> SEQ ID NO 25
<211> LENGTH: 20
<212> TYPE: DNA
<213> ORGANISM: Artificial Sequence
<220> FEATURE:

```
<223> OTHER INFORMATION: Primer

<400> SEQUENCE: 25 cctttttgtgt cgcttttgag                                                  20

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
aaaatagcct tcactcgttg c                                                 21

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccatcgattt cgagggtaac                                                   20

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
cgcatccgat aatatgttg                                                    19

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
gtaattagga gtacgactct cgtc                                              24

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gcttatagcc tactgtatcc tcctc                                             25

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
aattggttaa cccagcaagc                                                   20
```

```
<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
acattgtgaa acggaggaag                                                   20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gctataagcc agctgcaaac                                                   20

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
gcagttggta cggacttcg                                                    19

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
cctaaatatt tgacgccgtt g                                                 21

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tgaagaggag ggtaccgatg                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
caccactcca cacctgacac                                                   20

<210> SEQ ID NO 38
<211> LENGTH: 20
<212> TYPE: DNA
<213> ORGANISM: Artificial Sequence
<220> FEATURE:
<223> OTHER INFORMATION: Primer
```

<400> SEQUENCE: 38
gtacggaaca cacgcacaag                                           20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tgttgttgtt gttgctgctg                                           20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gccgtgagcc atatacactt g                                         21

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agctccagct cctcctcgat                                           20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tatctctcac cgaccccaaa                                           20

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
tgttgccatc aggagagga                                            19

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ctcttgatga agcagcatgg                                           20

<210> SEQ ID NO 45
<211> LENGTH: 21

-continued

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
cccagtaaat gcaaccttgt c    21

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ggcaacatgg aaggtagctc    20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ccatgcaacc atcctttctt    20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttatggcttc agctgctcct    20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
caatggcttc ttcttcagtg c    21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gcccgttgtt agtgaaggac    20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51

```
gtaccatccc cacggctcat                                              20

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
cgagcgatgc cagagatta                                               19

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
agcacatggc aaatcaaaca                                              20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
tgctcctttg tcatcacacc                                              20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tttccaccaa gttccagtga                                              20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ttcgctgcag aacagatgac                                              20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
ctgatggtta cgcgacaatt t                                            21

<210> SEQ ID NO 58
<211> LENGTH: 20
<212> TYPE: DNA
<213> ORGANISM: Artificial Sequence
```

```
<220> FEATURE:
<223> OTHER INFORMATION: Primer

<400> SEQUENCE: 58
atttgaaccg ggacagaaca                                          20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ttttgatgtg ccctctcctt                                          20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
tgggtaatct tgttctggag                                          20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
agtgccaaat gcatgctaga                                          20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
tggggctcaa aaacctactg                                          20

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
gtccgggcca agtacctc                                            18

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
atctctcacc gaccccaaat                                          20
```

```
<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
ccattggaag agagacaggt g                                              21

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
tgttgttgtt gttgctgctg                                                20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
tggggctcaa aaacctactg                                                20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ggttggtctt ccttcaggtg                                                20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ggtccaaaag caaccaaaga                                                20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
actggtaaaa agattatggc                                                20

<210> SEQ ID NO 71
<211> LENGTH: 20
<212> TYPE: DNA
<213> ORGANISM: Artificial Sequence
<220> FEATURE:
<223> OTHER INFORMATION: Primer
```

<400> SEQUENCE: 71
caagccgatc aaccagtaca                                          20

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
ccatgctgca agcaatgta                                           19

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
aaccatagga gcagctgaaa ta                                       22

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
accctggtgt agacaaggta                                          20

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
gggagttatg aaactggtat at                                       22

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ataggagcag ctgaagccat                                          20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gtcccgcact tcagaattag                                          20

<210> SEQ ID NO 78

```
<211> LENGTH: 20
<212> TYPE: DNA
<213> ORGANISM: Artificial Sequence
<220> FEATURE:
<223> OTHER INFORMATION: Primer

<400> SEQUENCE: 78
ctctgcttct gcctctgatt                                          20

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
ctggctacta gaatgatgct c                                        21

<210> SEQ ID NO 80
<211> LENGTH: 30
<212> TYPE: DNA
<213> ORGANISM: Artificial Sequence
<220> FEATURE:
<223> OTHER INFORMATION: Primer

<400> SEQUENCE: 80
aattccatgg ggttggtctt ccttcaggtg                               30

<210> SEQ ID NO 81
<211> LENGTH: 30
<212> TYPE: DNA
<213> ORGANISM: Artificial Sequence
<220> FEATURE:
<223> OTHER INFORMATION: Primer

<400> SEQUENCE: 81
aattactagt ttccaccaag ttccagtgaa                               30

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
aattgctagc ggtccaaaag caaccaaaga                               30

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
cttgttgaat tagatggtga tgtt                                     24

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
```
gttgtgggag ttgtagttgt attc                                    24

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
tagcttcaca tccccatgtg                                           20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
gcaccttcac atcttgctgt                                           20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
acatcgccct ggactatgac                                           20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
tgctgagaga tgccaagatg                                           20

<210> SEQ ID NO 89
<211> LENGTH: 56
<212> TYPE: DNA
<213> ORGANISM: Oryza rufipogon

<400> SEQUENCE: 89
tgcatttact gggagttatg aaactggtat atatttcagc tgctcctatg gttaag    56

<210> SEQ ID NO 90
<211> LENGTH: 56
<212> TYPE: DNA
<213> ORGANISM: Oryza rufipogon

<400> SEQUENCE: 90
tgcatttact gggagttatg aaactggtat atatttcagc tgctcctatg gttaag    56

<210> SEQ ID NO 91
<211> LENGTH: 56
<212> TYPE: DNA
<213> ORGANISM: Oryza rufipogon

<400> SEQUENCE: 91

```
tgcatttact gggagttatg aaactggtat atatttcagc tgctcctatg gttaag      56

<210> SEQ ID NO 92
<211> LENGTH: 64
<212> TYPE: DNA
<213> ORGANISM: Oryza rufipogon

<400> SEQUENCE: 92
tgcatttact gggagttatg aaactggtaa aaagattatg gcttcagctg ctcctatggt   60
taag                                                               64

<210> SEQ ID NO 93
<211> LENGTH: 56
<212> TYPE: DNA
<213> ORGANISM: Oryza nivara

<400> SEQUENCE: 93
tgcatttact gggagttatg aaactggtat atatttcagc tgctcctatg gttaag      56

<210> SEQ ID NO 94
<211> LENGTH: 64
<212> TYPE: DNA
<213> ORGANISM: Oryza nivara

<400> SEQUENCE: 94
tgcatttact gggagttatg aaactggtaa aaagattatg gcttcagctg ctcctatggt   60
taag                                                               64

<210> SEQ ID NO 95
<211> LENGTH: 64
<212> TYPE: DNA
<213> ORGANISM: Oryza sativa

<400> SEQUENCE: 95
tgcatttact gggagttatg aaactggtaa aaagattatg gcttcagctg ctcctatggt   60
taag                                                               64

<210> SEQ ID NO 96
<211> LENGTH: 10
<212> TYPE: PRT
<213> ORGANISM: Oryza sativa

<400> SEQUENCE: 96

Val Thr Leu Glu Leu Gly Gly Lys Ser Pro
1               5                   10

<210> SEQ ID NO 97
<211> LENGTH: 4283
<212> TYPE: DNA
<213> ORGANISM: Glycine max

<400> SEQUENCE: 97
ctagctgagt tagggtgagt tgcaggcagt gtcatctctc ctttgacgac aagatgagca   60
tcccaattcc ccatcggcag ttattcatag acggagactg gaaagtcccc gtcctcaaga  120
atcggattcc catcatcaac ccttccaccc aacacatcat cggttctctt ctttcccatt  180
ctctgtctct catcagatct caatctcaat ctcaatctcc ttccttgtct tctcaatgca  240
ggggatatcc cagcagctac taaggaagac gttgatctcg ctgtcgctgc cgccaaagct  300
gccctctccc gcaacaaggg cgccgattgg gcctccgctt ccggctccgt tcgggctcgc  360
```

```
tacctccgcg ccatcgctgc caaggttcct cttatttcac ttttattcta ttttcgctct    420
tttccttatt tccattattc tccctccctc cctcgcagat caccgagaaa aagcctgaac    480
tagcaaaact cgaagctatt gactgtggaa accgctcga tgaagccgcc tgggacatcg     540
taatctctca catccctaaa ttgcaagcaa agaaacaccg attaaagttg tatcactgtg    600
tgttcggtta tttgtttctg taggacgatg ttgctggttg ctttgagttc tatgctgacc    660
ttgctgaaaa attggacgca cagcaaaagg ctcatgtgtc tcttcccatg gacacattca    720
agagttatgt tcttaaggag ccgattggag tcgttgcttt ataactcct tggtactacc     780
ttctccttct ctctctctct ctctctctgc tcttttttaa ctgaatccga tgctttactt    840
taatcattgc attgcatttg tgaatcatca tcctctgttg atggcgtttt aggaattatc    900
ctctgttgat ggctacgtgg aaggttgctc ctgctctggc ggccggctgt gctgcaatat    960
tgaagccctc tgagttggca tctgtgtatg ttttgttct ccatgactgt ctgttgctgt    1020
cttgcttctt tgttttgttt tgttcgttgc ttggtttctt ctcatgctat gttgtcatgt    1080
gttgttgtgt gcaattttta ggacatgttt ggagctcgct gaaatttgca aagaagtcgg    1140
gcttcctcct ggcgtgttga acattctcac tggattagga cctgaagcgg gtgctccttt    1200
agcagctcat cccgatgtag acaaggttca attttaaaa gaattgaacc tgtatggggc     1260
tatatcttgt ttatgtctt cacattgttg cacacaaggt tttaaattgt agtcacggtc     1320
gcaattttgt caatccttca attacaaaca gatgcatgtg gtcacaattg tggtcgcgga    1380
aagccaaaaa atacttttg tcccagccaa aattgcggcc acgcgctgtt tttaaaaaac     1440
ctcatttgcg tgtatcatta ctgagatttc tttgagtttg caatgctagt ttgacattgt    1500
ggccgtaatt tttccaatag attgccttta ctggaagctc tgcaactggg agcaaaatta    1560
tgacagctgc agctcagctg atcaaggtat ttttgagcag ttatctgtaa gttatgaaca    1620
gttcgtgttt ccatttgttt tgatagaaca agaacaaaca aagacatgct cagaaagaga    1680
taggaacccc ttttttcccc tttacatgtt ttaattgtgt tttcttcatg aatcacttta    1740
acataaaatg tgtggtttct tggcagcctg tttcactaga gcttggtggg aaaagcccaa    1800
tcattgtttt tgaggatgtt gaccttgaca agggtcagtg acttcgcaag tatagtgatt    1860
tagttatgga cagcacttgt ttacttgcat cacaaaatca cctttcctta aataatgagt    1920
gaggatgagt aatttttttt catctatttc ctattgcatg atttagatcc tttctccatg    1980
atttaaacag ctgctgaatg gaccatattt ggttgcttct ggacaaatgg tcagatatgc    2040
agtgcaactt cccgccttat tgtacatgca agttttgtct tctttaactt caactgtggt    2100
tgaatttttt cagcaccttg atagaaatta tgttggcatt tatcttcaaa aactaagata    2160
ctctcatttt tcaggaaagt atagcaacag aatttgaata ggattgtgaa atgggtcaaa    2220
aacatcaaaa tttctgatcc cttggaagaa ggttgcagac taggccctat tgttagtgaa    2280
ggacgggcat attttctgtt tctcatttct gcatatatgt cctactctct ttctaaagta    2340
aaggacagtt atgctctggt atgctatcat catgttgacc ttattcaata ttcaaaacga    2400
gaatgtgttg ataataggct atcatcatta attatgaatt atcatcaagc tgaatgtagt    2460
atggaataat gcaaaatctt ccttagaaga attattggtt agctggctat atatattttt    2520
gagagggagt cagagaagaa agaaccttct ccggatcatt gtgtatgttc ctatgattta    2580
gctttctctc tgttcttata acttaacatc ttattgatat aagcatactt ttcttgaaca    2640
aaggttatct aatattttata ttatatggtt cagtatgaaa agatattgaa gtttatctca    2700
aatgctaaga gtgagggtgc aaccattttg actggtgggt ctcgcccaga ggtatgatta    2760
```

| | |
|---|---|
| tactttctttt gaaggtgtgt tttggttacg tgcttctgca attcctgtgg gaattgaatt | 2820 |
| tattttctct ctcaaattca atggcagcat ctaaagaagg gattctttgt tgaaccaact | 2880 |
| gtcataactg atgtaactac ctccatgcaa atttggagag aagaagtatt tggaccagtt | 2940 |
| ctctgtgtaa aaacatttag cactgaggaa gaagctattg atctagcaaa tgacactgtg | 3000 |
| tgagctgatg ttttctgtga actggcgaca ttaacttcct ctgtaaaaaa aattttccct | 3060 |
| tcattttttgg tttgatatct aagttatata ctttaacctt ccacagatat ggcttgggtt | 3120 |
| ctgctgtaat atcaaatgat ctagaaagat gtgagcgcat tactaaggtg agactaatcc | 3180 |
| taggttatca cagaaaacaa aaaatgattg gattgtttct gcagctaaat agttcaactt | 3240 |
| gcttcaatgc aggcttttaa ggctggaatt gtgtggatta attgctctca accatgcttc | 3300 |
| actcaagccc catggggagg cattaaacgc agtggttttg gtcgtgaatt aggagaatgg | 3360 |
| tatggtcctt atttcctaaa ttaacaaatg caagtaacct caaataactt tcttctctttt | 3420 |
| gcctggatat catgtctaac atgcaaaaga aacttacatt tataagttga agtccatgga | 3480 |
| ttgttgaatg ctcctgtacc actcaaccgt tgacagtttg ttgaccatca gattttgtac | 3540 |
| aaccaaattt aatcaaaagg tcgataaagc tgtgtaacat cgtggcactg gtgcagcttt | 3600 |
| gcactttttta gttggagtaa ttttaaatca tagggattgt gatgcattga cacatttaaa | 3660 |
| ttaataaact aataataaaa aagtcaccta cgatttgagt gaatttattc taaagttgtc | 3720 |
| acgttccttt ggtttgaagc tagcataaaa aatgaatagg gtcacagaga cagtagatta | 3780 |
| aactcacgca caattgcaaa agagaaaaca taccttcacc tcgatcattc tcagatatgg | 3840 |
| tgtggaaaat aaaaactttt aagctttttat ttgagcttct gagtaatttt tcttattaac | 3900 |
| tttttcaggg gacttgataa ttacttgagt gtgaagcaag tgacccaata tatctctgat | 3960 |
| gaaccgtggg gctggtacca gtctccttca aggctgtgat aggtatccaa aagctaacat | 4020 |
| taataagttg tgggtaatat caaattatga ttatgacccc aaagtcgaga agacatgatg | 4080 |
| tctatgtata acattgaaat ggttttgcact ttgcagtcaa gattatgttg gtagtgtttt | 4140 |
| tatttgattt gtttatggtt ggctccacca catgcttcta atgtttgaat ttcatcatgg | 4200 |
| aagacttcca tcattacatt atattgaagc atttcttgcg cttaagttac gaatcatgca | 4260 |
| tcaatagatc tgacttaaaa ttg | 4283 |

<210> SEQ ID NO 98
<211> LENGTH: 1510
<212> TYPE: DNA
<213> ORGANISM: Glycine max

<400> SEQUENCE: 98

| | |
|---|---|
| atgagcatcc caattcccca tcggcagtta ttcatagacg gagactggaa agtcccccgtc | 60 |
| ctcaagaatc ggattcccat catcaaccct tccacccaac acatcatcgg ggatatccca | 120 |
| gcagctacta aggaagacgt tgatctcgct gtcgctgccg ccaaagctgc cctctcccgc | 180 |
| aacaagggcg ccgattgggc ctccgcttcc ggctccgttc gggctcgcta cctccgcgcc | 240 |
| atcgctgcca agatcaccga gaaaaagcct gaactagcaa aactcgaagc tattgactgt | 300 |
| ggaaaaccgc tcgatgaagc cgcctgggac atcgacgatg ttgctggttg ctttgagttc | 360 |
| tatgctgacc ttgctgaaaa attggacgca cagcaaaagg ctcatgtgtc tcttcccatg | 420 |
| gacacattca agagttatgt tcttaaggag ccgattggag tcgttgcttt aataactcct | 480 |
| tggaattatc ctctgttgat ggctacgtgg aaggttgctc ctgctctggc ggccggctgt | 540 |

```
gctgcaatat tgaagccctc tgagttggca tctgtgacat gtttggagct cgctgaaatt      600
tgcaaagaag tcgggcttcc tcctggcgtg ttgaacattc tcactggatt aggacctgaa      660
gcgggtgctc ctttagcagc tcatcccgat gtagacaaga ttgcctttac tggaagctct      720
gcaactggga gcaaaattat gacagctgca gctcagctga tcaagcctgt ttcactagag      780
cttggtggga aagcccaat cattgttttt gaggatgttg accttgacaa ggctgctgaa       840
tggaccatat ttggttgctt ctggacaaat ggtcagatat gcagtgcaac ttcccgcctt      900
attgtacatg aaagtatagc aacagaattt gaataggatt gtgaaatggg tcaaaaacat      960
caaaatttct gatcccttgg aagaaggttg cagactaggc cctattgtta gtgaaggaca     1020
gtatgaaaag atattgaagt ttatctcaaa tgctaagagt gagggtgcaa ccattttgac     1080
tggtgggtct cgcccagagc atctaaagaa gggattcttt gttgaaccaa ctgtcataac     1140
tgatgtaact acctccatgc aaatttggag agaagaagta tttggaccag ttctctgtgt     1200
aaaaacattt agcactgagg aagaagctat tgatctagca aatgacactg tatatggctt     1260
gggttctgct gtaatatcaa atgatctaga aagatgtgag cgcattacta aggcttttaa     1320
ggctggaatt gtgtggatta attgctctca accatgcttc actcaagccc catgggagg      1380 cattaaacgc agtggttttg gtcgtgaatt aggagaatgg ggacttgata attacttgag     1440
tgtgaagcaa gtgacccaat atatctctga tgaaccgtgg ggctggtacc agtctccttc     1500
aaggctgtga                                                            1510

<210> SEQ ID NO 99
<211> LENGTH: 311
<212> TYPE: PRT
<213> ORGANISM: Glycine max

<400> SEQUENCE: 99

Met Ser Ile Pro Ile Pro His Arg Gln Leu Phe Ile Asp Gly Asp Trp
  1               5                  10                  15

Lys Val Pro Val Leu Lys Asn Arg Ile Pro Ile Ile Asn Pro Ser Thr
             20                  25                  30

Gln His Ile Ile Gly Asp Ile Pro Ala Ala Thr Lys Glu Asp Val Asp
         35                  40                  45

Leu Ala Val Ala Ala Ala Lys Ala Ala Leu Ser Arg Asn Lys Gly Ala
     50                  55                  60

Asp Trp Ala Ser Ala Ser Gly Ser Val Arg Ala Arg Tyr Leu Arg Ala
 65                  70                  75                  80

Ile Ala Ala Lys Ile Thr Glu Lys Lys Pro Glu Leu Ala Lys Leu Glu
                 85                  90                  95

Ala Ile Asp Cys Gly Lys Pro Leu Asp Glu Ala Ala Trp Asp Ile Asp
            100                 105                 110

Asp Val Ala Gly Cys Phe Glu Phe Tyr Ala Asp Leu Ala Glu Lys Leu
        115                 120                 125

Asp Ala Gln Gln Lys Ala His Val Ser Leu Pro Met Asp Thr Phe Lys
    130                 135                 140

Ser Tyr Val Leu Lys Glu Pro Ile Gly Val Val Ala Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Ala Ala Ile Leu Lys Pro Ser Glu Leu Ala Ser Val
            180                 185                 190

Thr Cys Leu Glu Leu Ala Glu Ile Cys Lys Glu Val Gly Leu Pro Pro
```

|  |  | 195 |  |  |  | 200 |  |  |  | 205 |  |
|---|---|---|---|---|---|---|---|---|---|---|---|

Gly Val Leu Asn Ile Leu Thr Gly Leu Gly Pro Glu Ala Gly Ala Pro
210 215 220

Leu Ala Ala His Pro Asp Val Asp Lys Ile Ala Phe Thr Gly Ser Ser
225 230 235 240

Ala Thr Gly Ser Lys Ile Met Thr Ala Ala Gln Leu Ile Lys Pro
245 250 255

Val Ser Leu Glu Leu Gly Gly Lys Ser Pro Ile Ile Val Phe Glu Asp
260 265 270

Val Asp Leu Asp Lys Ala Ala Glu Trp Thr Ile Phe Gly Cys Phe Trp
275 280 285

Thr Asn Gly Gln Ile Cys Ser Ala Thr Ser Arg Leu Ile Val His Glu
290 295 300

Ser Ile Ala Thr Glu Phe Glu
305 310

<210> SEQ ID NO 100
<211> LENGTH: 4307
<212> TYPE: DNA
<213> ORGANISM: Glycine max

<400> SEQUENCE: 100

```
agagactgga ctagctgagt tagggtgagt tgcaggcagt gtcatctctc ctttgacgac    60
aagatgagca tcccaattcc ccatcggcag ttattcatag acggagactg aaagtcccc   120
gtcctcaaga tcggattcc catcatcaac ccttccaccc aacacatcat cggttctctt   180
ctttcccatt ctctgtctct catcagatct caatctcaat ctcaatctcc ttccttgtct   240
tctcaatgca ggggatatcc cagcagctac taaggaagac gttgatctcg ctgtcgctgc   300
cgccaaagct gccctctccc gcaacaaggg cgccgattgg gcctccgctt ccggctccgt   360
tcgggctcgc tacctccgcg ccatcgctgc caaggttcct cttatttcac ttttattcta   420
ttttcgctct tttccttatt tccattattc tccctccctc cctcgcagat caccgagaaa   480
aagcctgaac tagcaaaact cgaagctatt gactgtggaa aaccgctcga tgaagccgcc   540
tgggacatcg taatctctca catccctaaa ttgcaagcaa agaaacaccg attaaagttg   600
tatcactgtg tgttcggtta tttgtttctg taggacgatg ttgctggttg ctttgagttc   660
tatgctgacc ttgctgaaaa attggacgca cagcaaaagg ctcatgtgtc tcttcccatg   720
gacacattca agagttatgt tcttaaggag ccgattggag tcgttgcttt aataactcct   780
tggtactacc ttctccttct ctctctctct ctctctctgc tcttttttaa ctgaatccga   840
tgctttactt taatcattgc attgcatttg tgaatcatca tcctctgttg atggcgtttt   900
aggaattatc ctctgttgat ggctacgtgg aaggttgctc ctgctctggc ggccggctgt   960
gctgcaatat tgaagccctc tgagttggca tctgtgtatg ttttttgttct ccatgactgt  1020
ctgttgctgt cttgcttctt tgttttgttt tgttcgttgc ttggtttctt ctcattctat  1080
gttgtcatgt gttgttgtgt gcaattttta ggacatgttt ggagctcgct gaaatttgca  1140
aagaagtcgg gcttcctcct ggcgtgttga acattctcac tggattagga cctgaagcgg  1200
gtgctccttt agcagctcat cccgatgtag acaaggttca attttaaaa gaattgaagc  1260
tgtatggggc tatatcttgt ttttatgtct cacattgttg cacacaaggt tttaaattgc  1320
agtcacggtc gcaattttgt caatccttca attacaaaca gatgcatgtg gtcacaattg  1380
tggtcgcgga aagccaaaaa aaactttatg tcccagccaa aattgcggcc acgcgctgtt  1440
```

```
tttgaaaaac ctcgtttgcg tgtatcatta ctgagatttc tttgagtttg caatgctagt    1500
ttgacattgt ggccgtaatt tttccaatag attgccttta ctggaagctc tgcaactggg    1560
agcaaaatta tgacagctgc agctcagctg atcaaggtat ttttgagcag ttatctgtaa    1620
gttatgaaca gttcgtgttt ccatttgttt tgatagaaca aagaacaaat aaaggcatgc    1680
tcagaaagag ataggaaccc cttttttttcc ccttacatgt tttaattgtg ttttcttcat   1740
gaatcactct aacataaaat gtgtggtttc ttggcagcct gtttcactag agcttggtgg    1800
gaaaagccca atcattgttt tgaggatgt tgaccttgac aagggtcagt gacttcgcaa     1860
gtatagtgat ttagttatgg acagcacttg tctacttgca tcacaaaatc acatttcctt    1920
aaatactgag tgaggatgag taattttttt tcatctattt cctattgcat gatttagatc    1980
ctttctccat gatttaaaca gctgctgaat ggaccatatt tggttgcttc tggacaaatg    2040
gtcagatatg cagtgcaact tcccgcctta ttgtacatgc aagttttgtc ttctttaact    2100
tcaactgtgg ttgaatttt tcagcacctt gatagaaatt atgttggcat ttatcttcaa     2160
aaactaagat actctcattt ttcaggaaag tatagcaaca gaattttga ataggattgt     2220 gaaatgggtc aaaacatca aaatttctga tcccttggaa aaggttgca gactaggccc      2280 tattgttagt gaaggacagg tatattttct gttttctcatt tctgtatatc ttatgcattt   2340
acgtcctact ctctttctaa agtaaagggc aggtatgctt tggtatgttc aaatgccctt    2400
attcaatatt caaaatgaga atgtgattaa tatgatatca tcattaatta tgaattatga    2460
tcaagcttaa tgtagtatgg aataatgcat aagcttcctt agaagaatta ttggttggct    2520
ggctatatat atattatgag aaggagtcag agaaggaacc ttctcctggt tgttgtatat    2580
gttcctatga tttagctttc tctctgttct tataacttaa aacatcttat tgatataagc    2640 atattttct tgaacaaaga ttatctaata tttatattat atggttcagt atgaaaagat    2700
attgaagttt atctcaaatg ctaagagtga gggtgcaacc attttgactg gtgggtctcg    2760
cccagaggta tgattataca tttataattt ctttgaaggt gtgttttggt tatgtgcttc    2820
tgcaattgtt gtgagaattg atttttttt tctttctgaa attcaatggc agcatctaaa     2880
gaagggattc tttgttgaac caactgtcat aactgatgta actacctcca tgcaaatttg    2940
gagagaagaa gtatttggac cagttctctg tgtaaaaaca tttagcactg aggaagaagc    3000
tattgatcta gcaaatgaca ctgtgtgagc tgatgttttc tgtgaactgg cgacattaac    3060
ttcctctgta aaaaaaaatt tcccttcatt tttggtttga tatctaagtt atatacttta    3120
accttccaca gatatggctt gggttctgct gtaatatcaa atgatctaga agatgtgag    3180 cgcattacta aggtgagact aatcctaggt tatcacagaa aacaaaaaat gattggattg    3240
tttctgcagc taaatagttc atcttgcttc aatgcaggct tttaaggctg gaattgtgtg    3300
gattaattgc tctcaaccat gcttcactca agccccatgg ggaggcatta aacgcagtgg    3360
ttttggtcgt gaattaggag aatggtatgg tccttatttc ctaaattaac aaatgcaagt    3420
aacctcaaat acctttcttc tctttgcctg gatatcatgt ctaacatgca aaagaaactt    3480
acatttataa gttgaagtcc atggattgtt gaatgctcct gtaccactca accgttgaca    3540
gtttgttgac catcagattt tgtacaacca aatttaatca aaaggtcgat aaagctgtgt    3600
aacatcgtgg cactggtgca gctttgcact ttttagttgg agtaatttta aatcataggg    3660
attgtgatgc attgacacat ttaaattaat aaactaataa taaaaagtc acctacgatt      3720 tgagtgaatt tattctaagt tgtcacgttc ctttggtttg aagctagcat aaaaaatgaa    3780
tagggtcaca gagacagtag attaaactca cgcacaattg caaagagaa aacatacctt      3840
```

```
cacctcgatc attctcagat atggtgtgga aaataaaaac ttttaagctt ttatttgagc    3900
ttctgagtaa tttttcttat taactttttc aggggacttg ataattactt gagtgtgaag    3960
caagtgaccc aatatatctc tgatgaaccg tggggctggt accagtctcc ttcaaggctg    4020
tgataggtat ccaaaagcta acattaataa gttgtgggta atatcaaatt acgattatga    4080
ccccaaagtc gagaagacat gatgtctatg tataacattg aaatggtttg cactttgcag    4140
tcaagattat gttggtagtg ttttttatttg atttgtttat ggttggctcc accacatgct    4200
tctaatgttt gaatttcatc atggaagact tccatcatta cattatattg aagcatttct    4260
tgcgcttaag ttacgaatca tgcatcaata gatctgactt aaaattg                  4307
```

<210> SEQ ID NO 101
<211> LENGTH: 1512
<212> TYPE: DNA
<213> ORGANISM: Glycine max

<400> SEQUENCE: 101

```
atgagcatcc caattcccca tcggcagtta ttcatagacg gagactggaa agtccccgtc      60
ctcaagaatc ggattcccat catcaaccct tccacccaac acatcatcgg ggatatccca     120
gcagctacta aggaagacgt tgatctcgct gtcgctgccg ccaaagctgc cctctcccgc     180
aacaagggcg ccgattgggc ctccgcttcc ggctccgttc gggctcgcta cctccgcgcc     240
atcgctgcca agatcaccga gaaaaagcct gaactagcaa aactcgaagc tattgactgt     300
ggaaaaccgc tcgatgaagc cgcctgggac atcgacgatg ttgctggttg ctttgagttc     360
tatgctgacc ttgctgaaaa attggacgca cagcaaaagg ctcatgtgtc tcttcccatg     420
gacacattca agagttatgt tcttaaggag ccgattggag tcgttgcttt aataactcct     480
tggaattatc ctctgttgat ggctacgtgg aaggttgctc ctgctctggc ggccggctgt     540
gctgcaatat tgaagccctc tgagttggca tctgtgacat gtttggagct cgctgaaatt     600
tgcaaagaag tcgggcttcc tcctggcgtg ttgaacattc tcactggatt aggacctgaa     660
gcgggtgctc ctttagcagc tcatcccgat gtagacaaga ttgcctttac tggaagctct     720
gcaactggga gcaaaattat gacagctgca gctcagctga tcaagcctgt ttcactagag     780
cttggtggga aaagcccaat cattgttttt gaggatgttg accttgacaa ggctgctgaa     840
tggaccatat ttggttgctt ctggacaaat ggtcagatat gcagtgcaac ttcccgcctt     900
attgtacatg aaagtatagc aacagaattt ttgaatagga ttgtgaaatg ggtcaaaaac     960
atcaaaattt ctgatccctt ggaagaaggt tgcagactag gccctattgt tagtgaagga    1020
cagtatgaaa agatattgaa gtttatctca aatgctaaga gtgagggtgc aaccattttg    1080
actggtgggt ctcgcccaga gcatctaaag aagggattct tgttgaacc aactgtcata    1140 actgatgtaa ctacctccat gcaaatttgg agagaagaag tatttggacc agttctctgt    1200
gtaaaaacat ttagcactga ggaagaagct attgatctag caaatgacac tgtatatggc    1260
ttgggttctg ctgtaatatc aaatgatcta gaaagatgtg agcgcattac taaggctttt    1320
aaggctggaa ttgtgtggat taattgctct caaccatgct tcactcaagc cccatgggga    1380
ggcattaaac gcagtggttt tggtcgtgaa ttaggagaat ggggacttga taattacttg    1440
agtgtgaagc aagtgaccca atatatctct gatgaaccgt ggggctggta ccagtctcct    1500
tcaaggctgt ga                                                        1512
```

<210> SEQ ID NO 102

-continued

<211> LENGTH: 503
<212> TYPE: PRT
<213> ORGANISM: Glycine max

<400> SEQUENCE: 102

```
Met Ser Ile Pro Ile Pro His Arg Gln Leu Phe Ile Asp Gly Asp Trp
  1               5                  10                  15

Lys Val Pro Val Leu Lys Asn Arg Ile Pro Ile Ile Asn Pro Ser Thr
             20                  25                  30

Gln His Ile Ile Gly Asp Ile Pro Ala Ala Thr Lys Glu Asp Val Asp
         35                  40                  45

Leu Ala Val Ala Ala Ala Lys Ala Ala Leu Ser Arg Asn Lys Gly Ala
 50                  55                  60

Asp Trp Ala Ser Ala Ser Gly Ser Val Arg Ala Arg Tyr Leu Arg Ala
 65                  70                  75                  80

Ile Ala Ala Lys Ile Thr Glu Lys Lys Pro Glu Leu Ala Lys Leu Glu
                 85                  90                  95

Ala Ile Asp Cys Gly Lys Pro Leu Asp Glu Ala Ala Trp Asp Ile Asp
            100                 105                 110

Asp Val Ala Gly Cys Phe Glu Phe Tyr Ala Asp Leu Ala Glu Lys Leu
        115                 120                 125

Asp Ala Gln Gln Lys Ala His Val Ser Leu Pro Met Asp Thr Phe Lys
130                 135                 140

Ser Tyr Val Leu Lys Glu Pro Ile Gly Val Val Ala Leu Ile Thr Pro
145                 150                 155                 160

Trp Asn Tyr Pro Leu Leu Met Ala Thr Trp Lys Val Ala Pro Ala Leu
                165                 170                 175

Ala Ala Gly Cys Ala Ala Ile Leu Lys Pro Ser Glu Leu Ala Ser Val
            180                 185                 190

Thr Cys Leu Glu Leu Ala Glu Ile Cys Lys Glu Val Gly Leu Pro Pro
        195                 200                 205

Gly Val Leu Asn Ile Leu Thr Gly Leu Gly Pro Glu Ala Gly Ala Pro
210                 215                 220

Leu Ala Ala His Pro Asp Val Asp Lys Ile Ala Phe Thr Gly Ser Ser
225                 230                 235                 240

Ala Thr Gly Ser Lys Ile Met Thr Ala Ala Ala Gln Leu Ile Lys Pro
                245                 250                 255

Val Ser Leu Glu Leu Gly Gly Lys Ser Pro Ile Ile Val Phe Glu Asp
            260                 265                 270

Val Asp Leu Asp Lys Ala Ala Glu Trp Thr Ile Phe Gly Cys Phe Trp
        275                 280                 285

Thr Asn Gly Gln Ile Cys Ser Ala Thr Ser Arg Leu Ile Val His Glu
290                 295                 300

Ser Ile Ala Thr Glu Phe Leu Asn Arg Ile Val Lys Trp Val Lys Asn
305                 310                 315                 320

Ile Lys Ile Ser Asp Pro Leu Glu Glu Gly Cys Arg Leu Gly Pro Ile
                325                 330                 335

Val Ser Glu Gly Gln Tyr Glu Lys Ile Leu Lys Phe Ile Ser Asn Ala
            340                 345                 350

Lys Ser Glu Gly Ala Thr Ile Leu Thr Gly Gly Ser Arg Pro Glu His
        355                 360                 365

Leu Lys Lys Gly Phe Phe Val Glu Pro Thr Val Ile Thr Asp Val Thr
370                 375                 380

Thr Ser Met Gln Ile Trp Arg Glu Glu Val Phe Gly Pro Val Leu Cys
```

```
                385                 390                 395                 400
Val Lys Thr Phe Ser Thr Glu Glu Ala Ile Asp Leu Ala Asn Asp
                    405                 410                 415

Thr Val Tyr Gly Leu Gly Ser Ala Val Ile Ser Asn Asp Leu Glu Arg
                420                 425                 430

Cys Glu Arg Ile Thr Lys Ala Phe Lys Ala Gly Ile Val Trp Ile Asn
                435                 440                 445

Cys Ser Gln Pro Cys Phe Thr Gln Ala Pro Trp Gly Gly Ile Lys Arg
            450                 455                 460

Ser Gly Phe Gly Arg Glu Leu Gly Glu Trp Gly Leu Asp Asn Tyr Leu
465                 470                 475                 480

Ser Val Lys Gln Val Thr Gln Tyr Ile Ser Asp Glu Pro Trp Gly Trp
                485                 490                 495

Tyr Gln Ser Pro Ser Arg Leu
            500

<210> SEQ ID NO 103
<211> LENGTH: 60
<212> TYPE: DNA
<213> ORGANISM: Artificial Sequence
<220> FEATURE:
<223> OTHER INFORMATION: Synthetic Construct

<400> SEQUENCE: 103
acatgaaagt atagcaacag aattttttgaa taggattgtg aaatgggtca aaaacatcaa    60

<210> SEQ ID NO 104
<211> LENGTH: 58
<212> TYPE: DNA
<213> ORGANISM: Artificial Sequence
<220> FEATURE:
<223> OTHER INFORMATION: Synthetic Construct

<400> SEQUENCE: 104
acatgaaagt atagcaacag aatttgaata ggattgtgaa atgggtcaaa aacatcaa    58

<210> SEQ ID NO 105
<211> LENGTH: 12
<212> TYPE: PRT
<213> ORGANISM: Artificial Sequence
<220> FEATURE:
<223> OTHER INFORMATION: Synthetic Construct

<400> SEQUENCE: 105

Phe Trp Thr Asn Gly Gln Ile Cys Ser Ala Thr Ser
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic Construct

<400> SEQUENCE: 106

Phe Ala Asn Ala Gly Gln Val Cys Ser Ala Thr Ser
1               5                   10

<210> SEQ ID NO 107
<211> LENGTH: 12
<212> TYPE: PRT
<213> ORGANISM: Artificial Sequence
<220> FEATURE:
```

<223> OTHER INFORMATION: Synthetic Construct

<400> SEQUENCE: 107

Phe Ala Asn Gly Gly Gln Val Cys Ser Ala Thr Ser
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic Construct

<400> SEQUENCE: 108

Phe Phe Asn Gly Gly Gln Val Cys Ser Ala Thr Ser
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Construct

<400> SEQUENCE: 109

Phe Trp Thr Asn Gly Gln Ile Cys Ser Ser Thr Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic Construct

<400> SEQUENCE: 110

Phe Phe Thr Asn Gly Gln Ile Cys Ser Ala Thr Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct

<400> SEQUENCE: 111

Phe Pro Asn Asn Gly Gln Ile Cys Ser Ala Thr Ser
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic Construct
<221> NAME/KEY: VARIANT
<222> LOCATION: 1
<223> OTHER INFORMATION: Xaa = Phe or Tyr or Leu or Val or Ala
<221> NAME/KEY: VARIANT
<222> LOCATION: 2
<223> OTHER INFORMATION: Xaa = Any Amino Acid
<221> NAME/KEY: VARIANT
<222> LOCATION: 3
<223> OTHER INFORMATION: Xaa = Gly or Val or Glu or Pro
<221> NAME/KEY: VARIANT
<222> LOCATION: 4
<223> OTHER INFORMATION: Xaa = Asp or Ile or Leu or Val
<221> NAME/KEY: VARIANT

```
<222> LOCATION: 6
<223> OTHER INFORMATION: Xaa = Gln or Glu
<221> NAME/KEY: VARIANT
<222> LOCATION: 7
<223> OTHER INFORMATION: Xaa = Leu or Pro or Tyr or Gly
<221> NAME/KEY: VARIANT
<222> LOCATION: 9
<223> OTHER INFORMATION: Xaa = Leu, Ile, Val, Met, Gly, Ser, Thr, Ala,
      Asn or Cys
<221> NAME/KEY: VARIANT
<222> LOCATION: 10
<223> OTHER INFORMATION: Xaa = Ala or Gly or Cys or Asn
<221> NAME/KEY: VARIANT
<222> LOCATION: 11
<223> OTHER INFORMATION: Xaa = His or Glu
<221> NAME/KEY: VARIANT
<222> LOCATION: 12
<223> OTHER INFORMATION: Xaa = Gly, Ser, Thr, Ala, Asp, Asn, Glu, Lys or
      Arg

<400> SEQUENCE: 112

Xaa Xaa Xaa Xaa Gly Xaa Xaa Cys Xaa Xaa Xaa Xaa
1               5                   10
```